(12) United States Patent
Klausnitzer et al.

(10) Patent No.: US 12,292,378 B2
(45) Date of Patent: May 6, 2025

(54) METHOD FOR DETERMINING THE COMPOSITION OF A MULTI-LAYER SYSTEM SHOWING A PREDETERMINED COLOUR FLIP-FLOP EFFECT

(71) Applicant: HUBERGROUP DEUTSCHLAND GMBH, Kirchheim-Heimstetten (DE)

(72) Inventors: Sylvia Klausnitzer, Bruckmuehl (DE); Taner Bicer, Grafing (DE); Lutz Frischmann, Ismaning (DE); Ralf Buescher, Lohmar (DE)

(73) Assignee: hubergroup Deutschland GmbH, Kirchheim-Heimstetten (DE)

( * ) Notice: Subject to any disclaimer, the term of this patent is extended or adjusted under 35 U.S.C. 154(b) by 304 days.

(21) Appl. No.: 17/632,526

(22) PCT Filed: Jul. 29, 2020

(86) PCT No.: PCT/EP2020/071380
§ 371 (c)(1),
(2) Date: Feb. 3, 2022

(87) PCT Pub. No.: WO2021/023595
PCT Pub. Date: Feb. 11, 2021

(65) Prior Publication Data
US 2022/0283085 A1    Sep. 8, 2022

(30) Foreign Application Priority Data
Aug. 6, 2019  (EP) ..................................... 19190181

(51) Int. Cl.
*G01N 21/47*     (2006.01)
*C09D 11/033*    (2014.01)
(Continued)

(52) U.S. Cl.
CPC ....... *G01N 21/4738* (2013.01); *C09D 11/033* (2013.01); *C09D 11/037* (2013.01);
(Continued)

(58) Field of Classification Search
CPC .......... C09D 5/29; C09D 7/61; C09D 11/037; C09D 7/70; C09D 7/68; C09D 7/67;
(Continued)

(56) References Cited

U.S. PATENT DOCUMENTS

| | | | |
|---|---|---|---|
| 6,064,487 | A | 5/2000 | Kettler et al. |
| 7,077,897 | B2 | 7/2006 | Brueckner et al. |

(Continued)

FOREIGN PATENT DOCUMENTS

| | | | | |
|---|---|---|---|---|
| CN | 1666094 | A * | 9/2005 | ............ G01J 3/0251 |
| CN | 104114985 | A * | 10/2014 | ............ B05D 5/005 |

(Continued)

OTHER PUBLICATIONS

Box et al., Empirical Model-Building and Response Surfaces (Wiley 1987, ISBN-13: 978-0471810339) pp. 10-14.
(Continued)

*Primary Examiner* — Michael P Stafira
(74) *Attorney, Agent, or Firm* — LELKES IP; Robert Lelkes

(57) ABSTRACT

The present invention relates to a method for determining the composition of a multi-layer system showing a predetermined colour flip-flop effect, wherein the multi-layer system comprises from bottom to top a) a substrate, b) at least one first colour layer containing a colourant, which is arranged on the substrate a), c) on the at least one first colour layer an effect layer containing at least one platelet-shaped effect pigment, and d) on the effect layer c) at least one second colour layer containing a colourant, wherein each of (Continued)

the at least one first colour layer and of the at least one second colour layer contains a colourant being no platelet-shaped effect pigment, wherein the method comprises the following steps: i) specifying a first target value for the colour shade and/or colour brightness of the top side of the multi-layer system seen at a first observation angle, ii) specifying a second target value for the colour shade and/or colour brightness of the top side of the multi-layer system seen at a second observation angle, wherein the second observation angle is different from the first observation angle, and wherein the second target value is different from the first target value, iii) specifying a colourant system comprising at least one colourant and further comprising one effect pigment layer recipe being suitable for forming the effect layer c), iv) providing at least one empirical model of the relationship between the colour shades and/or colour brightness at least two different observation angles comprising at least the first observation angle and the second observation angle specified in step ii) of the top side of a first number of multi-layer systems, at least 90% of which comprising at least one first colour layer b) having at least one colourant as specified in step iii), at least one second colour layer d) having at least one colourant as specified in step iii) and an effect layer c) made of the effect pigment layer recipe specified in step iii), and v) determining—making use of the at least one empirical model provided in step iv)—the composition of a multi-layer system (10) having within a predetermined tolerance the first target value specified in step i) and the second target value specified in step ii), or, if none is found, specifying a new tolerance for the first target value specified in step i) and/or the second target value specified in step ii), or specifying in steps i) and ii) a new first target value and/or new the second target value, or repeating the method by specifying in step iii) a different colourant system, which preferably covers more different colourants than the colourant system used before, wherein the determination in step v) is performed by using a computer program.

15 Claims, 3 Drawing Sheets

(51) Int. Cl.
*C09D 11/037* (2014.01)
*C09D 11/50* (2014.01)
*G01N 21/25* (2006.01)
*G01N 21/84* (2006.01)
*B05D 5/06* (2006.01)

(52) U.S. Cl.
CPC ........... *C09D 11/50* (2013.01); *G01N 21/255* (2013.01); *G01N 21/8422* (2013.01); *B05D 5/066* (2013.01); *G01N 2021/4711* (2013.01); *G01N 2021/8438* (2013.01)

(58) Field of Classification Search
CPC ..... C09D 11/50; C09D 11/101; C09D 11/107; C09D 11/14; C09D 5/36; C09D 175/04; C09D 7/69; C09D 5/38; C09D 11/00; C09D 11/033; C09D 5/28; C09D 7/41; C09D 101/18; C09D 167/00; C09D 5/00; C09D 5/032; C09D 7/62; C09D 1/00; C09D 133/04; C09D 163/00; C09D 167/02; C09D 5/033; C09D 5/035; C09D 5/036; C09D 7/00; C09D 7/66; C09D 101/00; C09D 11/322; C09D 133/064; C09D 133/00; C09D 151/003; C09D 161/28; C09D 5/028; C09D 5/24; C09D 7/40; C09D 11/08; C09D 11/38; C09D 11/40; C09D 11/52; C09D 15/00; C09D 151/06; C09D 167/025; C09D 5/02; C09D 5/024; C09D 7/65; G01N 21/255; G01N 21/4738; G01N 21/8422; G01N 2021/4711; G01N 2021/8438; G01N 21/57; G01N 21/84
See application file for complete search history.

(56) References Cited

U.S. PATENT DOCUMENTS

2003/0223060 A1* 12/2003 Graf ................. G01J 3/504
356/319
2015/0127269 A1 5/2015 Bell et al.
2015/0138641 A1* 5/2015 Delst ................. G02B 5/286
359/584
2019/0011618 A1 1/2019 Delst et al.

FOREIGN PATENT DOCUMENTS

CN 105556285 A * 5/2016 .............. G01J 3/463
JP 2002285094 A 10/2002
JP 2017128054 A * 7/2017

OTHER PUBLICATIONS

Box et al., Statistics for Experimenters—Design, Innovation and Discovery, 2nd edition (Wiley 2005, ISBN-13: 978-0471718130) pp. 235-245.
Goos et al., Optimal Design of Experiments—A Case Study Approach (Wiley 2011, ISBN-13: 978-0470744611) pp. 69, 70, 95, 135, and 136.
Skeren et al: "Design and visualization of synthetic holograms for security applications", 9th International Symposium on Display Holography, Journal of Physics: Conference Series 415 (IOP Publishing, 2013, XP020239069) pp. 1 to 7.
Tikhonravov et al: "Modern design tools and a new paradigm in optical coating design", Applied Optics, vol. 51, No. 30 (Optical Society of America, 2012, XP001578915) pp. 7319-7332.

* cited by examiner

Fig.3
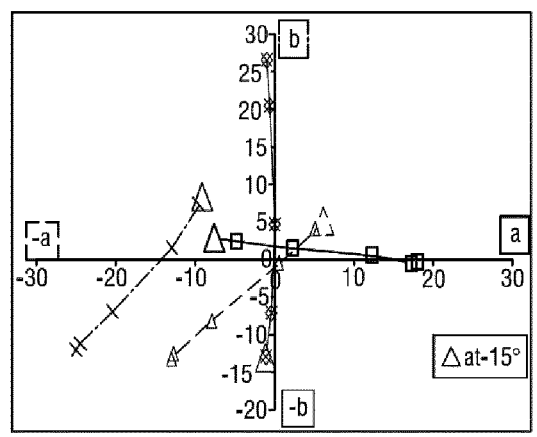
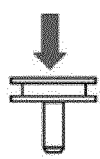 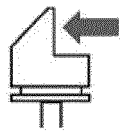 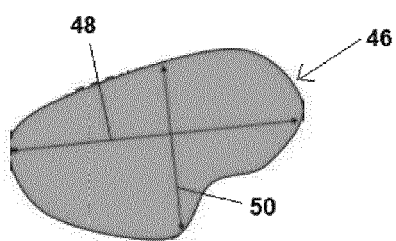
Fig. 4a   Fig. 4b        Fig. 4c

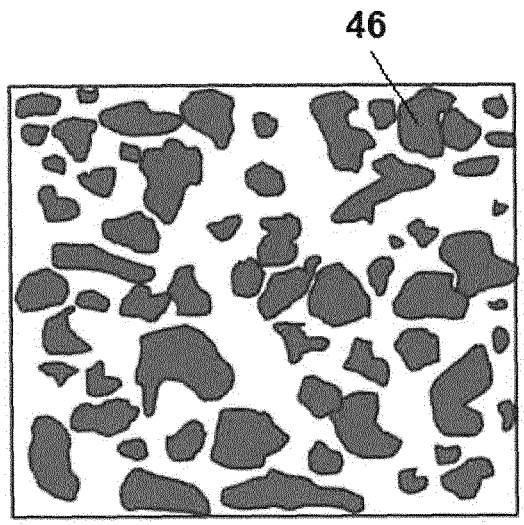
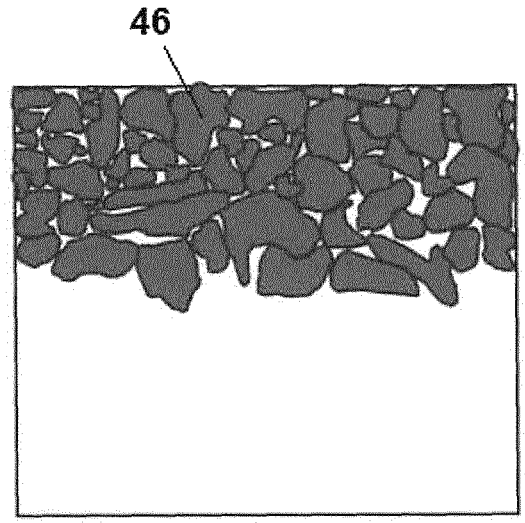
Fig. 5a     Fig. 5b
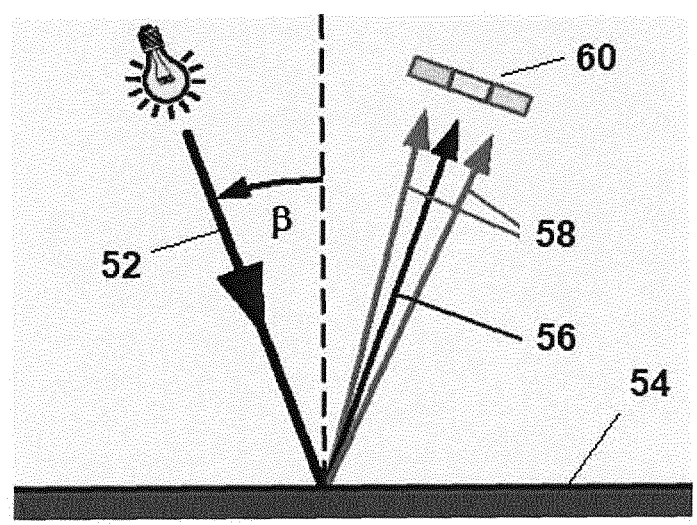
Fig. 6

METHOD FOR DETERMINING THE COMPOSITION OF A MULTI-LAYER SYSTEM SHOWING A PREDETERMINED COLOUR FLIP-FLOP EFFECT

The present invention relates to a method for determining the composition of a multi-layer system showing a predetermined colour flip-flop effect, such as a system comprising a substrate being coated with layers of inks, films, coatings or lacquers, wherein the multi-layer system exhibits a colour flip-flop effect, even if the multi-layer system does not contain any interference pigment.

Systems, such as objects or substrates, respectively, coated for instance with inks, wherein the inks impart a colour flip-flop effect, show a change of a colouristic property under different viewing angles or observation angles, respectively. Such effects are called flop effects or flip-flop effects, respectively. The colouristic property, which changes under different observation angles, may be the brightness and/or colour shade of the ink. More specifically, a change of the brightness of a printed object in dependency of the observation angle is typically called brightness flip-flop effect, whereas a change of the colour shade of a printed object in dependency of the observation angle is referred to as colour shade flip-flop effect or colour travel effect.

Inks imparting an object coated therewith with such a flip-flop effect are for instance interesting for coating objects used for safety applications, such as for forgery-proof security papers, such as banknotes, credit cards, postage stamps, telephone cards and identity cards, high quality packagings, medical packagings, and so on, whereas lacquers imparting an object coated therewith with such a flip-flop effect are for instance interesting for coating automobiles, furniture or architectural surfaces, in order to impart them a specific outer appearance.

In order to impart to a system a colour shade flip-flop effect, holographic foils are often used. For the same purpose, also usually interference pigments are added into the ink, coating, lacquer or film, respectively. Such interference pigments comprise at least two different layers, which cause a reflection of parts of the light waves at different planes and a refraction of a part of the light waves, so that the light waves reflected from the different planes travel different distances leading to an interference. Interference is a phenomenon in which two waves superpose to form a resultant wave of greater, lower or the same amplitude. Interference usually refers to the interaction of waves that are correlated or coherent with each other, either because they come from the same source or because they have the same or nearly the same frequency. Interference effects can be observed with all types of waves, for example, light, radio, acoustic, surface water waves or matter waves. Examples for such interference pigments are for instance carrier platelets, such as alumina platelets or silica platelets, which are coated with high-refractive metal oxides, such as with titanium dioxide and iron(III)oxide.

U.S. Pat. No. 7,077,897 B2 describes a multilayer interference pigment for security applications, which consists of a transparent support material which is coated with alternating layers of colourless, non-absorbent metal oxides of high and low refractive indices, with the difference between the refractive indices being at least 0.1. The respective pigment is obtainable by alternate coating of the transparent support material with a metal oxide of high refractive index and a metal oxide of low refractive index by a wet process by hydrolysis of the corresponding, water-soluble, inorganic metal compounds, and separating off, drying and optionally calcining the resultant pigment.

However, known systems based on interference pigments are expensive due to the complex structure of the interference pigments and the laborious production process for synthesizing the interference pigments. Another important disadvantage of known systems based on interference pigments is that each of these systems can only be used for one specific colour shade flip-flop, for example red-green.

Moreover, the kind of colour shade flip-flop is predetermined by the kind of interference pigment used. In other words, it is not possible to specify a desired flip-flop effect and then determine a recipe for a multi-layer system showing the desired flip-flop effect. Rather, the options for the flip-flop effect are limited by the specific available interference pigments.

In view of this, the object underlying the present invention is to provide a method, which allows to determine the composition of a multi-layer system showing a predetermined colour flip-flop effect, which may, but not necessarily require the presence of an interference pigment.

In accordance with the present invention, this object is satisfied by providing a method for determining the composition of a multi-layer system showing a predetermined colour flip-flop effect, wherein the multi-layer system comprises from bottom to top a) a substrate, b) at least one first colour layer containing a colourant, which is arranged on the substrate a), c) on the at least one first colour layer an effect layer containing at least one platelet-shaped effect pigment, and d) on the effect layer c) at least one second colour layer containing a colourant, wherein each of the at least one first colour layer and of the at least one second colour layer contains a colourant being no platelet-shaped effect pigment, wherein the method comprises the following steps:

i) specifying a first target value for the colour shade and/or colour brightness of the top side of the multi-layer system seen at a first observation angle, ii) specifying a second target value for the colour shade and/or colour brightness of the top side of the multi-layer system seen at a second observation angle, wherein the second observation angle is different from the first observation angle, and wherein the second target value is different from the first target value, iii) specifying a colourant system comprising at least one colourant and further comprising one effect pigment layer recipe being suitable for forming the effect layer c), iv) providing at least one empirical model of the relationship between the colour shades and/or colour brightness at at least two different observation angles comprising at least the first observation angle and the second observation angle specified in step ii) of the top side of a first number of multilayer systems, at least 90% of which comprising at least one first colour layer b) having at least one colourant as specified in step iii), at least one second colour layer d) having at least one colourant as specified in step iii) and an effect layer c) made of the effect pigment layer recipe specified in step iii), and v) optionally determining—making use of the at least one empirical model provided in step iv)—the composition of a multi-layer system having within a predetermined tolerance the first target value specified in step i) and the second target value specified in step ii), or, if none is found, specifying a new tolerance for the first target value specified in step i) and/or the second target value specified in step ii) and repeating steps iii) to v), or specifying in steps i) and ii) a new first target value and/or new the second target value and repeating steps iii) to v), or repeating the method by specifying in step iii) a different colourant system, which preferably covers more different colourants than the colourant system used before, wherein the determination in step v) is performed by using a computer program.

This solution uses the surprising finding that by arranging an effect layer c) containing at least one platelet-shaped effect pigment being composed of particles between one or more first colour layer(s) b) containing a colourant, such as a dye and/or pigment, being no platelet-shaped effect pigment and one or more second colour layer(s) d) containing a colourant, such as a dye and/or pigment, being no platelet-shaped effect pigment, a multi-layer system, such as an ink system, a coatings or lacquer system, or a film/foil system, is obtainable, which shows a colour shade flip-flop effect, i.e. which shows a change of the colour shade in dependency of the observation angle, and/or which shows a brightness flip-flop effect, i.e. which shows a change of the brightness in dependency of the observation angle, even if no interference pigments at all are included in the multi-layer system. Moreover, the solution of the present invention bases on the surprising finding that it is possible by using a statistical approach to reliably determine the composition of such a multi-layer system, which shows a desired, predetermined colour flip-flop effect. More specifically, the statistical approach merely requires to specify a colourant system comprising at least one colourant and further comprising one effect pigment layer recipe being suitable for forming the effect layer c), to provide at least one empirical model of the relationship between the colour shades and/or colour brightness at at least two different observation angles comprising at least the first observation angle and the second observation angle of the top side of a first number of multi-layer systems, and further parameters like e.g. the colourant sequence, to determine—making use of the at least one empirical model provided in step iv)—the composition of a multi-layer system.

"A and/or B" means in accordance with the present invention that either a) A is fulfilled or b) B is fulfilled or c) A and B are fulfilled. Thus, specifying a first/second target value for the colour shade and/or colour brightness of the top side of the multi-layer system seen at a first observation angle in steps i) and ii) means that either a) a first/second target value for the colour shade of the top side of the multilayer system is specified or b) a first/second target value for the colour brightness of the top side of the multi-layer system is specified or c) a first/second target value for the colour shade of the top side of the multi-layer system and a first/second target value for the colour brightness of the top side of the multi-layer system are specified. The same applies analogous to steps ii) and iv). Likewise, in step v) specifying a new tolerance for the first target value specified in step i) and/or the second target value specified in step ii) means either a) specifying a new tolerance for the first target value specified in step i) or b) specifying a new tolerance for the second target value specified in step ii) or iii) specifying a new tolerance for the first target value specified in step i) and specifying a new tolerance for the second target value specified in step ii).

In accordance with the present invention the determination in step v) is performed by using a computer program. Preferably, the computer program is able to make prognoses also for those multi-layer systems in the experimental region for which no experimental results have been obtained, by making use of the at least one empirical model obtained in step iv). These prognoses can also be presented in tabular form. Thus, in step v) the composition of a multi-layer system having within a predetermined tolerance the first target value specified in step i) and the second target value specified in step ii) is determined. If none such composition is found, either α) a new tolerance for the first target value specified in step i) and/or the second target value specified in step ii) is specified or β) in steps i) and ii) a new first target value and/or a new second target value is specified or γ) the method is repeated by specifying in step iii) a different colourant system, which preferably covers more different colourants than the colourant system used before.

This determination in step v) may be performed by using a statistics program or by using a spreadsheet software as the computer program.

The determination in step v) is performed in a first particular preferred variant of the present invention by using a statistics program for a direct calculation of experimental settings that leads within a predetermined tolerance to the desired first target value specified in step i) and the second target value specified in step ii). The user may then easily prepare the multi-layer system with the desired flip-flop effect by preparing the multi-layer system comprising from bottom to top a) the substrate, b) on the substrate a) the at least one first colour layer containing a colourant, c) on the at least one first colour layer b) the effect layer containing at least one platelet-shaped effect pigment, and d) on the effect layer c) the at least one second colour layer containing a colourant of the multi-layer system having been calculated by the statistics program.

Alternatively, in a second particular preferred variant of the present invention the determination in step v) is performed by calculating—making use of the at least one empirical model provided in step iv)—a prognosis for the values of the colour shades and/or colour brightness at at least two different observation angles comprising at least the first observation angle and the second observation angle specified in steps i) and ii) of the top side of a second number of multi-layer systems, at least 90% of which comprising at least one first colour layer having at least one colourant as specified in step iii), at least one second colour layer having at least one colourant as specified in step iii) and an effect layer made of the effect pigment layer recipe specified in step iii), wherein the second number is higher than the first number, and by searching the prognosis, whether at least one of the second number of multi-layer systems of the prognosis comprises a multi-layer system having within a predetermined tolerance the first target value specified in step i) and the second target value specified in step ii). Based on the one or more empirical model, the prognosis may be calculated by making use of a statistic program, by making use of a spreadsheet software or by making use of a statistic program and of a spreadsheet software. In other words, the prognosis creates calculated data for multi-layer systems, that have not been investigated in the experiments, by using the at least one empirical model provided step iv) with the first number of multi-layer systems. Therefore, the first number of multi-layer systems is referring to the number of multi-layer systems that have been investigated in experiments, whereas the second number is referring to either calculated prognosis data or the data of the combined experimentally investigated and calculated multi-layer systems. If one or more multi-layer system having within a predetermined tolerance the first target value and the second target value are comprised in the prognosis, the user may select at least one of these multi-layer systems. He may then easily prepare the multi-layer system with the desired flipflop effect by preparing the multi-layer system comprising from bottom to top a) the substrate, b) on the substrate a) the at least one first colour layer containing a colourant, c) on the at least one first colour layer b) the effect layer containing at least one platelet-shaped effect pigment, and d) on the effect layer c) the at least one second colour layer containing a colourant of the multi-layer system having been selected from the prognosis using the application parameters and layer coverages as well as other details as included in the respective dataset of the selected multi-layer system of the prognosis resulting from the respective at least one empirical model. If the prognosis does not comprise any multi-layer system having within a predetermined tolerance the first target value and the second target value, the user may specify a new, broader tolerance for the first target value specified in step i) and/or the second target value specified in step ii), or, alternatively, he may specify in steps i) and ii) a new first target value and/or a new second target value, or, still alternatively, he may repeat the method with a different colourant system, which preferably covers more different colourants than the colourant system used before. All in all, the method in accordance with the present invention allows to reliably determine the composition of a multi-layer system showing a predetermined colour flip-flop effect, which may, but not necessarily require the presence of an interference pigment.

The term "composition of a multi-layer system showing a predetermined colour flip-flop effect" means in accordance with the present invention the arrangement of the multi-layer system, i.e. the kind of substrate, the number of first and second colour layers, the colour shades and brightness or the recipes of each of the first and second colour layers, the recipe of the effect layer, the kind and recipe of any optional further layer and the coverages of each layer. Recipe means in this connection the composition of for instance the first colour layer, i.e. colourant formulation, from which the first colour layer is made.

Moreover, the term layer coverage means the sum of the area of the surface of a substrate or lower layer, respectively, which is covered by an upper layer, divided by the total area of the longitudinal section of the substrate or lower layer, respectively. Likewise, the term ink coverage means the sum of the area of the surface of a substrate or lower layer, respectively, which is covered by the ink (layer), divided by the total area of the longitudinal section of the substrate or lower layer, respectively.

In addition, the term "colourant" means in accordance with the present invention a compound or mixture containing one or more colouring substances, such as pigment(s) and/or dye(s). The "colourant" may be a printing ink, a coating, a lacquer, a foil or a film. Alternatively, the "colourant" may be a semi-finished product, in which the colouring substance(s), such as pigment(s) and/or dye(s), is/are dispersed in a solvent, binder(s), solvent mixture(s), or solvent-binder mixtures, respectively. Such a semi-finished product is usually mixed with a non-colouring varnish, that usually contains one or more binders, such as alkyd resin, and one or more solvents, such as mineral oil or vegetable oil, and additives, such as defoamers, stabilizers, wetting agents, adhesion promoters, hardeners, photoinitiators, and the like.

Furthermore, an empirical model means in accordance with the present invention, as generally defined in this field, any kind of (computer) approximation of empirical observations by a mathematical equation. In general, each observable needs a separate mathematical equation, wherein each of the mathematical equations defines a separate empirical model. Thus, empirical modelling is a generic term for activities that create models by observation and experiment. Empirical models are in detail defined and described in George E. P. Box, J. Stuart Hunter, William G. Hunter, "Statistics for Experimenters", Wiley 2005, ISBN-13: 978-0471718130, by George E. P. Box, Norman R. Draper: "Empirical Model-Building and Response Surfaces", Wiley 1987, ISBN-13: 978-0471810339, and by Peter Goos, Bradley Jones: "Optimal Design of Experiments—A Case Study Approach", Wiley 2011, ISBN-13: 978-0470744611. Preferably, the at least one empirical model is obtained by using a statistics program.

The multi-layer system may be any kind of system, such as an ink system, a lacquer system, a coatings system or a film/foil system.

Principally, the first and second target values may be specified in steps i) and ii) in any form, which allows to precisely specify the colour shade and brightness of a specific colour shade. Good results are in particular obtained, when values of a colour space are used, wherein the colour space may be the RGB-colour space, the CMY colour space, the CMYK colour space, the CIELUV colour space, the CIE-LCh colour space or the CIELab colour space.

In accordance with a particular preferred embodiment of the present invention, wherein the first and second target values are specified in steps i) and ii) as L*-, a*-, b*-values of the CIELab colour space and/or as L*-, C*- and h°-values of the CIE-HCL colour space.

As set out above, the colour flip-flop effect may be a colour shade flip-flop effect and/or a colour brightness flip-flop effect. Preferably, the colour flip-flop effect is a colour shade flip-flop effect so that in step i) a first target value for a first colour shade and in step ii) a second target value for a second colour shade are specified, wherein the first and second colour shades are different from each other.

The colour travel can be calculated with the colour data measured at different viewing angles. For this calculation the measured a and b values that refer to the L*a*b* colour space (CIELAB) can be used. The L*a*b* colour space describes mathematically all perceivable colours in the three dimensions L* for lightness and a* and b* for the colour opponents green-red and blue-yellow. The colour travel can be described as the distance delta a/b between measurements at different viewing angles. Another suitable colour space for investigation of colour travel is the HCL (Hue-Chroma-Luminescence) colour space. HCL uses the CIELAB model defined by the International Commission on Illumination (CIE) in 1976, translated into polar coordinates. The L* axis is the same as in the CIELAB system, but a* and b* are transformed into polar coordinates, where the distance from zero is the Chroma C* and the angle is the hue h° or colour shade. In this colour space the delta values of hue and Chroma, respectively, can be reviewed to describe the colour travel. Subsequently, the * is sometimes omitted.

In a further development of the idea of the present invention, it is proposed that the delta a/b of the colour shade flip-flop effect, i.e. the delta a/b between the first and the second target value, is at least 15, when 15° and 110° are chosen as first and second viewing angle. The delta a/b is determined according to the equation delta $a/b = ((a[15°] - a[110°])^2 + (b[15°] - b[110°])^2)^{1/2}$, wherein $a[15°]$ is the a-value of the top side of the multi-layer system measured at a first observation angle of 15°, $a[110°]$ is the a-value of the top side of the multi-layer system measured at a second observation angle of 110°, $b[15°]$ is the b-value of the top side of the multi-layer system measured at the first observation angle of 15° and $b[110°]$ is the b-value of the top side of the multi-layer system measured at the second observation angle of 110°, wherein the measurement is performed by irradiating in a dark environment a standardized light type onto the top side of the multi-layer system at an angle of incident of 45° with respect to the horizontal direction and measuring the a-values of the top side of the multi-layer system at observation values of 15° and 110° and measuring the b-values of the top side of the multi-layer system at observation values of 15° and 110°, wherein the angle of reflection of 135° with respect to the horizontal direction is defined as an observation angle of 0°. As standardized light visual light or other standardized light types can be used, e.g. A, C, D50, D65, F2, F7, F11 or F12, wherein D50 is particularly preferred. The higher the numeric value of delta a/b, the higher the flip-flop effect. Preferably, the delta a/b measured as set out above is at least 30 and more preferably at least 38. In the above embodiment, the delta a/b between the measurements at 15° and 110° was chosen as a means to describe the colour travel. However, in other embodiments other angles might also be suitable to describe the flip-flop effect, resulting perhaps in lower delta a/b values.

In accordance with another embodiment of the present invention, the colour flipflop effect is a colour brightness flip-flop effect so that in step i) a first target value for the ratio of a-/b-value of a colour shade and a first brightness and in step ii) the same ratio of a-/b-value and a second brightness are specified, wherein the first and second colour brightness are different from each other.

Preferably, the delta L is in this embodiment, i.e. the delta L between the first and the second target value, at least 10, wherein the delta L is determined according to the equation delta $L=|L[15°]-L[110°]|$ with $|L[15°]-L[110°]|$ meaning the absolute difference of both values, wherein $L[15°]$ is the L-value of the top side of the multilayer system measured at a first observation angle of 15° and $L[110°]$ is the L-value of the top side of the multi-layer system measured at a second observation angle of 110°, wherein the measurement is performed by irradiating in a dark environment a standardized light type onto the multi-layer system at an angle of incident of 45° with respect to the horizontal direction and measuring the L-values of the top side of the multi-layer system (10) at observation values of 15° and 110°, wherein the angle of reflection of 135° with respect to the horizontal direction is defined as an observation angle of 0°. Also in this embodiment, as standardized light visual light or other standardized light types can be used, e.g. A, C, D50, D65, F2, F7, F11 or F12, wherein D50 is particularly preferred. Preferably, the delta L is at least 20 and more preferably at least 30.

In accordance with still another embodiment of the present invention, the colour flip-flop effect is a colour shade and a colour brightness flip-flop effect so that in step i) a first target value for a first colour shade and a first brightness and in step ii) a second target value for a second colour shade and a second brightness are specified, wherein the first and second colour shades are different from each other and wherein the first and second colour brightness are different from each other.

Preferably, in this embodiment the delta a/b of the colour shade flip-flop effect is at least 15 and the delta L is at least 10.

Alternatively to the aforementioned delta a/b and/or delta L, or in addition to the aforementioned delta a/b and/or delta L, the multi-layer system in accordance with the present invention may have a delta h° of at least 15, wherein the delta h° is determined according to the equation delta $h°=|h°[15°]-h°[110°]|$ with $|h°[15°]-h°[110°]|$ meaning the absolute difference of both values when $|h°[15°]-h°[110°]|$ is ≤180 or delta $h°=360-|h°[15°]-h°[110°]|$ when $-|h°[15°]-h°[110°]|$ is >180, wherein $h°[15°]$ is the h°-value of the HCL colour space measured at a first observation value of 15° and $h°[110°]$ is the h°-value measured at a second observation value of 110°, wherein the measurement is performed by irradiating in a dark environment a standardized light type onto the multi-layer system at an angle of incident of 45° with respect to the horizontal direction and measuring the h°-values of the top side of the multi-layer system (10) at observation values of 15° and 110°, wherein the angle of reflection of 135° with respect to the horizontal direction is defined as an observation angle of 0°. Preferably, the delta h° is at least 30.

In accordance with the present invention, the multi-layer system comprises from bottom to top a substrate a), at least one first colour layer b) containing a colourant, which is arranged on the substrate a), on the at least one first colour layer an effect layer c) containing at least one platelet-shaped effect pigment, and on the effect layer at least one second colour layer d) containing a colourant. The recipe forming the effect layer c) as well as the colourants used in the at least one first colour layer b) and in the at least one second colour layer d) are specified in step iii) so that the at least one empirical model and optionally the prognosis calculated from the at least one empirical model are based on the effect layer c) and the colourants used in the first and second colour layers b) and d).

It is a particular important feature of the present invention that the effect layer c) containing at least one platelet-shaped effect pigment is arranged between the at least one first colour layer b) and the at least one second colour layer d). An effect pigment is defined to be composed of platelet-shaped effect pigment particles, which are able to reflect incident light but which preferably do not exhibit any colour shade flip-flop effect. It is particularly preferred that the effect pigment is not at all an interference pigment. Interference pigments are typically composed of thin, highly refractive layers, which produce an interference of light waves.

In principle, the present invention is not specifically limited to the kind of effect pigment which is included in the effect layer c), as long as it reflects incident light in a sufficient amount. Preferably, the effect pigment is selected from the group consisting of metal or a mineral. Suitable examples therefore are pigments being composed of silver, gold, aluminium, alloys, such as brass bronzes, copper-zinc alloys and aluminium bronzes, mica, metal oxide doped alpha-iron oxides, such as manganese doped alpha-iron oxides, aluminium oxide doped alpha-iron oxides and silicon dioxide doped alpha-iron oxides, and arbitrary combinations of two or more of the aforementioned substances. More preferably, the effect pigment contained in the effect layer recipe is a metallic effect pigment, i.e. an effect pigment composed of metal.

Most preferably, the platelet-shaped effect pigment included in the effect layer recipe is a platelet-shaped metallic pigment being composed of particles made of a metal selected from the group consisting of silver, gold, aluminium, copper, brass bronzes, copper-zinc alloys or other alloys, such as Stapa AE 8 NL/80 Aluminium, Metalstar 07 0095 Silver, Aluminium Stapa AE Reflexal VIII/80, Stapa Reflexal 88 NL/80, Metalstar 06 7000 Silver, Rotoflex XA 6-203 Bleichgold, Rotoflex XA 6-206 Reichbleichgold, Rotoflex XA 6-209 Reichgold, RotoVario 530080 Silver, Rotovario 500 042 Silver, Rotovario 500022 Silber, Hydro Pellet 1300, Rotovario 500001 Silber from Eckart, or Decomet 1010/10, Grandor 4140 Reichgold, Grandor 4140 Reichbleichgold, Grandor 4140 Bleichgold from Schlenk, or Silvet ET 2016 from Silberline and arbitrary combinations of two or more of the aforementioned substances.

In addition to the effect pigment, the effect layer recipe can also contain one or more non-effect pigments or dyes.

In accordance with the present invention, the platelet-shaped effect pigment is preferably an effect pigment having an average length of 2 to 500 µm, an average width of 2 to 500 µm and an average thickness of at most 1 µm. Particular good results are obtained, when the platelet-shaped effect pigment is composed of particles having an average length of 2 to 40 µm and more preferably of 2 to 20 µm or of 2 to 500 µm and more preferably of 2 to 100 µm. The particle length is defined in this connection as the longest extension of the particle, whereas average particle length means the average of the lengths of at least 600 measured particles and preferably of at least 1,000 measured particles. For instance, 1,000 of the platelet-shaped effect pigment particles are optically characterized, whereby the lengths of the 1,000 particles are determined. Then, the sum of the 1,000 lengths is calculated, which is divided by 1,000.

If the multi-layer system is prepared by a printing technique, i.e. if the layers of the multi-layer system are ink layers, the average length of the platelet-shaped effect pigment particles is preferably 2 to 40 µm and more preferably 2 to 20 µm. If the multi-layer system is prepared by e.g. a spraying technique, i.e. if the layers of the multi-layer system are coating or lacquer layers, the average length of the platelet-shaped effect pigment particles is preferably 2 to 500 µm and more preferably 2 to 100 µm. The same is preferred when the multi-layer system is a hybrid multi-layer system, in which one or more, but not all of the layers are ink layers, whereas the other layers including at least the effect layer c) are coating or lacquer layers. If the multi-layer system is prepared by laminating foils or films, i.e. if the layers of the multi-layer system are foil or film layers, the average length of the platelet-shaped effect pigment particles is preferably 2 to 40 µm and more preferably 2 to 20 µm in the respective foil or film layer. Foils are meant in accordance with the present invention to be aluminium foils, whereas films are meant to be plastic films.

In accordance with a further preferred embodiment of the present invention, the platelet-shaped effect pigment is composed of particles having an average width of 2 to 40 µm and more preferably of 2 to 20 µm or of 2 to 500 µm and more preferably of 2 to 100 µm. The particle width is defined in this connection as the longest extension of the particle in the direction being perpendicular to the particle length, whereas average particle width means the average of the widths of at least 600 measured particles and preferably of at least 1,000 measured particles.

If the multi-layer system is prepared by a printing technique, i.e. if the layers of the multi-layer system are ink layers, the average width of the platelet-shaped effect pigment particles is preferably 2 to 40 µm and more preferably 2 to 20 µm. If the multi-layer system is prepared by e.g. a spraying technique, i.e. if the layers of the multi-layer system are coatings or lacquer layers, the average width of the platelet-shaped effect pigment particles is preferably 2 to 500 µm and more preferably 2 to 100 µm. The same is preferred when the multi-layer system is a hybrid multi-layer system, in which one or more, but not all of the layers are ink layers, whereas the other layers including at least the effect layer c) are selected from the group consisting of coating and lacquer layers. If the multi-layer system is prepared by laminating foils or film, i.e. if the layers of the multi-layer system are foil or film layers, the average width of the platelet-shaped effect pigment particles is preferably 2 to 40 µm and more preferably 2 to 20 µm.

The length and width of particles in general and specifically of platelet-shaped effect pigment particles are measured in accordance with the present invention preferably as follows: For sample preparation, the pigment particles are washed out with acetone, then a few drops of the dispersion of pigment particles in acetone are applied to e.g. a PMMA (polymethyl methacrylate) or glass pane or a mica substrate fixed on a turntable and dried at room temperature. In this way, most of the pigment particles orient themselves parallel to the surface of the substrate. By choosing an appropriate dilution factor, an overlapping of single pigments on the substrate can be avoided and the length and width of the individual pigments can be determined optically. The length and width is then determined optically, preferably by means of scanning electron microscopy, which is performed with a Phenom Pro XL from Thermo Fisher Scientific, Phenom World BV, Eindhoven, The Netherlands, in the measurement modus BSE (back scattered electrons) using a voltage of 15 kV and using a beam current of 1,7 Nanoampere. The particle lengths and widths are then analyzed from the obtained images with the software tool "ParticleMetric" which is included in the software ProSuite distributed by Phenom-World BV, Eindhoven, The Netherlands. More specifically, the images are preferably enlarged so that 20 to 80 particles may be examined. Then the particle length and width are determined for single particles. In order to calculate the average length and width, respectively, as set out above at least 600 and preferably of at least 1,000 particles are measured, then the sum of the measured lengths and width, respectively, is calculated, which is divided by the number of measured particles.

The platelet-shaped effect pigment particles may have a regular cross-sectional form, such as a circular cross-sectional form. However, the platelet-shaped effect pigment particles may have a regular or any irregular cross-sectional form. Irrespective of whether the platelet-shaped effect pigment particles have a regular or irregular cross-sectional form, according to the present invention they may be further characterized by a calculated average diameter. More specifically, the average diameter is calculated according the equation (L+W)/2, in which L is the average length of the particles and W is the average width of the particles. Preferably, the average diameter of the platelet-shaped effect pigment particles is 2 to 500 µm, more preferably 2 to 40 µm and even more preferably of 2 to 20 µm or 2 to 500 µm and more preferably of 2 to 100 µm, such as 2 to 100 µm or 2 to 50 µm. If the multi-layer system is prepared by a printing technique, i.e. if the layers of the multi-layer system are ink layers, the average diameter of the platelet-shaped effect pigment particles is preferably 2 to 40 µm and more preferably 2 to 20 µm. If the multi-layer system is prepared by e.g. a spraying technique, i.e. if the layers of the multi-layer system are coating or lacquer layers, the average diameter of the platelet-shaped effect pigment particles is preferably 2 to 500 µm and more preferably 2 to 100 µm. The same is preferred when the multi-layer system is a hybrid multi-layer system, in which one or more, but not all of the layers are ink layers, whereas the other layers including at least the effect layer c) are selected from the group consisting of coating, lacquer, film and foil layers. If the multi-layer system is prepared by laminating foils or films, i.e. if the layers of the multi-layer system are foil or film layers, the average diameter of the platelet-shaped effect pigment particles is preferably 2 to 40 µm and more preferably 2 to 20 µm.

In a further development of the idea of the present invention, it is proposed that the at least one platelet-shaped effect pigment is composed of particles having an average thickness of 0.01 to at most 1 µm, more preferably of 0.05 to 1 µm and even more preferably of 0.05 to 0.5 µm, in particular when the multi-layer system is composed of inks. When the multi-layer system is composed of coatings or lacquers, it is proposed that the at least one platelet shaped effect pigment is composed of particles having an average thickness of 0.01 to 1 µm. The same is preferred when the multi-layer system is a hybrid multi-layer system, in which one or more, but not all of the layers are ink layers, whereas the other layers including at least the effect layer c) are coating or lacquer layers. The particle thickness is defined in this connection as the shortest extension of the particle in the direction being perpendicular to the two-dimensional plane being defined by the particle length and the particle width, whereas average particle thickness means the average of the thicknesses of at least 600 measured particles and preferably of at least 1,000 measured particles. These numbers for the particle thickness apply to all multi-layer systems based on inks, coatings, lacquers, films and foils.

The thickness of particles in general and specifically of platelet-shaped effect pigment particles is measured in accordance with the present invention preferably as follows: A resin commonly used in electron microscopy, for example TEMPFIX distributed by Gerhard Neubauer Chemikalien, Münster, Germany, is applied to a sample plate and heated on a heating plate until softened. Subsequently, the sample plate is removed from the heating plate and the respective pigment particles are sprinkled or spread onto the softened resin. The resin becomes solid again as it cools and the pigment particles arrange—due to the interplay between adhesion and gravity—almost vertically and are fixed on the sample plate. This makes it easy to measure the pigments laterally in the electron microscope. The resulting sample is placed on a sample holder and scanning electron microscopy is performed with a Phenom Pro XL from Thermo Fisher Scientific, Phenom World BV, Eindhoven, The Netherlands, in the measurement modus BSE (back scattered electrons) using a voltage of 15 kV and using a beam current of 1,7 Nanoampere. The particle thicknesses are then analyzed from the obtained images with the software tool "ParticleMetric" which is included in the software ProSuite distributed by Phenom-World BV, Eindhoven, The Netherlands. More specifically, the images are preferably enlarged so that 20 to 80 particles may be examined. Then the thickness of the particles is determined for single particles. When determining the thickness, the azimuthal angle α of the pigment particle to a plane normal to the surface is estimated and is taken into account when evaluating the thickness according to the formula $T_{eff}$ of $=T_{mess}/\cos \alpha$, in which T is the particle thickness. For determining the average thickness, as set out above, the thicknesses of at least 600 measured particles and preferably of at least 1,000 measured particles are measured, the obtained values are summarized and the sum is divided by the number of evaluated particles.

The length, width and thickness of the particles in the final layer multi-layer system may be determined accordingly. More specifically, several sample pieces having each for instance an area of about 1 cm$^2$ may be cut out of the multi-layer system for example with a laser. The samples may be embedded in a resin common for electron microscopy, such as embedding media like epoxy resins, e.g. Araldite 502 or 6005, supplied by Electron Microscopy Sciences, Hatfield, Pennsylvania. Thereafter, one or more microtome longitudinal sections of the layer of the multi-layer system to be analyzed and/or one or more microtome cross-sections of the layer of the multi-layer system to be analyzed may be made, each of the sections having for instance a thickness of 5 mm. The microtome section(s) may be prepared for instance by using a motorized commercial rotary microtome of type RM 2155 available from Leica Mikrosysteme, Bensheim, Germany. Prior to sectioning, the desired thickness is set and then, the respective metal panels are fixed and in the actual operational step, the rotary microtome is run over the respective sample. Subsequently, the sample(s) are fixed on a sample holder. With each of the resulting thin sections scanning electron microscopy is performed and the particle length, particle width, particle thickness, average particle length, average particle width and average particle thickness are determined as described above.

In accordance with a further preferred embodiment of the present invention, the at least one platelet-shaped effect pigment is composed of particles having a first aspect ratio of the average particle length divided by the average particle width of 1 to 20 and preferably of 1 to 2 or of 2 to 5. These numeric value ranges are preferred for all multi-layer systems, i.e. for inks, coatings, lacquers, and films.

In addition, it is preferred that the at least one platelet-shaped effect pigment is composed of particles having a second aspect ratio of the average particle length divided by the average particle thickness of 1 to 75,000, preferably of 1 to 1,000, more preferably of 1 to 200, even more preferably of 1 to 100 and most preferably of 1 to 60. Such metal effect pigments are mostly oriented so that their two-dimensional plane being defined by the particle length and the particle width is oriented basically parallel to the longitudinal section of the effect layer.

It is proposed in a further development of the idea of the present invention that the average particle area ratio of the effect layer c) is 5 to 75%, more preferably 10 to 55% and most preferably 15 to 35%. The average particle area ratio of the effect layer c) means in accordance with the present invention the sum of the area in the longitudinal section of the effect layer c) which is covered by the platelet-shaped effect pigment particles divided by the total area of the longitudinal section of the effect layer. The measurement of the average particle area ratio of the effect layer c) is illustrated below with regard to FIG. 5.

The average particle area ratio of any of the single layers and particularly of the effect layer is measured in accordance with the present invention preferably by scanning electron microscopy from the surface of the concerned layer of the multilayer system being prepared as described above or from a longitudinal section of the concerned layer of the multi-layer system being prepared as described above.

The particles are coloured with the software tool "ParticleMetric" and then the sum of the area in the longitudinal section which is covered by particles is evaluated and divided by the total area of the longitudinal section analyzed by scanning electron microscopy so as to obtain the average particle area ratio in percent. Preferably, the effect layer recipe of the multi-layer system in accordance with the present invention contains, preferably in case it is an ink layer, a coating or a lacquer layer, depending on the effect layer thickness, the viscosity and the application method, 10 to 95% by weight of binder based on the total weight of the composition applied to form the effect layer, wherein the binder is preferably selected from the group consisting of polyesters, polyethers, polyurethanes, polyamides, polyacrylates, maleinate resins, collophonium resins, ketone resins, aldehyde resins, alkyd resins, collophonium modified phenolic resins, hydrocarbon resins, silicates, silicones, phenolic resins, urea resins, melamine resins, epoxy resins, polyterpene resins, shellac, copal, dammar, lignin derivatives, natural resins, polyvinylalcohols, polyvinylether, polyvinylacetates, polyvinylchloride, polyvinylethers, polyvinylpropionates, polyvinylbutyrates, polymethacrylates, polystyrenes, polyolefines, hydrocarbon resins, coumarone-indene resins, aromatic formaldehyde resins, carbamide acid resins, sulfonamide resins, chlorinated resins, nitrocellulose, CAB (cellulose acetate butyrate), CAP (cellulose acetate propionate), cellulose compounds, rubbers, polysaccharides, radiation curing resins, temperature curing resins and arbitrary combinations of two or more of the aforementioned binders.

In addition to the binder or instead of the binder, the effect layer recipe may contain, depending on the nature and the viscosity of the ink and the application method, more than 0 to 95% by weight of solvent based on the total weight of the composition applied to form the effect layer c). Good results are in particular obtained, when the solvent is selected from the group consisting of mineral oils, vegetable oils, fatty acid esters, alcohols, esters, ethers, glycols, water, cyclic or linear hydrocarbons, ketones, lactones, alkanes, aromatic hydrocarbons, monomers and oligomers with hydroxy, carboxy, alkoxy, amino, acrylic or vinyl functionality aromatic compounds and arbitrary combinations of two or more of the aforementioned solvents.

Furthermore, the effect layer recipe may contain one or more additives. Examples for such additives are those selected from the group consisting of rheological additives, adhesives, defoamers, slip additives, anti-corrosion additives, gloss additives, waxes, wetting agents, curing agents, chelating agents, photoinitiators, inhibitors, desiccants, stabilizers, emulsifiers, pH adjustment additives, abrasions resistance additives, plasticizers, antistatic additives, preservatives, light protection agents, matting agents, fillers and arbitrary combinations of two or more of the aforementioned additives.

It has been found within the present invention that the degree of the obtained flipflop effect of the multi-layer system is influenced, if the multi-layer system is an ink multi-layer system, by the ink coverage. If the multi-layer system is an ink multilayer system, it is preferred that the ink coverage of the dry effect layer c) on the at least one first colour layer b), i.e. on the uppermost of the first colour layer(s), is 25 to 100%, more preferably 40 to 100%, even more preferably 50 to 100% and most preferably 60 to 100%. The ink coverage is the percentage of the area of the uppermost of the first colour layer(s), which is covered by the effect layer c). Ink coverage refers to the real area coverage when halftones are printed. Likewise to this, it is preferred that the ink coverage of the dry effect layer c) on the substrate is 25 to 100%, more preferably 40 to 100%, even more preferably 50 to 100% and most preferably 60 to 100%.

If the multi-layer system is a lacquer multi-layer system, a coating, or a film/foil multi-layer system, the coverage of the effect layer c) on the at least one first colour layer b), i.e. on the uppermost of the first colour layer(s), is complete, i.e. 100% or at least 90%. Anyway, the effect layer c) completely covers the at least one first colour layer b). Likewise to this, it is preferred that the effect layer c) completely covers the substrate.

In a further development of the idea of the present invention, it is proposed that the grammage of the dry effect layer c) is 0.2 to 15 gsm, more preferably 0.3 to 10 gsm and most preferably 0.4 to 7,5 gsm, particularly when the multi-layer system is composed of inks. When the multi-layer system is a coatings or lacquer multilayer system, the dry laydown of the effect layer c) is 0.1 to 60 gsm and more preferably 1 to 30 gsm and even more preferably 1 to 20 gsm. The same is preferred when the multi-layer system is a hybrid multi-layer system, in which one or more, but not all of the layers are ink layers, whereas the other layers including at least the effect layer c) are coating, lacquer or film layers.

In addition, it is preferred that the weight ratio of pigment to binder in the dry effect layer is 0.02:1 to 2:1, more preferably 0.1 to 2:1 and even more preferably 0,2:1 to 1.8:1. More specifically, it is preferred that the weight ratio of pigment to binder in the dry effect layer c) is 0.3:1 to 2:1, more preferably 0.7:1 to 2:1 and most preferably 0.7:1 to 1.8:1, when the multi-layer system is composed of inks. When the multi-layer system is composed of lacquers or coatings, it is preferred that the weight ratio of pigment to binder in the dry effect layer c) is 0.02:1 to 2:1, more preferably 0.2:1 to 1.5:1 and most preferably 0.2:1 to 1:1. The same is preferred when the multi-layer system is a hybrid multi-layer system, in which one or more, but not all of the layers are ink layers, whereas the other layers including at least the effect layer c) are coating, lacquer or film/foil layers.

In a further development of the idea of the present invention, it is proposed that the effect layer recipe of the multi-layer system in accordance with the present invention is an ink, a coating, a laquer, or a film/foil multi-layer system, which contains 10 to 70% by weight, preferably 20 to 70% by weight, still preferably 30 to 70% by weight and more preferably 40 to 70% by weight of platelet-shaped effect pigment based on the total weight of the dry effect layer. When the multi-layer system is a coatings or lacquer multi-layer system, it is preferred that the effect layer contains 1 to 30% by weight and more preferably 2 to 25% by weight of platelet-shaped effect pigment based on the total weight of the dry effect layer. The same is preferred when the multi-layer system is a hybrid multi-layer system, in which one or more, but not all of the layers are ink layers, whereas the other layers including at least the effect layer c) are coating, lacquer or film/foil layers. It is particularly preferred that the effect layer c) comprises the aforementioned contents of platelet-shaped metallic effect pigment.

Furthermore, it is preferred that the effect layer c) of the multi-layer system in accordance with the present invention has a sum of reflectance and scattering of 20 to 100%, more preferably of 30 to 100% and most preferably of 40 to 100%.

The sum of reflectance and scattering of a layer, such as of the effect layer, is measured in accordance with the present invention preferably by using a HazeGloss instrument from Byk Gardner, Geretsried, Germany. A piece of the prepared layer with or without being attached to other layers and having for instance an area of 10 cm$^2$ is cut out of the multi-layer system and placed in the apparatus. Norm light D65 is irradiated in defined angle, e.g. 20°, 60° or 85° and preferably 20°, from the vertical direction onto the surface of the layer to be analyzed and the reflected (which corresponds to gloss, as described in DIN 67530) as well as the scattered light (which corresponds to haze) is detected.

In accordance with a particular preferred embodiment of the present invention, the effect pigment layer recipe does not contain any interference pigment.

In accordance with the present invention, in step iii) a colourant system is specified, which comprises at least two different and preferably at least three different colourants. The more colourants are included in the colourant system, the more different colour shades and/or colour brightness may be produced by appropriately arranging one or more first colour layers b) below and one or more second colour layers d) above the effect layer c), wherein each of the first and second colour layers are made of a colourant of the colourant system, if the colourant(s) of the colourant system is/are finished product(s), such as printing ink(s), coating(s), lacquer(s), foil(s) or film(s), or, wherein each of the first and second colour layers are made of a finished product including a non-colouring varnish and a colourant of the colourant system. Since these colourants of the colourant system specified in step iii) are actually used in the experiments on which the at least one empirical model bases, the at least one empirical model as well as the optional prognosis calculated therefrom cover the more different colour shades and/or colour brightness, the more colourants are included in the colourant system specified in step iii).

Preferably, in step iii) a colourant system is specified, which comprises at least three different colourants spanning a colour space covering at least 100,000, preferably at least 250,000, more preferably at least 500,000 and most preferably at least 1 million perceptual different colour shades being generable by applying a combination of one or more of the at least three different colourants above each other.

A particular suitable example is a colourant system, which comprises a cyan colourant, a magenta colourant and a yellow colourant. Even more perceptual different colour shades are covered, when the colourant system is a four-colourant system, such as one comprising a cyan colourant, a magenta colourant, a yellow colourant and a black colourant. It is obvious that even more perceptual different colour shades are covered, when the colourant system is a five-, six- or seven-colourant system, such as one comprising five, six or seven colourants selected from the group comprising a cyan colourant, a magenta colourant, a yellow colourant, a black colourant, an orange colourant, a green colourant and a violet colourant. Particular goods results are obtained with a seven-colourant system, such as one comprising a cyan colourant, a magenta colourant, a yellow colourant, a black colourant, an orange colourant, a green colourant and a violet colourant. Even more colour shades can be achieved using a colourant system that includes in addition yellowish red, bluish red, redish blue, greenish yellow, redish yellow, brown, and/or pink.

In accordance with the present invention, in step iv) at least one empirical model is provided. Preferably, the at least one empirical model is selected from the group consisting of linear models, of second order models, and of higher order models. A linear model includes only terms that are linear in the settings of the experimental factors or parameters, respectively, whereas a second order model includes interaction terms and quadratic terms as well.

In accordance with the present invention, at least 90%, preferably at least 95%, more preferably at least 99% and most preferably all of the multi-layer systems of the at least one empirical model provided in step iv) comprise at least one first colour layer b) having at least one colourant as specified in step iii), at least one second colour layer d) having at least one colourant as specified in step iii) and an effect layer c) made of the effect pigment layer recipe specified in step iii). Merely some few of the multi-layer systems of the at least one empirical model may lack one or more of the first colour layer b), the second colour layer d), the effect layer c) and the substrate a) so as to form marginal values of the at least one empirical mode.

It is proposed in a further development of the idea of the present invention that the at least one empirical model used in the method has been obtained by making use of a design of experiments. Design of experiment is a methodology for systematically planning and evaluating of experiments. More specifically, a design of experiments is a very efficient methodology for determining the functional relationship of influencing parameters and of the results. Good results are in particular obtained, when the design of experiments is selected from the group consisting of optimal designs of experiments, full factorial designs of experiments, fractional factorial designs of experiments, centrally composed experimental designs and combinations thereof. A full factorial design comprises all possible combinations of all settings of all factors or parameters, respectively. Optimal designs usually comprise a subset of a full factorial design, which is for example selected by means of an algorithm that maximizes the so-called information matrix (D-optimal). Other optimality criteria are described in statistical textbooks. Fractional factorial designs use half of the settings of a full factorial design, a quarter, an eighth or even a smaller part, selected in a way that the vectors of the design matrix are orthogonal. For more details see for example, George E. P. Box, J. Stuart Hunter, William G. Hunter: "Statistics for Experimenters", ISBN-13: 978-0471718130.

Preferably, the design of experiments used for obtaining the reference value(s) is a full factorial design of experiments, a fractional factorial design of experiments or an optimal design of experiments, such as an A-optimal design of experiments, a D-optimal design of experiments, an E-optimal design of experiments or a G-optimal design of experiments.

More preferably, the at least one empirical model has been obtained by making use of the results of a D-optimal design of experiments. D-optimal designs are very flexible and can be adopted to a large variety of situations. Moreover, they allow to use experimental capacity in a very efficient way.

Most preferably, the at least one empirical model provided in step iv) has been obtained by the use of at least one second order empirical model obtained by making use of the results of a D-optimal design of experiments.

In statistics, a full factorial experiment is an experiment whose design consists of two or more factors, each with discrete possible values or "levels", and whose experimental units take on all possible combinations of these levels across all such factors. Such an experiment allows the investigator to study the effect of each factor on the response variable, as well as the effects of interactions between factors on the response variable. If the number of combinations in a full factorial design is too high to be logistically feasible, a fractional factorial design may be done, in which some of the possible combinations (usually at least half) are omitted.

In statistics, fractional factorial designs are experimental designs consisting of a carefully chosen subset (fraction) of the experimental runs of a full factorial design. The subset is chosen so as to exploit the sparsity-of-effects principle to expose information about the most important features of the problem studied, while using a fraction of the effort of a full factorial design in terms of experimental runs and resources.

In the design of experiments, optimal designs (or optimum designs) are a class of experimental designs that are optimal with respect to some statistical criterion. The optimality of a design depends on the statistical model and is assessed with respect to a statistical criterion, which is related to the variance-matrix of the estimator. Specifying an appropriate model and specifying a suitable criterion function both require understanding of statistical theory and practical knowledge with designing experiments.

D-optimal designs are one form of design usually provided by a computer algorithm. These types of computer-aided designs are particularly useful when classical designs do not apply. Unlike standard classical designs, such as factorials and fractional factorials, D-optimal design matrices are usually not orthogonal and effect estimates are correlated. These types of designs are always an option regardless of the type of model the experimenter wishes to fit (for example, first order, first order plus some interactions, full quadratic, cubic, etc.) or the objective specified for the experiment (for example, screening, response surface, etc.). In statistics, a central composite design is an experimental design, useful in response surface methodology, for building a second order (quadratic) model for the response variable without needing to use a complete three-level factorial experiment.

Further details about the aforementioned statistic methods are described in George E. P. Box, J. Stuart Hunter, William G. Hunter, "Statistics for Experimenters", Wiley 2005, ISBN-13: 978-0471718130, by George E. P. Box, Norman R. Draper: "Empirical Model-Building and Response Surfaces", Wiley 1987, ISBN-13: 978-0471810339, and by Peter Goos, Bradley Jones: "Optimal Design of Experiments—A Case Study Approach", Wiley 2011, ISBN-13: 978-0470744611.

It is the core of a design of experiments that one or more parameters are varied during the set of experiments so as to determine the functional relationship of influencing parameters. Preferably, the at least one empirical model has been obtained in the method in accordance with the present invention by making use of the results of a plurality of experiments, in which the colour shade and/or colour brightness in terms of L, a, b, C, and/or h° values of the top side of a plurality of multi-layer systems has been measured at least at the first observation angle and the second observation angle, wherein in the plurality of multi-layer systems at least the colour shade and/or colour brightness of the top side of the at least one first colour layer b) and the colour shade and/or colour brightness of the top side of the at least one second colour layer d) and preferably also the coverage of the effect layer c) have been varied. This is realized in that in the plurality of multilayer systems used in the plurality of experiments the colourants used in the layers of the at least one first colour layer b) and the colourants used in the layers of the at least one second colour layer d) are varied. More preferably, in the plurality of multi-layer systems used in the plurality of experiments the number of layers forming the at least one first colour layer b), the number of layers forming the at least one second colour layer d), the colourants used in the layers of the at least one first colour layer b) and the colourants used in the layers of the at least one second colour layer d) are varied. Even more preferably, in the plurality of multi-layer systems used in the plurality of experiments also the coverage of the effect layer c), more preferably also the coverages of each of the at least one first colour layer b) and of each of the at least one second colour layer d) and most preferably also the average particle area of the effect layer c) and dry layer thickness of each layer are varied.

An example for a second order equation, corresponding to an empirical model is:

$$\text{response} = \beta_0 + \sum_{i=1}^{n} \beta_i \cdot x_i + \sum_{i=1}^{n} \sum_{j \geq i}^{n} \beta_{ij} \cdot x_i \cdot x_j$$

with response: any measured characteristic like L[−15], L[15], . . . , L[110], a[−15], a[15], . . . a[110], b[−15], b[15], b[110] or a characteristic, calculated from measured characteristics (including a Box-Cox-transformed response), like the size of the flip-flop-effects $x_i$, $x_j$: settings of the experimental factors, describing the plurality of experiments as calculated by the statistics program $\beta_0$, $\beta_i$, $\beta_{ij}$: sets of coefficients, that are determined by least squares fit, that minimizes the sum of squares of the differences between measured value of the response and the value, calculated from the equation above, over all runs of the DOE, whereby every single characteristic is described by a set of coefficients of its own.

The summations i=1 to n and j≥i to n are related to all experimental factors.

Box-Cox-Transformations are e.g. described in George E. P. Box, J. Stuart Hunter, William G. Hunter, "Statistics for Experimenters", Wiley 2005, ISBN-13: 978-0471718130, by George E. P. Box, Norman R. Draper: "Empirical Model-Building and Response Surfaces", Wiley 1987, ISBN-13: 978-0471810339, and by Peter Goos, Bradley Jones: "Optimal Design of Experiments—A Case Study Approach", Wiley 2011, ISBN-13:978-0470744611.

Also, empirical models of a higher order, like e.g. cubic models may be suitable.

Preferably, in the plurality of experiments, on which the at least one empirical model bases, three or more different colourants, such as three colourants, which preferably a cyan colourant, a magenta colourant and a yellow colourant, are varied. In this embodiment, in the plurality of experiments a plurality of multi-layer systems is used in which the number of first colour layers b) is varied between 0 and 3 and the number of second colour layers d) is varied between 0 and 3, wherein in the multi-layer systems comprising two or more first colour layers b) and/or two or more second colour layers d) for each of the two or more first colour layers b) a different one of the three colourants is used and for each of the two or more second colour layers d) a different one of the three colourants is used. It is preferred that at least 90%, more preferably at least 95%, even more preferably at least 99% of the multi-layer systems used in the experiments comprise at least one first colour layer b), the effect layer c) and at least one second colour layer d), whereas the remainder of the experiments lacking the first colour layer b) and/or the effect layer c) and/or the second colour layer d) are merely to form marginal values of the at least one empirical model.

For example, in such a set of experiments, the following parameters may be varied as follows, whereas in all experiments the same substrate, the same colourant system and the same effect pigment layer recipe are used and the layers are applied onto the substrate using the same application technique (such as flexographic printing) using the same application parameters (such as ink viscosity, draining time, color density of full tone control areas of each layer, solid content of inks, respectively):

Number of first colour layers b): 0, 1, 2 and 3, wherein each first colour layer is made from an ink comprising a cyan colourant, a magenta colourant or a yellow colourant, wherein each of the first colour layers contains a different colourant than the others.

Coverage of each of the first colour layers b): 0%, 33%, 67% and 100%.

Coverage of the effect layer c): 0%, 33%, 67% and 100%.

Number of second colour layers d): 0, 1, 2 and 3, wherein each second colour layer is made from an ink comprising a cyan colourant, a magenta colourant or a yellow colourant, wherein each of the first colour layers contains a different colourant than the others.

Coverage of each of the second colour layers b): 0%, 33%, 67% and 100%.

Of course, other gradings for instance for the layer coverages may be used, such as 0%, 25%, 50%, 75%, 100% or 0%, 20%, 40%, 60%, 80%, 100%.

For evaluating these experiments, the colour shades and/or colour brightness in terms of L, a, b, C, and/or h° at at least two different observation angles comprising at least the first observation angle and the second observation angle specified in step ii) of the top side of the multi-layer systems produced in the experiments are measured as described above. Preferably the at least one empirical model is based on L, a and b values. An empirical model is developed using a statistics program, like Cam Line Cornerstone 7, Statgraphics Centurion 18 or Minitab 18, that allows to describe the relation between the colour shades and/or colour brightness at at least two different observation angles and the varied parameters. As set out above, the at least one model used is preferably at least one empirical model of second order. Details how such models can be developed and optimized are described e.g. in "Statistics for Experimenters", George E. P. Box, J. Stuart Hunter, William G. Hunter, ISBN-13: 978-0471718130. The obtained at least one empirical model contains colour shades and/or colour brightness in terms of L, a, b, values at at least two different observation angles for the specific multi-layer system used (i.e. colorant system, specific substrate, effect layer c) recipe, application technique, application parameters etc.). For a different multi-layer system, a different model needs to be developed.

In accordance with a further specific embodiment of the present invention, in the plurality of experiments, on which the at least one empirical model bases, four different colourants are used and varied, which are preferably a cyan colourant, a magenta colourant, a yellow colourant and a black colourant. In this embodiment, in the plurality of experiments a plurality of multi-layer systems is used in which the number of first colour layers b) is varied between 0 and 4 and the number of second colour layers d) is varied between 0 and 4, wherein in the multi-layer systems comprising two or more first colour layers b) and/or two or more second colour layers d) for each of the two or more first colour layers b) a different of the four colourants is used and for each of the two or more second colour layers d) a different of the four colourants is used. It is preferred that at least 90%, more preferably at least 95%, even more preferably at least 99% of the multi-layer systems used in the experiments comprise at least one first colour layer b), the effect layer c) and at least one second colour layer d), whereas the remainder of the experiments lacking the first colour layer b) and/or the effect layer c) and/or the second colour layer d) are merely to form marginal values of the at least one empirical model.

In accordance with a further specific embodiment of the present invention, in the plurality of experiments, on which the at least one empirical model bases, seven different colourants are used and varied, which are preferably a cyan colourant, a magenta colourant, a yellow colourant, a black colourant, an orange colourant, a green colourant and a violet colourant. In this embodiment, in the plurality of experiments a plurality of multi-layer systems is used in which the number of first colour layers b) is varied between 0 and 7 and the number of second colour layers d) is varied between 0 and 7, wherein in the multi-layer systems comprising two or more first colour layers b) and/or two or more second colour layers d) for each of the two or more first colour layers b) a different of the seven colourants and for each of the two or more second colour layers d) a different of the seven colourants is used. It is preferred that at least 90%, more preferably at least 95%, even more preferably at least 99% of the multi-layer systems used in the experiments comprise at least one first colour layer b), the effect layer c) and at least one second colour layer d), whereas the remainder of the experiments lacking the first colour layer b) and/or the effect layer c) and/or the second colour layer d) are merely to form marginal values of the at least one empirical model.

In a further development of the idea of the present invention, the at least one empirical model provided in step iv) has been obtained by performing 50 to 5,000, preferably 50 to 1,000 and more preferably 100 to 500 experiments with different multiple-layer systems, wherein in the single experiments the colour shade and/or colour brightness of the top side of a plurality of multi-layer systems has been measured in terms of L, a, b, C and/or h° values at least at the first observation angle and the second observation angle. As in the above embodiments, preferably in the plurality of multi-layer systems the colour shade and/or colour brightness of the top side of the at least one first colour layer and the colour shade and/or colour brightness of the top side of the at least one second colour layer, the coverage of the at least one first colour layer, the coverage of the at least one second colour layer and/or the coverage of the effect layer have been varied.

In order to completely determine the colour flip-flop effect, it is preferred that the at least one empirical model provided in step iv) has been obtained by measuring for each of the experiments, on which the at least one empirical model bases, at least the colour shade and/or colour brightness in terms of L, a, b, C, and/or h° values of the top side of the respective multi-layer system at at least three different observation angles and more preferably at least five different observation angles and most preferably at observation angles of $-15°$, $15°$, $25°$, $45°$, $75°$ and $110°$. As described above, the measurements are performed by irradiating in a dark environment a standardized light type onto the multi-layer system at an angle of incident of 45° with respect to the horizontal direction, wherein the angle of reflection of 135° with respect to the horizontal direction is defined as an observation angle of 0°.

In accordance with a particular preferred embodiment of the present invention, the at least one empirical model provided in step iv) has been obtained by performing the following steps:

α) providing in step iii) a colourant system, which comprises at least three different colourants spanning a colour space covering at least 100,000, preferably at least 250,000, more preferably at least 500,000 and most preferably at least 1 million perceptual different colour shades being generable by applying a combination of one or more of the at least three different colourants above each other, and further comprising an effect pigment layer recipe, β) generating a design of experiments using a statistics program designed for calculating an empirical model so as to propose a plurality of experiments, wherein in each of these experiments a specific multi-layer system is applied under specific conditions with specific application parameters onto a specific substrate, wherein at least 90% of these experiments differ from all other experiments of the plurality of experiments in at least one parameter, γ) performing the plurality of experiments proposed in step β), wherein for each of the experiments at least the colour shade and/or colour brightness of the top side of the respective multi-layer system is measured at least at a first observation angle and a second observation angle and preferably at at least three different observation angles and more preferably at at least five different observation angles, δ) entering the numeric values of the colour shades and/or colour brightness in terms of i) L, a, and b and/or ii) L, C, and h° values measured in step γ) into the statistics program, ε) allowing the statistics program to calculate at least one empirical model preferably for each response (L, a and b, respectively, at the at least first observation angle and at the at least second observation angle).

As in the above described embodiments, also in this specific embodiment particular good results are obtained, when in step α) a colourant system is provided, which comprises a cyan colourant, a magenta colourant and a yellow colourant and optionally additionally at least one of a black colourant, an orange colourant, a green colourant and a violet colourant. For instance, the colourant system may comprise a cyan colourant, a magenta colourant and a yellow colourant only, or may comprise a cyan colourant, a magenta colourant, a yellow colourant and a black colourant, or may comprise a cyan colourant, a magenta colourant, a yellow colourant, a black colourant, an orange colourant, a green colourant and a violet colourant.

In step β), a design of experiments is generated and preferably one or more D-optimal designs of experiments are generated making use of a statistics program designed for calculating at least one empirical model so as to propose a plurality of experiments, wherein in each of these experiments a specific multilayer system is formed under specific conditions using specific application parameters for applying the layers b) to d) onto a specific substrate, wherein at least 90% of these experiments differ from all other experiments of the plurality of experiments in at least one parameter. In these experiments, any suitable application technique may be used for applying the layers of the multi-layer system onto each other. Preferably, when the multi-layer system is an ink system, any known printing technique may be used, such as offset, lithography, intaglio printing, flexographic printing, gravure printing, screen printing, digital printing, inkjet printing, pad printing, transfer printing, letter printing and the like. In the case of a multilayer lacquer or coatings system, electrostatic spray coating, air and airless electrostatic systems, dip coating, electrophoresis, anodic electrodeposition (anaphoresis), cathodic electrodeposition (cathaphoresis), autophoresis, flooding, casting, drum coating, spin coating, intaglio coating, rolling, coil coating, powder coating, whirl-sintering, flame spraying or electrostatic powder spraying may be used.

In the experiments proposed in step β) and performed in step γ), preferably the colourant(s) used in the first and second colour layer(s) b) and d) are varied and more preferably also the coverages of the single layers b), c) and d) are varied, if the system is an inks system. When the system is a lacquer or coatings system preferably the colourant(s) used in the first and second colour layer(s) b) and d) are varied and more preferably also the colour layer(s) thicknesses and/or pigment content(s) in the colorant(s) used in the first and second colour layer(s) b) and d), as well as in the effect layer c) are varied.

The plurality of experiments are performed in step γ) preferably as described in more detail above by varying one or more parameters.

In steps δ) and ε), any common statistics program, like Cam Line Cornerstone 7, Statgraphics Centurion 18 or Minitab 18, may be used.

It is preferred that the at least one empirical model provided in step iv) has been obtained by making use of multi-layer systems with an effect layer c) having a thickness of 0.1 to 50 μm, preferably of 0.1 to 30 μm and most preferably of 0.2 to 20 μm or of 0.1 to 150 μm, preferably of 1 to 100 μm and more preferably of 10 to 50 μm.

In a further development of the idea of the present invention it is proposed that the at least one empirical model provided in step iv) has been obtained by making use of multi-layer systems, which all do not contain any interference pigment.

In accordance with a particular preferred embodiment of the present invention, a prognosis is calculated in step v), wherein the prognosis in step v) is preferably calculated for more than 5,000, more preferably for more than 10,000, even more preferably for more than 25,000, still more preferably for more than 50,000 and most preferably for more than 70,000 different multi-layer systems.

The statistics program allows to determine the coefficients β of equations mentioned above from the data measured in the experiments proposed by the design of experiments by means of least-squares fits. In other words, the empirical model is for each response an equation, which includes the determined coefficients and which, after inserting the settings of the experimental parameters, allows to calculate prognosis values of the responses.

In order to have a high variance of different datasets in the prognosis, if the multilayer system is an ink system, it is preferred that each of the multi-layer systems of the prognosis differ from at least 80%, more preferably from at least 90%, still more preferably from at least 99% and most preferably from all other multi-layer systems of the prognosis in at least the colour shade of at least one of the at least one first colour layer b), the colour shade of at least one of the at least one second colour layer d), the coverage of at least one of the at least one first colour layer b), the coverage of at least one of the at least one second colour layer d) and the coverage of the effect layer c). As described above, the variance in the colour shade of at least one of the first and second colour layers b) and d) may be realized in that in the plurality of multi-layer systems of the prognosis the colourants used in the layers of the at least one first colour layer b) and the colourants used in the layers of the at least one second colour layer d) are varied. More preferably, in the multi-layer systems of the prognosis the number of layers forming the at least one first colour layer b), the number of layers forming the at least one second colour layer d), the colourants used in the layers of the at least one first colour layer b) and the colourants used in the layers of the at least one second colour layer d) are varied. Even more preferably, in the plurality of multi-layer systems of the prognosis also the coverage of the effect layer c) and most preferably also the coverages of each of the at least one first colour layer b) and of each of the at least one second colour layer d) are varied.

In order to have a high variance of different datasets in the prognosis, if the multilayer system is a coatings or lacquer system, it is preferred that each of the multilayer systems of the prognosis differ from at least 80%, more preferably from at least 90%, still more preferably from at least 99% and most preferably from all other multi-layer systems of the prognosis in at least the colour shade of at least one of the at least one first colour layer b), the colour shade of at least one of the at least one second colour layer d), the pigment content of at least one of the at least one first colour layer b), the pigment content of at least one of the at least one second colour layer d) the pigment content of the effect layer c), the dry colourant film thickness of the at least one of the at least one first colour layer b), the dry colourant film thickness of at least one of the at least one second colour layer d) and/or the dry film thickness of the effect layer c). As described above, the variance in the colour shade of at least one of the first and second colour layers b) and d) may be realized in that in the plurality of multi-layer systems of the prognosis the colourants used in the layers of the at least one first colour layer b) and the colourants used in the layers of the at least one second colour layer d) are varied. More preferably, in the multi-layer systems of the prognosis the number of layers forming the at least one first colour layer b), the number of layers forming the at least one second colour layer d), the colourants used in the layers of the at least one first colour layer b) and the colourants used in the layers of the at least one second colour layer d) are varied. Even more preferably, in the plurality of multilayer systems of the prognosis also the pigment content of the effect layer c), most preferably also the pigment content of each of the at least one first colour layer b) and of each of the at least one second colour layer d), even more preferably the dry film thickness of the effect layer c), and most preferably also the dry colourant film thickness of each of the at least one first colour layer b) and of each of the at least one second colour layer d) are varied.

The results of the prognosis may be provided in any suitable form. For instance, the results of the prognosis may be provided as lookup table. Alternatively, the prognosis data may be provided as a database so that a selection of colour shades and/or brightnesses for different viewing angles can be entered into the database and one or more suitable results are presented from which the user may select one match, such as the best match.

Concerning the kind of substrate a), the present invention is not particularly limited. Preferably, the substrate a) has a sum of reflectance and scattering of at least 50%, preferably of at least 60%, more preferably of at least 70%, still more preferably of at least 80% and most preferably of at least 90%. For instance, the substrate a) may be a paper, cardboard, foil, film, glass, textile, nonwoven, silicone substrate, ceramic substrate, mineral substrate or white wood substrate. As preferred high reflecting and scattering substrates, respective high reflecting papers, cardboards, foils, white films, white glasses, white textiles, white nonwovens, white silicone substrates, white ceramic substrates, white mineral substrates, white metallic substrates, and white wood substrates may be mentioned. Good results are obtained for instance, when the substrate a) is a white film which preferably contains 0.1 to 10% by weight, more preferably 0.25 to 4% by weight and still more preferably 0.75 to 1.5% by weight of white pigment based on the total weight of the film. Good results are in particular obtained, when the film has a thickness of preferably 1 to 100 µm, more preferably of 2 to 50 µm and most preferably of 10 to 30 µm. Thicker films or even plastic boards or moulds are also most suitable. Also preferred is that the substrate a) is a paper and preferably a paper which contains 1 to 50% by weight, more preferably 1 to 10% by weight and still more preferably 3 to 7% by weight of white pigment based on the total weight of the substrate a). Good results are in particular obtained, when the paper has a thickness of at least 10 µm. Thicker papers or even cardboards are also most suitable. If a white pigment is included in the substrate, it is preferred that the white pigment is titanium oxide and most preferably rutile. Preferably, the titanium oxide and more preferably rutile is present in the form of particles having an average $d_{50}$ particle size of 0.1 to 50 µm, preferably of 0.1 to 10 µm and more preferably of 0.2 to 1 µm. If the substrate a) is a thicker substrate like cardboard or glass, the pigment particles can be bigger; for thin films, white inks and coatings a smaller particle size is more preferred.

It is also possible that the substrate a) of the multi-layer system is an ink layer, a coating, a lacquer layer or an enamel layer, which preferably contains, depending on the layer thickness and the type of layer, 10 to 90% by weight of binder based on the total weight of the liquid ink, coating, lacquer or enamel. In the case that the substrate a) is enamel, the enamel preferably consists of silicates and oxides. The present invention is not particularly limited concerning the kind of binder included in the substrate a). However, it is preferred that the binder is selected from the group consisting of polyesters, polyethers, polyurethanes, polyam ides, polyacrylates, maleinate resins, collophonium resins, ketone resins, aldehyde resins, alkyd resins, collophonium modified phenolic resins, hydrocarbon resins, silicates, silicones, phenolic resins, urea resins, melamine resins, epoxy resins, polyterpene resins, shellac, copal, dammar, lignin derivatives, natural resins, polyvinylalcohols, polyvinylether, polyvinylacetates, polyvinylchloride, polyvinylethers, polyvinylpropionates, polyvinylbutyrates, polymethacrylates, polystyrenes, polyolefines, hydrocarbon resins, coumarone-indene resins, aromatic formaldehyde resins, carbamide acid resins, sulfonamide resins, chlorinated resins, nitrocellulose, CAB (cellulose acetate butyrate), CAP (cellulose acetate propionate), cellulose compounds, rubbers, polysaccharides, radiation curing resins, temperature curing resins and arbitrary combinations of two or more of the aforementioned binders. In addition to the binder or instead of the binder, the liquid ink, coating, lacquer or enamel used to form the substrate a) may contain more than 0 to 95% by weight of solvent, based on the total weight of the liquid inks, coating, lacquer or enamel used to form the substrate a). The solvent amount depends on the ink system, the application and the pigment content. Good results are in particular obtained, when the solvent is selected from the group consisting of mineral oils, vegetable oils, fatty acid esters, alcohols, esters, ethers, glycols, water, cyclic or linear hydrocarbons, ketones, lactones, alkanes, aromatic hydrocarbons, monomers and oligomers with hydroxy, carboxy, alkoxy, amino, acrylic or vinyl functionality, aromatic compounds and arbitrary combinations of two or more of the aforementioned solvents. Furthermore, it is preferred that the liquid ink, coating, lacquer or enamel used to form the substrate a) may contain one or more additives. Examples for such additives are those selected from the group consisting of rheological additives, adhesives, defoamers, slip additives, anti-corrosion additives, gloss additives, waxes, wetting agents, curing agents, chelating agents, photoinitiators, inhibitors, desiccants, stabilizers, emulsifiers, pH adjustment additives, abrasions resistance additives, plasticizers, antistatic additives, preservatives, light protection agents, matting agents, fillers and arbitrary combinations of two or more of the aforementioned additives.

As set out above, the term "colourant" means in accordance with the present invention a compound or mixture containing one or more colouring substances, such as pigment(s) and/or dye(s). Therefore, the "colourant" may be a finished product forming the at least one first or second colour layer and may be for instance a printing ink, a coating, a lacquer, a foil or a film. Alternatively, the "colourant" may be a semi-finished product, in which the colouring substance(s), such as pigment(s) and/or dye(s), is/are dispersed in a solvent or solvent mixture, respectively, which has to be mixed with a non-colouring varnish, that is composed of one or more binders, such as alkyd resin, and one or more solvents, such as mineral oil or vegetable oil, and one or more additives, such as defoamers, photoinitiators, hardeners or stabilizers, so as to form a finished product being able to form the at least one first and/or second colour layer. Independently from the colourant used in the at least one first and/or second colour layer, it is preferred that the at least one dye and/or at least one pigment of the colourant of the first colour layer b) is different from the at least one dye and/or at least one pigment included in the at least one second colour layer d). This leads to a particularly distinct flip-flop effect. In particular, it is preferred that at least one dye and/or at least one pigment included in the first colour layer b) has a different colour or colour shade, respectively, and/or a different brightness than at least one dye and/or at least one pigment included in the at least one second colour layer d), i.e. the colour shade and/or lightness of the first colour layer b) is different to the colour shade and/or lightness of the one second colour layer d).

In accordance with another particular preferred embodiment of the present invention, any of the at least one first colour layer b) and of the at least one second colour layer d) of the multi-layer system in accordance with the present invention contains 0.001 to 5% by weight of at least one dye and/or 0.1 to 60% by weight or preferably 0.1 to 50% by weight of at least one pigment being no platelet-shaped effect pigment and preferably also no white pigment, based on the total dry weight of the at least one first colour layer b) and the at least one second colour layer d), respectively. The pigments are preferably organic or inorganic pigments with a specific colour. Each of the at least one first colour layer b) as well as each of the at least one second colour layer d) may comprise one or more white pigments and/or one or more platelet-shaped (effect) pigments and/or fillers in addition to that/those pigment(s) being no white pigment and no platelet-shaped effect pigment. However, it is preferred that each of the at least one first colour layer b) as well as each of the at least one second colour layer d) does not comprises any platelet-shaped effect pigment as well as not any white pigment.

When the multi-layer system is a coatings or lacquer system, it is preferred that the at least one first colour layer b) has a higher pigment content than the at least one second colour layer d). and that the pigment content in the at least one dry second colour layer d) is 2 to 30%, more preferably 2 to 25% and most preferably 2-20%. When the multi-layer system is an ink system, it is preferred, that the pigment content in the at least one dry second colour layer d) is 0.1 to 50%, more preferably 1 to 50% and most preferably 2 to 50%.

It is suggested in a further development of the present invention that the second colour layer d) and, if more than one second colour layer d) is present, the assembly of all second colour layers d) has a sum of reflectance and scattering of 1 to 80%, more preferably of 5 to 60% and most preferably of 5 to 40%.

Also particularly any of the inks, coatings or lacquers used to form the at least one first colour layer b) and the at least one second colour layer d) preferably contains, depending on the ink, coating or lacquer system, the viscosity and the application method, 10 to 99,9% by weight of binder based on the total weight of the first colour layer b) and of the at least one second colour layer d), wherein the binder is preferably selected from the group consisting of polyesters, polyethers, polyurethanes, polyamides, polyacrylates, maleinate resins, collophonium resins, ketone resins, aldehyde resins, alkyd resins, collophonium modified phenolic resins, hydrocarbon resins, silicates, silicones, phenolic resins, urea resins, melamine resins, epoxy resins, polyterpene resins, shellac, copal, dammar, lignin derivatives, natural resins, poly-vinylalcohols, polyvinylether, polyvinylacetates, polyvinylchloride, polyvinylethers, polyvinylpropionates, polyvinylbutyrates, polymethacrylates, polystyrenes, polyolefines, hydrocarbon resins, coumarone-indene resins, aromatic formaldehyde resins, carbamide acid resins, sulfonamide resins, chlorinated resins, nitrocellulose, CAB (cellulose acetate butyrate), CAP (cellulose acetate propionate), cellulose compounds, rubbers, polysaccharides, radiation curing resins, temperature curing resins and arbitrary combinations of two or more of the aforementioned binders.

In addition to the binder or instead of the binder, any of the inks, coatings or lacquers used to form the at least one first colour layer b) and the at least one second colour layer d) of the multi-layer system in accordance with the present invention may contain, depending on the ink, coating or lacquer system, the viscosity and the application method, more than 0 to 90% by weight of solvent based on the total weight of the liquid ink, coating or lacquer used to form the first colour layer b) and/or of the liquid ink(s), coating(s) or lacquer(s) used to form the at least one second colour layer d), wherein the solvent is preferably selected from the group consisting of mineral oils, vegetable oils, fatty acid esters, alcohols, esters, ethers, glycols, water, cyclic or linear hydrocarbons, ketones, lactones, alkanes, aromatic hydrocarbons, monomers and oligomers with hydroxy, carboxy, alkoxy, amino, acrylic or vinyl functionality, aromatic compounds and arbitrary combinations of two or more of the aforementioned solvents.

Furthermore, also any of the liquid inks, coatings or lacquers used to form the at least one first colour layer b) and the at least one second colour layer d) of the multi-layer system in accordance with the present invention may contain one or more additives. Examples for such additives are those selected from the group consisting of rheological additives, adhesives, defoamers, slip additives, anticorrosion additives, gloss additives, waxes, wetting agents, curing agents, chelating agents, photoinitiators, inhibitors, desiccants, stabilizers, emulsifiers, pH adjustment additives, abrasions resistance additives, plasticizers, antistatic additives, preservatives, light protection agents, matting agents, fillers and arbitrary combinations of two or more of the aforementioned additives.

Preferably, the multi-layer system includes 1 to 3, more preferably 1 or 2 and most preferably 1 first colour layer(s) b) below the effect layer c).

In accordance with a further preferred embodiment of the present invention, the multi-layer system includes 1 to 3 and more preferably 1 or 2 second colour layers d) on/above the effect layer c).

It is particularly preferred that the first colour layer(s) b) are arranged in direct contact with the effect layer c) and with the substrate a), i.e. that there is no intermediate layer between the first colour layer b) and the effect layer c) and no intermediate layer between the first colour layer b) and the substrate a). In case of more than one first colour layer b), the uppermost colour layer is in direct contact with the effect layer c) and the lowest first colour layer b) is in direct contact with the substrate a), wherein all the colour layers b) are arranged in direct contact with each other one above another. These embodiments are particularly preferred, if the multi-layer system is an ink system, a coating system or a lacquer system. If the multi-layer system is a foil/film system, then one or more adhesive layers may be present between one or more of the layers a), b), c) and d).

Likewise to this, it is particularly preferred that the second colour layer(s) d) are arranged in direct contact the effect layer c), i.e. that there is no intermediate layer between the effect layer c) and the second colour layer d). In case of more than one second colour layer d), the lowest colour layer d) is preferably in direct contact with the effect layer c), wherein all the colour layers d) are preferably arranged in direct contact with each other one above another. These embodiments are particularly preferred, if the multi-layer system is an ink system, a coating system or a lacquer system. If the multi-layer system is a foil/film system, then one or more adhesive layers may be present between one or more of the layers.

In a further development of the idea of the present invention the at least one first dry colour layer b) and/or the at least one second dry colour layer d) has a thickness of 0.3 to 100 µm, preferably of 0.5 to 10 µm and more preferably of 1 to 10 µm, particularly if the multi-layer system is an ink system. If more than one first colour layer b) is contained, then preferably the sum of the thicknesses of all first colour layers b) is 0.3 to 100 µm and more preferably of 0.5 to 10 µm. Likewise thereto, if more than one second colour layer d) is contained, then preferably the sum of the thicknesses of all dry second colour layers d) is 0.3 to 100 µm and more preferably of 0.5 to 10 µm. When the multi-layer system is a coatings or lacquer system, the at least one first dry colour layer b) has a thickness of 1 to 500 µm. If more than one first colour layer b) is contained, then preferably the sum of the thicknesses of all dry first colour layers b) is 1 to 500 µm. The at least one second dry colour layer d) has preferably a thickness of 10 to 80 µm, more preferably of 10 to 70 µm and still more preferably of 10 to 50 µm. If more than one second colour layer d) is contained, then preferably the sum of the thicknesses of all dry second colour layers d) is 10 to 80 µm, more preferably of 10 to 70 µm and most preferably of 10 to 50 µm.

If the multi-layer system is an ink system, particularly good results are obtained, when the ink coverage of each of the at least one first colour layers b) on the substrate a), respectively, is 10 to 100%, more preferably 20 to 100% and most preferably 25 to 100%. Also, it is preferred that the ink coverage of the sum of all of the at least one first colour layers b) on the substrate a), respectively, is, if the multi-layer system is an ink system, 30 to 200%, more preferably 50 to 200% and most preferably 50 to 180%.

If the multi-layer system is a coatings system, a lacquer system, or a film/foil system, the coverage of the sum of all of the at least one first colour layers b) on the substrate a), respectively, is complete, i.e. 100% or at least 95%.

Likewise thereto, it is preferred that the ink coverage of each of the at least one second colour layers d) on the effect layer c) is 10 to 90%, more preferably 30 to 80% and most preferably 40 to 60%. Also, it is preferred that the ink coverage of the sum of all of the at least one second colour layers d) on the effect layer c) is 30 to 200% and more preferably 60 to 180%.

If the multi-layer system is a coating system, a lacquer system, or a film/foil system, the coverage of the sum of all of the at least one second colour layers d) on the effect layer c) is complete, i.e. 100% or at least 95%.

Apart from the above described layers, the multi-layer system may comprise one or more further layers. For instance, the multi-layer system may comprise above the at least one second colour layer (d) a second effect layer and above that at least one third colour layer. The at least one third colour layer is in principle composed likewise to the at least one first colour layer b) and to the at least one second colour layer d), i.e. the at least one third colour layer contains at least one dye and/or pigment, the dye and/or pigment being no platelet-shaped effect pigment. It is preferred in this embodiment that the at least one dye and/or at least one pigment included in the third colour layer is different from the at least one dye and/or at least one pigment included in the at least one first colour layer as well as different from the at least one dye and/or at least one pigment included in the at least one second colour layer. Thus, the at least one third colour layer has a different colour or colour shade, respectively, and/or brightness than at least one dye and/or at least one pigment included in the at least one first colour layer b) and also has a different colour or colour shade, respectively, and/or brightness than at least one dye and/or at least one pigment included in the at least one second colour layer d), i.e. the colour shade and/or brightness of the at least one third colour layer is different to the colour shade and/or brightness of the first and second colour layers b) and d).

In particular, if the multi-layer system is a coatings system or a lacquer system, such as a coating for an automobile coating, it is preferred that above the uppermost second colour layer d), or above the uppermost third colour layer, if present, a layer of clear lacquer is arranged for protecting the multi-layer system against mechanical impacts and degradation. Any known clear lacquer may be used for this purpose, such as one or two component clear coats. Merely exemplarily, the clear coat may contain as binder acrylates, polyesters, polyurethanes, all OH-functional in case of 2 components systems or mixtures thereof. In addition, it may contain as solvent water or organic solvents, as hardener two-or polyfunctional isocyanates or amines and as additives, rheological additives, adhesives, defoamers, slip additives, plasticizers, anti-corrosion additives, gloss additives, waxes, wetting agents, curing agents, chelating agents, photoinitiators, inhibitors, desiccants, stabilizers, emulsifiers, pH adjustment additives, abrasions resistance additives, antistatic additives, preservatives, light protection agents, and arbitrary combinations of two or more of the aforementioned additives. The thickness of this clear lacquer layer is preferably at least 50 µm.

In particular, if the multi-layer system is an ink system, such as e.g. an ink system for packaging applications, it may be preferred that above the uppermost second colour layer d) or above the uppermost third colour layer, if present, an overprint lacquer is arranged for protecting the multi-layer system against mechanical impacts and to adjust gloss level. Such an overprint lacquer may be a one or two component system and may contain as binders polyesters, polyethers, polyurethanes, polyamides, polyacrylates, maleinate resins, collophonium resins, ketone resins, aldehyde resins, alkyd resins, collophonium modified phenolic resins, hydrocarbon resins, silicates, silicones, phenolic resins, urea resins, melamine resins, epoxy resins, polyterpene resins, shellac, copal, dammar, lignin derivatives, natural resins, poly-vinylalcohols, polyvinylether, polyvinylacetates, polyvinylchloride, polyvinylethers, polyvinylpropionates, polyvinylbutyrates, polymethacrylates, polystyrenes, polyolefines, hydrocarbon resins, coumarone-indene resins, aromatic formaldehyde resins, carbamide acid resins, sulfonamide resins, chlorinated resins, nitrocellulose, CAB (cellulose acetate butyrate), CAP (cellulose acetate propionate), cellulose compounds, rubbers, polysaccharides, radiation curing resins, temperature curing resins and arbitrary combinations of two or more of the aforementioned binders, and may contain as solvents mineral oils, vegetable oils, fatty acid esters, alcohols, esters, ethers, glycols, water, cyclic or linear hydrocarbons, ketones, lactones, alkanes, aromatic hydrocarbons, monomers and oligomers with hydroxy, carboxy, alkoxy, amino, acrylic or vinyl functionality aromatic compounds and arbitrary combinations of two or more of the aforementioned solvents as solvents, and may contain as hardener two-or poly-functional isocyanates, amines or photoinitiators.

In addition, it is preferred that the multi-layer system does not comprise (except possible adhesive layer(s)) between the substrate a) and the effect layer c) any further layer in addition to the at least one first colour layer b) below the effect layer c). Moreover, it is also preferred that above the effect layer c) (except possible adhesive layer(s)) only the at least one second colour layer d) and optionally one or more further colour layers and/or unpigmented overprint lacquers and/or coatings are arranged.

As set out above, a particular advantage of the present invention is that a flip-flop effect is obtained, even without incorporating any interference pigment into any layer of the multi-layer system. Accordingly, in accordance with the present invention the multi-layer system, i.e. the aforementioned layers a) to d), does not contain any interference pigment.

Furthermore, the present invention relates to a multi-layer system being obtainable with the method described above.

Moreover, the present invention relates to the use of a multi-layer system and preferably an ink, a coating or lacquer system according to the present invention for coating and in particular printing or spraying a substrate. Such systems can be used in automotive surfaces (indoor and outdoor), on computer cases, in passports, banknotes, food-packaging, journals, beer cans, clothings, furnitures, floor panels, wall papers, cosmetic packagings, labels for spare parts, security features in general, mobile phone cases or on any architectural surface.

Subsequently, the present invention is described by means of illustrating, but not limiting figures, wherein:

FIG. 3 shows the results of angle dependent colour measurements in terms of a and b measurements of four different systems in accordance with one embodiment of the present invention.

FIG. 4a, b show sample holders, which are suitable for fixing longitudinal sections or cross-sectional sections of a multi-layer system in accordance with the present invention or of a layer thereof for SEM analysis for determining the particle length, particle width and particle thickness.

FIG. 4c shows an exemplary schematic pigment particle showing the particle length and particle width.

FIG. 5a, b show the principle of the determination of the average particle area ratio of a layer of the system in accordance with the present invention.

FIG. 6 shows the principle of the determination of the reflectance and scattering of a layer of the system in accordance with the present invention.

Figure 1:
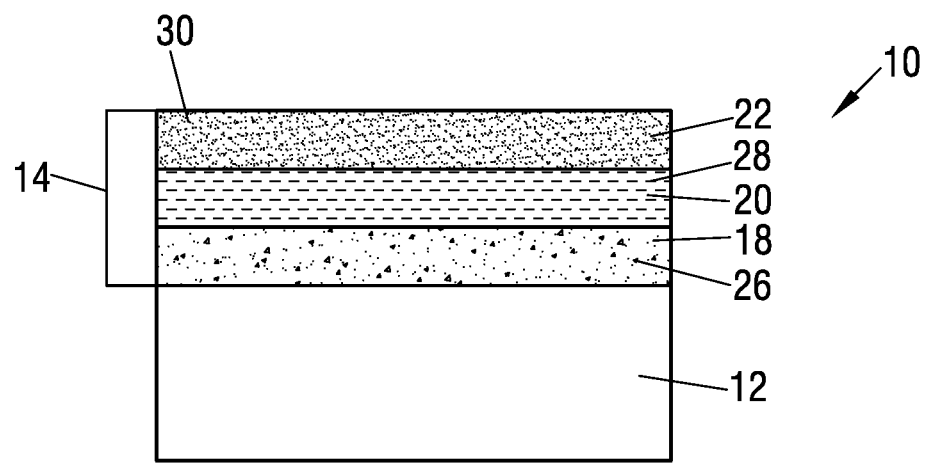
FIG. 1 shows an object comprising a substrate, which is coated with an ink system in accordance with one embodiment of the present invention.

FIG. 1 shows a multi-layer system 10 obtainable with a method in accordance with the present invention. The multi-layer system 10 comprises a substrate 12, which is coated with an ink sequence 14. The ink sequence 14 comprises from the bottom up a first colour layer 18, an effect layer 20 and a second colour layer 22. The first colour layer 18 contains about 0.001 to 5% by weight of dye 26 and/or about 0.1 to 50% of pigment, based on the total weight of the dry first colour layer 18, whereas the effect layer 20 includes 5 to 70% by weight of metallic effect pigment, e.g. platelet-shaped aluminium effect particles, 28 consisting of aluminium having an average particle length of about 10 μm, an average particle width of about 5 μm, an average thickness of about 0.5 μm and thus a first aspect ratio of 2 and a second aspect ratio of 20, based on the total weight of the dried effect layer 20 and the second colour layer 22 contains about 0.001 to 5% by weight of dye 30 and/or 0.1 to 50% of pigment based on the total weight of the dried second colour layer 22.

Figure 2:
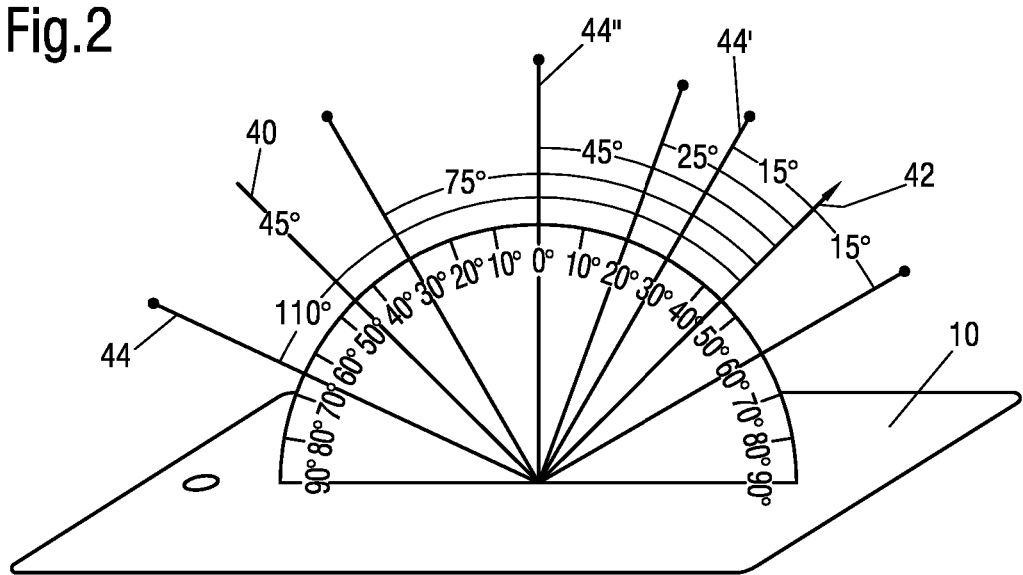
FIG. 2 shows schematically a method for measuring the angle dependent colour measurement of a system in accordance with one embodiment of the present invention.

FIG. 2 shows schematically a method for measuring the angle dependent colour appearance of a system in accordance with one embodiment of the present invention. In a dark environment, a visible light beam 40 with an adjusted intensity and wavelength range is irradiated onto a system 10 as described for instance with regard to FIG. 1 at an angle of 45° with respect to the horizontal direction. Since the angle of incidence with regard to the horizontal direction is the same as the angle of reflection 42 of the irradiated light beam, the angle of reflection 42 is 135° with respect to the horizontal direction. This angle of reflection 42 is defined for the measurement of the angle dependent colour appearance of the multi-layer system in accordance with the present invention as an observation angle of 0°. In order to measure the angle dependent colour appearance of the multi-layer system 10, the sum of reflectance and scattering is measured at different observation angles 44, 44', 44", for instance—as shown in FIG. 2—at observation angles of −15°, 15°, 25°, 45°, 75° and 110°. Of course, it is also possible to measure the colour appearance at more than six different observation angles or at less than six different observation angles, such as at five different observation angles, such as at observation angles of 15°, 25°, 45°, 75° and 110°. For these measurements, for example a Byk mac i instrument from Byk Gardner, Geretsried, Germany can be used, with D50 light incidence and a six angle measurement at the observation angles describes above. It is most suitable to measure rectangular samples with a minimum width of 2 cm and a minimum length of 5 cm. It is especially preferred that at least 10 samples are measured, even more preferred is the measurement of 100 or even 600 samples.

FIG. 3 shows the results of angle dependent colour measurements of four different multi-layer systems in accordance with one embodiment of the present invention. The angle dependent colour measurements of the four different systems have been performed as described above with regard to FIG. 2 at observation angles of −15°, 15°, 25°, 45°, 75° and 110°. At each observation angle, the a-value as well as the b-value of each system have been determined. The respective values are plotted in FIG. 3 for any of the four systems, wherein the largest triangle of each graph represents the value measured at an observation angle of −15°. The further markers in each graph starting from the largest triangle represent the respective values determined at observation angles of 15°, 25°, 45°, 75° and 110°. The horizontal axis of FIG. 3 shows the measured a-values, whereas the vertical axis of FIG. 3 shows the measured b-values. As it can be seen from FIG. 3, the a-values and b-values of all four samples differ depending of the observation angle at which they have been determined. This shows, that all four systems showed a flip-flop effect.

FIGS. 4a and 4b show sample holders, which are suitable for fixing longitudinal sections or cross-sectional sections, respectively, of a multi-layer system in accordance with the present invention or of a layer thereof for SEM analysis for determining the particle length, particle width and particle thickness. The sample holder shown in FIG. 4a is suitable for longitudinal sections of a layer or a system (for frontal view), whereas the sample holder shown in FIG. 4b is suitable for cross-sectional sections of a layer or a system. The sections are placed onto the respective sample holder area as shown by the blue arrow.

FIG. 4c shows an exemplary schematic pigment particle 46 showing the particle length 48 and particle width 50. The particle length 48 is the longest extension of the particle 46, whereas the particle width 50 is defined in this connection as the longest extension of the particle 46 in the direction being perpendicular to the particle length 48. The particle thickness is the shortest extension of the particle 46 in the direction being perpendicular to the two-dimensional plane being defined by the particle length 48 and the particle width 50, i.e. the extension of the particle perpendicular to the paper plane.

FIGS. 5a and 5b show the principle of the determination of the average particle area ratio of a layer of the system in accordance with the present invention by SEM from a longitudinal section of the concerned layer of the system being prepared as described above. The particles 46 are colored with the software tool "ParticleMetric" as shown in FIG. 5a and then the sum of the area in the longitudinal section which is covered by particles 46 as shown in FIG. 5b is evaluated and divided by the total area of the longitudinal section analyzed by scanning electron microscopy so as to obtain the average particle area ratio in percent.

FIG. 6 shows the principle of the determination of the reflectance and scattering of a layer of the system in accordance with the present invention. A piece of the prepared layer, such as a longitudinal section thereof or the layer itself, having for instance an area of 10 cm² is cut out of the system and placed in the measurement apparatus, which is preferably the Haze-Gloss instrument from Byk Garnder, Geretsried, Germany. Norm light D65 shown by the reference number 52 is irradiated in defined angle β of 20° from the vertical direction onto the surface of the layer 54 to be analyzed and the reflected (which corresponds to gloss 56, as described in DIN 67530) as well as the scattered light (which corresponds to haze 58) is detected by a sensor 60.

Subsequently, the present invention is described by means of an illustrating, but not limiting example.

Example 1

In brief, a D-optimal design of experiments was generated and then the experiments suggested by the software were performed. The results of the experiments were entered into the software, which therefrom calculated a second order model and, where necessary (especially, when response is L), third order models. Then a prognosis has been calculated making use of the empirical models.

Generating the D-Optimal Design of Experiments and Performing the Experiments

For performing the experiments of the D-optimal design of experiments, the following parameters were used:
Substrate: White PE film, 30 μm thick
Printing machine: central cylinder flexo printing machine Flexpress 6S/8 from Fischer&Krecke
Printing parameters: print speed 250m/min; corona intensity 2 kV; anilox rollers in print units: 3.9 cm³/m² for coloured inks in ink units 1 to 3, 8.0 cm³/m² for silver ink, 3.5 cm³/m² for ink units 5-7360 lines/c for all coloured inks, 220 lines/cm for silver ink;
Effect pigment layer recipe: 76GU318960 (hubergroup). Diluted with ethanol/ethyl acetate 9:1, print viscosity 22s in DIN 4 cup.
Colourant 1: 63GU336821 (hubergroup), printing ink including a cyan pigment Blue 15:4 colourant with L=58,0, a=−38,0 and b=−45,0. Diluted with ethanol/ethylacetate 9:1, print viscosity 20s in DIN 4 cup; colour density 1,6.
Colourant 2: 62GU336816 (hubergroup), printing ink including a magenta pigment Red 57:1 colourant with L=52,0, a=71,0 and b=1,0. Diluted with ethanol/ethyl acetate 9:1, print viscosity 20s in DIN 4 cup; colour density 1,5.
Colourant 3: 61GU336812 (hubergroup), printing ink including a yellow pigment Yellow 13 colourant with L=91,0, a=−5,0 and b=95,0. Diluted with ethanol/ethyl acetate 9:1, print viscosity 20s in DIN 4 cup; colour density 1,4.
Color density can be measured with a spectro-densitometer, e.g. from Techkon or X-Rite with the following parameters:

| Light type: | D50 |
| Viewing angle: | 2° |
| Polarisation filter: | no filter |

ABS: Reference to white standard tile (part of spectro-densitometer measuring system)
MO: specifies that D50 contains undefined share of UV light
Lab values of the used colourants are specified in DIN ISO 13655, with $$\Delta E^*_{ab} = (\Delta a^2 + \Delta b^2)^{1/2}$$

And acceptable tolerances:
Yellow: $\Delta E^*_{ab} = 5,0$
Magenta: $\Delta E^*_{ab} = 6,0$
Cyan: $\Delta E^*_{ab} = 6,0$ It was decided to enter into the software as printing parameters to be varied the following parameters:
Number of first colour layers b): 0, 1, 2 and 3, wherein each of the first colour layers contains a different colourant than the others.
Coverage of each of the first colour layers b): 0%, 33%, 67% and 100%.
Coverage of the effect layer c): 0%, 33%, 67% and 100%.
Number of second colour layers d): 0, 1, 2 and 3, wherein each of the second colour layers contains a different colourant than the others.
Coverage of each of the second colour layers b): 0%, 33%, 67% and 100%.

Three full factorial designs of experiments with multi-layer system each having two of the colourants 1 to 3 above the effect layer and one of colourants 1 to 3 below the effect layer have been calculated, wherein for each of the three full factorial designs of experiments a D-optimal design of experiments including 50 experiments has been selected. Moreover, three full factorial designs of experiments with multi-layer system each having one of the colourants 1 to 3 above the effect layer and two of colourants 1 to 3 below the effect layer have been calculated, wherein for each of the three full factorial designs of experiments a D-optimal design of experiments including 20 experiments has been selected. In addition, the following 10 special experiments have been provided:

1—first colour layer colourant 1 with 100% coverage—effect layer with 100% coverage—one second colour layer colourant 3 with 100% coverage and above that another second colour layer colourant 2 with 100% coverage
2—first colour layer colourant 2 with 100% coverage—effect layer with 100% coverage—one second colour layer colourant 3 with 100% coverage and above that another second colour layer colourant 1 with 100% coverage
3—first colour layer colourant 3 with 100% coverage—effect layer with 100% coverage—one second colour layer colourant 2 with 100% coverage and above that another second colour layer colourant 1 with 100% coverage
4—first colour layer colourant 1 with 100% coverage—effect layer with 100% coverage—second colour layer colourant 3 with 100% coverage
5—first colour layer colourant 1 with 100% coverage—effect layer with 100% coverage—second colour layer colourant 2 with 100% coverage
6—first colour layer colourant 2 with 100% coverage—effect layer with 100% coverage—second colour layer colourant 3 with 100% coverage
7—first colour layer colourant 2 with 100% coverage—effect layer with 100% coverage—second colour layer colourant 1 with 100% coverage
8—first colour layer colourant 3 with 100% coverage—effect layer with 100% coverage—second colour layer colourant 2 with 100% coverage
9—first colour layer colourant 3 with 100% coverage—effect layer with 100% coverage—second colour layer colourant 1 with 100% coverage
10—one first colour layer colourant 3 with 100% coverage, above that another second colour layer colourant 2 with 100% coverage and above that another second colour layer colourant 1 with 100% coverage—effect layer with 100% coverage—no second colour layer The experiments were performed by applying each of the layers onto each other starting with applying the first colour layer b) onto the substrate with the predetermined application technique and application parameters. Then, the colour shades and brightness for each multi-layer system were measured in form of the $L^*$-, $a^*$-, $b^*$-, $C^*$- and $h^°$-values with a Byk mac I instrument at five observation angles of −15°/15°/25°/45°/75°/110°.

The following results are obtained, DW meaning ink unit, according to the sequence of units used:

| DW1 Yellow | DW2 Magenta | DW3 Cyan | DW4 Ag | DW5 Yellow | DW6 Magenta | DW7 Cyan |
|---|---|---|---|---|---|---|
| 0 | 100 | 0 | 100 | 100 | 0 | 100 |
| 0 | 50 | 0 | 100 | 0 | 0 | 100 |
| 0 | 100 | 0 | 67 | 100 | 0 | 100 |
| 0 | 100 | 0 | 100 | 100 | 0 | 0 |
| 0 | 50 | 0 | 33 | 100 | 0 | 100 |
| 0 | 50 | 0 | 67 | 100 | 0 | 33 |
| 0 | 100 | 0 | 33 | 67 | 0 | 100 |
| 0 | 50 | 0 | 100 | 33 | 0 | 33 |
| 0 | 100 | 0 | 100 | 67 | 0 | 67 |
| 0 | 50 | 0 | 0 | 33 | 0 | 100 |
| 0 | 100 | 0 | 33 | 100 | 0 | 67 |
| 0 | 50 | 0 | 0 | 100 | 0 | 0 |
| 0 | 50 | 0 | 100 | 100 | 0 | 67 |
| 0 | 100 | 0 | 100 | 33 | 0 | 100 |
| 0 | 50 | 0 | 100 | 67 | 0 | 0 |
| 0 | 50 | 0 | 67 | 67 | 0 | 100 |
| 0 | 100 | 0 | 100 | 0 | 0 | 33 |
| 0 | 100 | 0 | 0 | 0 | 0 | 100 |
| 0 | 100 | 0 | 0 | 100 | 0 | 33 |
| 0 | 50 | 0 | 33 | 0 | 0 | 67 |
| 0 | 100 | 0 | 67 | 33 | 0 | 0 |
| 0 | 100 | 0 | 67 | 33 | 0 | 0 |
| 0 | 50 | 0 | 0 | 67 | 0 | 33 |
| 0 | 100 | 0 | 0 | 67 | 0 | 0 |
| 0 | 100 | 0 | 67 | 67 | 0 | 33 |
| 0 | 100 | 0 | 0 | 33 | 0 | 67 |
| 0 | 100 | 0 | 33 | 33 | 0 | 33 |
| 0 | 50 | 0 | 67 | 0 | 0 | 0 |
| 0 | 50 | 0 | 33 | 33 | 0 | 0 |
| 0 | 50 | 0 | 67 | 33 | 0 | 67 |
| 0 | 100 | 0 | 67 | 100 | 0 | 67 |
| 0 | 100 | 0 | 100 | 0 | 0 | 0 |
| 0 | 100 | 0 | 67 | 0 | 0 | 100 |
| 0 | 100 | 0 | 100 | 67 | 0 | 100 |
| 0 | 50 | 0 | 0 | 0 | 0 | 67 |
| 0 | 50 | 0 | 33 | 0 | 0 | 33 |
| 0 | 100 | 0 | 33 | 0 | 0 | 0 |
| 0 | 50 | 0 | 33 | 67 | 0 | 67 |
| 0 | 50 | 0 | 0 | 100 | 0 | 100 |
| 0 | 50 | 0 | 100 | 100 | 0 | 33 |
| 0 | 50 | 0 | 33 | 33 | 0 | 100 |
| 0 | 50 | 0 | 100 | 33 | 0 | 67 |

-continued

| | | | | | | | |
|---|---|---|---|---|---|---|---|
| 0 | 100 | 0 | 67 | 67 | 0 | 0 | 0 |
| 0 | 50 | 0 | 33 | 67 | 0 | 0 | 33 |
| 0 | 100 | 0 | 67 | 0 | 0 | 0 | 67 |
| 0 | 100 | 0 | 0 | 33 | 0 | 0 | 0 |
| 0 | 50 | 0 | 0 | 67 | 0 | 0 | 67 |
| 0 | 100 | 0 | 67 | 33 | 0 | 0 | 33 |
| 0 | 100 | 0 | 33 | 100 | 0 | 0 | 0 |
| 0 | 50 | 0 | 0 | 0 | 0 | 0 | 33 |
| 0 | 50 | 0 | 67 | 100 | 0 | 0 | 0 |
| 0 | 0 | 100 | 100 | 100 | 100 | 100 | 0 |
| 0 | 0 | 50 | 33 | 100 | 100 | 100 | 0 |
| 0 | 0 | 100 | 100 | 100 | 67 | 100 | 0 |
| 0 | 0 | 100 | 100 | 33 | 100 | 100 | 0 |
| 0 | 0 | 50 | 100 | 100 | 0 | 0 | 0 |
| 0 | 0 | 100 | 0 | 100 | 0 | 0 | 0 |
| 0 | 0 | 50 | 100 | 0 | 67 | 0 | 0 |
| 0 | 0 | 50 | 67 | 0 | 100 | 0 | 0 |
| 0 | 0 | 100 | 0 | 67 | 100 | 0 | 0 |
| 0 | 0 | 50 | 67 | 100 | 33 | 0 | 0 |

| Test field # | L-15 | L15 | L25 | L45 | L75 | L110 | a-15 | a15 | a25 | a45 | a75 | a110 | b-15 | b15 | b25 |
|---|---|---|---|---|---|---|---|---|---|---|---|---|---|---|---|
| 1 | 84.36 | 72.67 | 51.38 | 29.24 | 20.12 | 16.03 | −48.1 | −47.92 | −41.2 | −27.33 | −19.89 | −18.05 | 14.31 | 16.06 | 13.27 |
| 2 | 126.41 | 76.02 | 55.86 | 36.53 | 29.91 | 25.85 | −29.51 | −32.53 | −23.46 | −14.04 | −10.65 | −9.81 | −39.01 | −36.66 | −33.09 |
| 3 | 67.66 | 95.99 | 62.72 | 33.09 | 21.36 | 17.27 | −44.3 | −32.3 | −44.47 | −30.91 | −20.84 | −18.49 | 15.23 | 10.21 | 15.59 |
| 4 | 120.81 | 96.91 | 72.77 | 46.6 | 36.62 | 32.9 | 1.12 | 2.87 | 6.53 | 15.68 | 22.19 | 23.66 | 66.31 | 63.15 | 52.99 |
| 5 | 68.56 | 76.53 | 54.36 | 35.43 | 29.68 | 26.63 | −45.39 | −42.99 | −45.24 | −37.9 | −34.83 | −34.41 | 12.99 | 11.79 | 14.45 |
| 6 | 96.35 | 104.85 | 75.48 | 48.11 | 39.27 | 36.28 | −10.79 | −11.37 | −10.37 | −4.66 | −1.4 | −0.24 | 43.77 | 45.17 | 43.19 |
| 7 | 73.94 | 60.57 | 43.73 | 25.45 | 18.97 | 15.46 | −32.77 | −30.77 | −25.53 | −12.88 | −6.29 | −5.07 | −9.21 | −7.1 | −7.81 |
| 8 | 120.42 | 106.57 | 75.08 | 47.99 | 39.52 | 36.18 | −10.61 | −10.37 | −6.86 | −1.14 | 1.6 | 2.18 | 2.99 | 3.85 | 3.38 |
| 9 | 97.81 | 91.75 | 64.98 | 36.72 | 25.5 | 21.51 | −23.24 | −22.92 | −18.08 | −7.44 | −0.33 | 1.62 | 8.87 | 9.71 | 7.67 |
| 10 | 40.95 | 50.98 | 41.15 | 39.03 | 38.41 | 36.28 | −18.67 | −10.37 | −22.57 | −26.12 | −26.88 | −26.98 | −22.3 | −22.78 | −23.02 |
| 11 | 79.95 | 81.03 | 56.96 | 33.71 | 25.39 | 22.03 | −20.5 | −20 | −16.11 | −4.25 | 2.94 | 4.57 | 25.21 | 26.33 | 23.25 |
| 12 | 64.41 | 69.88 | 65.74 | 64.04 | 63.82 | 62.42 | 26.31 | 24.48 | 28.47 | 30.13 | 30.48 | 30.5 | 47.51 | 41.83 | 56.31 |
| 13 | 122.02 | 74.98 | 54.93 | 36.58 | 30.01 | 26.02 | −19.47 | −27.93 | −24.61 | −19.24 | −16.96 | −15.38 | 23.22 | 31.85 | 26.71 |
| 14 | 84.88 | 87.46 | 61.03 | 32.25 | 20.69 | 16.57 | −47.2 | −41.1 | −33.28 | −16.31 | −6.46 | −4.22 | −24.68 | −23.92 | −21.11 |
| 15 | 133.98 | 101.46 | 76.41 | 52.66 | 45.04 | 41.34 | 0.13 | 2.06 | 4.88 | 10.28 | 12.96 | 13.41 | 36.8 | 36.5 | 32.37 |
| 16 | 88.25 | 71.09 | 53.35 | 34.62 | 28.5 | 24.79 | −42.11 | −43.48 | −39.12 | −30.48 | −27.38 | −26.27 | −6.94 | −4.09 | −3.7 |
| 17 | 110.57 | 138.37 | 94.35 | 48.24 | 31 | 27.07 | −3.14 | −5.22 | −4.08 | 8.85 | 20.63 | 23.96 | −11.1 | −12.72 | −14.51 |
| 18 | 40.76 | 30.79 | 26.52 | 23.04 | 21.63 | 18.67 | 11.32 | 13.64 | 14.64 | 15.72 | 16.06 | 15.19 | −35.91 | −40.97 | −43.41 |
| 19 | 40.16 | 47.6 | 38.13 | 33.94 | 32.81 | 31.09 | 26.76 | 24.02 | 31.76 | 36.47 | 37.93 | 37.72 | 8.39 | 3.62 | 15.72 |
| 20 | 93.27 | 77.31 | 59.24 | 43.01 | 38.53 | 35.16 | −17 | −15.12 | −10.05 | −3.94 | −1.82 | −1.51 | −28.06 | −26.71 | −26.84 |
| 21 | 126.47 | 107.68 | 79.12 | 47.7 | 36.83 | 33.43 | 3.33 | 5.82 | 11.24 | 24.32 | 33.23 | 34.61 | 15.89 | 17.06 | 14.16 |
| 21 | 126.47 | 107.68 | 79.12 | 47.7 | 36.83 | 33.43 | 3.33 | 5.82 | 11.24 | 24.32 | 33.23 | 34.61 | 15.89 | 17.06 | 14.16 |
| 22 | 56.65 | 64.33 | 54.42 | 52.51 | 52.01 | 49.67 | 4.34 | 4.36 | 4.73 | 4.92 | 4.96 | 4.83 | 10.75 | 8.77 | 15.72 |
| 23 | 51.34 | 55.17 | 50.05 | 47.17 | 46.42 | 44.9 | 52.1 | 50.57 | 58.62 | 63.03 | 64.3 | 63.92 | 18.37 | 17.29 | 23.65 |
| 24 | 90.74 | 105.94 | 73.7 | 42.2 | 30.98 | 27.73 | −7.15 | −7.88 | −3.67 | 8.53 | 17.28 | 19.5 | 20.37 | 20.91 | 18.45 |
| 25 | 36.22 | 39.95 | 32.01 | 27.56 | 26.44 | 24.46 | 16.39 | 17.3 | 20.92 | 23.56 | 24.73 | 24.48 | −18.81 | −19.42 | −21.08 |
| 26 | 89.93 | 86.99 | 62.01 | 38.88 | 31.4 | 28.52 | −1.98 | −1.13 | 6.27 | 20.83 | 28.56 | 29.52 | 0.89 | 1.4 | −0.14 |
| 27 | 109.81 | 125.3 | 88.59 | 58.25 | 49.37 | 46.98 | 5.01 | 4.06 | 8.85 | 17.32 | 21.5 | 22.16 | −2.01 | −2.7 | −2.58 |
| 28 | 98.72 | 112.93 | 82.75 | 60.01 | 54.21 | 52.09 | 7.02 | 5.24 | 10.9 | 18.59 | 21.42 | 21.93 | 16.5 | 15.81 | 16.04 |
| 29 | 101.43 | 86.22 | 62.36 | 41.37 | 34.89 | 31.47 | −22.7 | −21.33 | −16.7 | −10.63 | −8.23 | −7.59 | −9.54 | −8.95 | −8.46 |
| 30 | 85.36 | 69.09 | 51.49 | 31.83 | 24.15 | 20.31 | −24.67 | −22.63 | −17.7 | −7.57 | −1.58 | 0.04 | 30.61 | 29.88 | 24.42 |
| 31 | 117.7 | 129.24 | 88.39 | 50.05 | 36.07 | 32.83 | 4.63 | 4.43 | 9.52 | 22.5 | 33.17 | 35.31 | −1.79 | −2.19 | −1.98 |
| 32 | 76.63 | 99.97 | 66.67 | 34.45 | 21.39 | 17.39 | −32.89 | −35.8 | −27.99 | −8.4 | 4.16 | 6.93 | −39.14 | −41.62 | −37.08 |
| 33 | 81.88 | 77.53 | 55.67 | 30.83 | 20.61 | 16.44 | −42.07 | −41.54 | −34.77 | −20.57 | −12.63 | −10.88 | −5.37 | −4.45 | −4.66 |
| 34 | 53.38 | 49.51 | 48.86 | 47.68 | 47.09 | 43.6 | 0.59 | −0.04 | −0.73 | −1.26 | −1.39 | −1.41 | −30.66 | −31.49 | −31.21 |
| 35 | 94.55 | 103.45 | 74.83 | 52.24 | 46.42 | 43.97 | −4.33 | −3.91 | 0.04 | 7.22 | 9.83 | 10.08 | −15.18 | −14.76 | −15.82 |
| 36 | 102.87 | 96.41 | 71.61 | 48.14 | 41.05 | 38.38 | 12.46 | 14.49 | 24.62 | 41.69 | 49.61 | 50.16 | −2.83 | −2.02 | −3.21 |
| 37 | 94.26 | 84.32 | 61.53 | 41.83 | 36.01 | 32.75 | −20.47 | −20.93 | −19.33 | −14.48 | −12.43 | −11.67 | 7.89 | 7.98 | 7.97 |
| 38 | 46.11 | 40.61 | 37.29 | 35.14 | 34.24 | 31.08 | −22.02 | −29.52 | −37.68 | −42.7 | −44.04 | −43.94 | −1.25 | 5.01 | 11.06 |
| 39 | 105.96 | 97.15 | 71.03 | 46.59 | 38.36 | 34.95 | −13.66 | −13.46 | −11.16 | −6.34 | −3.88 | −2.91 | 51.22 | 50.28 | 43.85 |
| 40 | 95.07 | 62.49 | 49.11 | 36 | 31.9 | 28.32 | −21.78 | −33.5 | −28.97 | −23.22 | −21.27 | −20.36 | −22.73 | −20.8 | −20.04 |
| 41 | 99.88 | 95.21 | 67.33 | 41.96 | 33.48 | 30.08 | −23.94 | −23.62 | −18.91 | −11.99 | −9.03 | −8.25 | −8.93 | −8.22 | −7.56 |
| 42 | 119.28 | 102.39 | 75.14 | 47.25 | 37.78 | 34.45 | 3.79 | 5.9 | 11.4 | 23.8 | 31.48 | 32.76 | 34.6 | 35.07 | 29.92 |
| 43 | 95.48 | 95.68 | 69.93 | 48.61 | 42.38 | 39.49 | −8.89 | −8.36 | −5.89 | −0.55 | 1.85 | 2.47 | 19.88 | 20.8 | 19.6 |
| 44 | 113.29 | 88.78 | 61.89 | 34.76 | 24.66 | 20.95 | −19.51 | −16.66 | −8.29 | 5.96 | 15.02 | 16.19 | −28.38 | −26.1 | −23.82 |
| 45 | 143.1 | 49.96 | 48.37 | 46.43 | 45.39 | 41.54 | 17.5 | 58.31 | 61.98 | 63.82 | 64.17 | 61.27 | 22.7 | 10.61 | 11.31 |
| 46 | 54.32 | 46.7 | 44.66 | 42.95 | 42.41 | 39.33 | −5.92 | −10.2 | −12.3 | −13.28 | −13.3 | −13.09 | −1.16 | 0.11 | 2.87 |
| 47 | 104.95 | 101.07 | 69.61 | 40.73 | 30.39 | 27.07 | −6.94 | −6.16 | −0.03 | 12.73 | 21.23 | 22.66 | 1.48 | 2.71 | 1.56 |
| 48 | 99.66 | 96.73 | 71.29 | 47.76 | 40.3 | 37.44 | 8.28 | 9.47 | 17.43 | 32.22 | 39.71 | 40.83 | 50.34 | 49.4 | 45.33 |
| 49 | 58.05 | 59.98 | 56.96 | 55.78 | 55.4 | 52.95 | 12.85 | 13.75 | 13.96 | 13.94 | 13.8 | 13.45 | −19.5 | −19.86 | −20.82 |
| 50 | 104.84 | 111.51 | 82.56 | 55.93 | 47.74 | 44.96 | 1.73 | 1.03 | 4.31 | 10.88 | 14.36 | 15.42 | 63.58 | 65.12 | 58.37 |
| 51 | 79.25 | 75.21 | 49.36 | 27.27 | 18.79 | 15.23 | 38.26 | 39.57 | 35.36 | 22.59 | 14.67 | 12.65 | 32.39 | 35.21 | 26.82 |
| 52 | 91.11 | 66.5 | 45.87 | 30.64 | 26.16 | 23.09 | 21.75 | 28.1 | 27.7 | 23.91 | 22.21 | 21.6 | 26.8 | 26.89 | 22.75 |
| 53 | 91.95 | 95.89 | 65.62 | 36.48 | 25.67 | 21.79 | 17.58 | 18.79 | 16.3 | 6.48 | −1.22 | −3.34 | 36.28 | 42.18 | 33.39 |
| 54 | 71.91 | 107.48 | 65.12 | 33.88 | 22.3 | 18.65 | 33.18 | 34.51 | 35.46 | 24.48 | 16.62 | 14.45 | 3.07 | 19.47 | 1.48 |

-continued

| | | | | | | | | | | | | | | |
|---|---|---|---|---|---|---|---|---|---|---|---|---|---|---|
| 55 | 111.84 | 114.25 | 84.84 | 57.77 | 49.27 | 46.08 | −7.3 | −7.38 | −10.63 | −16.77 | −19.99 | −20.07 | 63.3 | 64.9 | 53.82 |
| 56 | 51.08 | 59.89 | 52.45 | 49.83 | 48.8 | 46.23 | −53.18 | −46.79 | −60.16 | −66.5 | −68.51 | −69.04 | 20.73 | 15.49 | 27.62 |
| 57 | 106.03 | 86.77 | 62.26 | 40.08 | 32.8 | 29.51 | 23.22 | 23.27 | 20.48 | 15.87 | 13.55 | 12.45 | −9.09 | −10.42 | −11.76 |
| 58 | 76.27 | 79.12 | 54.12 | 33.06 | 26.31 | 23.49 | 44.46 | 46.41 | 41.59 | 33.5 | 29.81 | 28.47 | −14.37 | −14.84 | −16.76 |
| 59 | 43.05 | 51.36 | 31.65 | 20.03 | 18.13 | 16.15 | 0.63 | 2.26 | 2.53 | 2.22 | 2.07 | 2.06 | 0.79 | 7.67 | −2.71 |
| 60 | 91.06 | 106.7 | 73.98 | 47.58 | 39.47 | 36.51 | 5.21 | 4.59 | 2.23 | −4.22 | −7.77 | −8.29 | 48.76 | 49.81 | 44.85 |

| Test field # | b45 | b75 | b110 | C-15 | C15 | C25 | C45 | C75 | C110 | h-15 | h15 | h25 | h45 | h75 | h110 |
|---|---|---|---|---|---|---|---|---|---|---|---|---|---|---|---|
| 1 | 6.13 | 2.12 | 0.97 | 50.18 | 50.54 | 43.28 | 28.01 | 20 | 18.08 | 163.43 | 161.47 | 162.14 | 167.37 | 173.92 | 176.92 |
| 2 | −29.54 | −28.79 | −27.8 | 48.91 | 49.01 | 40.56 | 32.7 | 30.7 | 29.46 | 232.9 | 228.42 | 234.66 | 244.57 | 249.71 | 250.54 |
| 3 | 8.16 | 2.32 | 0.62 | 46.85 | 33.87 | 47.13 | 31.97 | 20.97 | 18.5 | 161.03 | 162.45 | 160.68 | 165.21 | 173.65 | 178.07 |
| 4 | 39.42 | 34.08 | 33.51 | 66.32 | 63.21 | 53.39 | 42.43 | 40.67 | 41.02 | 89.03 | 87.4 | 82.98 | 68.31 | 56.93 | 54.77 |
| 5 | 11.56 | 10.43 | 9.69 | 47.21 | 44.57 | 47.49 | 39.62 | 36.36 | 35.75 | 164.03 | 164.66 | 162.28 | 163.04 | 163.32 | 164.27 |
| 6 | 33.41 | 29.78 | 29.34 | 45.08 | 46.58 | 44.42 | 33.74 | 29.81 | 29.34 | 103.85 | 104.13 | 103.5 | 97.94 | 92.69 | 90.47 |
| 7 | −10.35 | −12.43 | −12.6 | 34.04 | 31.58 | 26.7 | 16.53 | 13.93 | 13.59 | 195.7 | 192.99 | 197.01 | 218.78 | 243.17 | 248.1 |
| 8 | 2.22 | 1.58 | 1.51 | 11.03 | 11.07 | 7.65 | 2.5 | 2.25 | 2.65 | 164.26 | 159.64 | 153.8 | 117.24 | 44.61 | 34.78 |
| 9 | 3.25 | 0.44 | 0.12 | 24.87 | 24.89 | 19.64 | 8.12 | 0.55 | 1.62 | 159.11 | 157.04 | 157.01 | 156.41 | 126.76 | 4.26 |
| 10 | −22.55 | −22.89 | −23.3 | 29.08 | 25.03 | 32.23 | 34.51 | 35.31 | 35.62 | 230.07 | 245.53 | 225.56 | 220.8 | 220.42 | 220.77 |
| 11 | 14.55 | 10.49 | 9.74 | 32.49 | 33.07 | 28.29 | 15.16 | 10.9 | 12.1 | 129.13 | 127.21 | 124.71 | 106.29 | 74.37 | 64.85 |
| 12 | 64.8 | 67.22 | 67.77 | 54.31 | 48.47 | 63.1 | 71.46 | 73.81 | 74.32 | 61.03 | 59.66 | 63.18 | 65.06 | 65.61 | 65.77 |
| 13 | 19.32 | 16.54 | 15.56 | 30.3 | 42.36 | 36.32 | 27.26 | 23.69 | 21.88 | 129.99 | 131.25 | 132.65 | 134.87 | 135.73 | 134.67 |
| 14 | −17.81 | −18.21 | −18.2 | 48.18 | 47.55 | 39.41 | 24.15 | 19.32 | 18.64 | 210.82 | 210.19 | 212.38 | 227.53 | 250.46 | 256.91 |
| 15 | 28.53 | 27.42 | 26.91 | 36.8 | 36.56 | 32.73 | 30.33 | 30.33 | 30.06 | 89.8 | 86.77 | 81.43 | 70.18 | 64.71 | 63.51 |
| 16 | −3.57 | −3.73 | −4.11 | 42.68 | 43.67 | 39.29 | 30.69 | 27.63 | 26.58 | 189.35 | 185.37 | 185.4 | 186.68 | 187.76 | 188.89 |
| 17 | −12.25 | −12.76 | −12.5 | 11.54 | 13.75 | 15.07 | 15.11 | 24.26 | 27.03 | 254.22 | 247.67 | 254.29 | 305.85 | 328.27 | 332.41 |
| 18 | −45.73 | −46.14 | −43.9 | 37.65 | 43.18 | 45.82 | 48.36 | 48.86 | 46.42 | 287.49 | 288.41 | 288.63 | 288.97 | 289.19 | 289.1 |
| 19 | 23.8 | 26.24 | 26.54 | 28.05 | 24.29 | 35.08 | 43.55 | 46.12 | 46.13 | 17.4 | 8.57 | 25.01 | 33.13 | 34.67 | 35.13 |
| 20 | −26.64 | −26.83 | −26.1 | 32.81 | 30.69 | 28.66 | 26.93 | 26.89 | 26.19 | 238.79 | 240.49 | 249.48 | 261.59 | 266.11 | 266.69 |
| 21 | 11.45 | 10.48 | 10.84 | 16.23 | 18.03 | 18.26 | 26.88 | 34.85 | 36.27 | 78.18 | 71.18 | 51.56 | 25.22 | 17.5 | 17.39 |
| 21 | 18.16 | 18.29 | 17.92 | 11.6 | 9.8 | 16.42 | 18.82 | 18.95 | 18.56 | 68.01 | 63.58 | 73.25 | 74.84 | 74.83 | 74.91 |
| 22 | 28.12 | 28.87 | 29.73 | 55.25 | 53.45 | 63.21 | 69.02 | 70.49 | 70.5 | 19.42 | 18.88 | 21.97 | 24.04 | 24.18 | 24.94 |
| 23 | 12.46 | 9.35 | 9.15 | 21.59 | 22.35 | 18.81 | 15.1 | 19.65 | 21.54 | 109.34 | 110.65 | 101.25 | 55.6 | 28.43 | 25.14 |
| 24 | −22 | −22.56 | −21.9 | 24.95 | 26.01 | 29.69 | 32.24 | 33.47 | 32.87 | 311.07 | 311.69 | 314.78 | 316.96 | 317.62 | 318.13 |
| 25 | −3.06 | −4.9 | −4.5 | 2.17 | 1.8 | 6.27 | 21.05 | 28.98 | 29.87 | 155.83 | 128.95 | 358.69 | 351.64 | 350.27 | 351.32 |
| 26 | −2.72 | −3.16 | −3.14 | 5.4 | 4.88 | 9.22 | 17.53 | 21.73 | 22.39 | 338.16 | 326.36 | 343.78 | 351.07 | 351.64 | 351.94 |
| 27 | 15.55 | 15.12 | 15.16 | 17.93 | 16.66 | 19.39 | 24.24 | 26.22 | 26.66 | 66.94 | 71.67 | 55.79 | 39.92 | 35.21 | 34.65 |
| 28 | −8.51 | −8.83 | −8.82 | 24.62 | 23.13 | 18.72 | 13.61 | 12.07 | 11.64 | 202.79 | 202.78 | 206.88 | 218.68 | 226.99 | 229.29 |
| 29 | 15.2 | 10.75 | 9.73 | 39.31 | 37.48 | 30.16 | 16.98 | 10.86 | 9.73 | 128.86 | 127.14 | 125.93 | 116.49 | 98.35 | 89.77 |
| 30 | −1.79 | −2.18 | −1.59 | 4.96 | 4.94 | 9.73 | 22.57 | 33.24 | 35.35 | 338.89 | 333.74 | 348.23 | 355.45 | 356.23 | 357.42 |
| 31 | −31.45 | −31.73 | −31.8 | 51.12 | 54.9 | 46.46 | 32.56 | 32 | 32.54 | 229.96 | 229.3 | 232.95 | 255.05 | 277.47 | 282.29 |
| 32 | −6.17 | −7.91 | −8.39 | 42.41 | 41.78 | 35.08 | 21.48 | 14.9 | 13.74 | 187.28 | 186.11 | 187.63 | 196.69 | 212.06 | 217.64 |
| 33 | −32.43 | −32.52 | −31.6 | 30.67 | 31.49 | 32.45 | 32.46 | 32.55 | 31.61 | 271.1 | 269.94 | 268.72 | 267.77 | 267.55 | 267.27 |
| 34 | −16.42 | −16.91 | −16.8 | 15.78 | 15.27 | 15.82 | 17.93 | 19.56 | 19.59 | 254.08 | 255.15 | 270.14 | 293.75 | 300.17 | 300.96 |
| 35 | −4.35 | −5.27 | −4.12 | 12.77 | 14.63 | 24.83 | 41.92 | 49.89 | 50.33 | 347.21 | 352.08 | 352.57 | 354.04 | 353.94 | 355.31 |
| 36 | 6.17 | 5.33 | 4.88 | 21.93 | 22.41 | 20.91 | 15.74 | 13.55 | 12.65 | 158.91 | 159.12 | 157.59 | 156.92 | 156.79 | 157.29 |
| 37 | 15.05 | 15.68 | 14.63 | 22.05 | 29.94 | 39.27 | 45.27 | 46.74 | 46.31 | 183.24 | 170.37 | 163.64 | 160.58 | 160.4 | 161.58 |
| 38 | 34.01 | 30.83 | 30.27 | 53.01 | 52.05 | 44.77 | 34.6 | 31.07 | 30.41 | 104.93 | 104.99 | 104.43 | 100.56 | 97.18 | 95.49 |
| 39 | −18.74 | −18.61 | −18.4 | 31.49 | 39.43 | 35.23 | 29.83 | 28.27 | 27.42 | 226.22 | 211.84 | 214.67 | 218.9 | 221.19 | 222.05 |
| 40 | −7.13 | −7.37 | −7.49 | 25.55 | 25.01 | 20.36 | 13.95 | 11.66 | 11.14 | 200.45 | 199.2 | 201.78 | 210.72 | 219.22 | 222.2 |
| 41 | 23.93 | 21.9 | 21.97 | 34.8 | 35.56 | 32.02 | 33.75 | 38.35 | 39.45 | 83.74 | 80.45 | 69.14 | 45.15 | 34.83 | 33.85 |
| 42 | 16.49 | 15.25 | 14.85 | 21.78 | 22.42 | 20.46 | 16.5 | 15.36 | 15.06 | 114.1 | 111.91 | 106.73 | 91.9 | 83.06 | 80.57 |
| 43 | −22.83 | −24.16 | −23.2 | 34.44 | 30.96 | 25.2 | 23.6 | 28.45 | 28.3 | 235.5 | 237.46 | 250.82 | 284.63 | 301.87 | 304.91 |
| 44 | 11.39 | 11.35 | 12.39 | 28.66 | 59.27 | 63.01 | 64.83 | 65.16 | 62.51 | 52.38 | 10.32 | 10.34 | 10.12 | 10.03 | 11.43 |
| 45 | 4.4 | 4.41 | 3.89 | 6.03 | 10.2 | 12.63 | 14 | 14.01 | 13.65 | 191.07 | 179.37 | 166.87 | 161.66 | 161.64 | 163.46 |
| 46 | −1.01 | −2.86 | −2.57 | 7.1 | 6.73 | 1.56 | 12.77 | 21.42 | 22.81 | 167.98 | 156.27 | 91.27 | 355.47 | 352.34 | 353.54 |
| 47 | 39.26 | 38.03 | 38.39 | 51.01 | 50.29 | 48.56 | 50.79 | 54.98 | 56.04 | 80.66 | 79.15 | 68.97 | 50.62 | 43.76 | 43.23 |
| 48 | −21.23 | −21.4 | −21 | 23.35 | 24.15 | 25.07 | 25.4 | 25.47 | 24.97 | 303.38 | 304.7 | 303.85 | 303.29 | 302.81 | 302.6 |
| 49 | 48.41 | 45.62 | 45.67 | 63.6 | 65.13 | 58.52 | 49.61 | 47.83 | 48.21 | 88.44 | 89.09 | 85.78 | 77.34 | 72.53 | 71.34 |
| 50 | 15 | 9.05 | 7.63 | 50.13 | 52.97 | 44.2 | 27.12 | 17.24 | 17.7 | 40.25 | 41.66 | 37.18 | 33.59 | 31.68 | 31.09 |
| 51 | 18.01 | 16.46 | 16 | 34.51 | 38.9 | 35.85 | 29.93 | 27.64 | 26.88 | 50.94 | 43.74 | 39.4 | 36.99 | 36.54 | 36.54 |
| 52 | 20.54 | 14.04 | 12.66 | 40.31 | 46.18 | 37.15 | 21.54 | 14.09 | 13.1 | 64.15 | 65.99 | 63.98 | 72.5 | 94.99 | 104.76 |
| 53 | −4.32 | −8.76 | −9.92 | 33.32 | 39.62 | 35.49 | 24.86 | 18.79 | 17.53 | 5.29 | 29.42 | 2.39 | 349.98 | 332.22 | 325.51 |
| 54 | 38.52 | 32.43 | 31.28 | 63.72 | 65.32 | 54.86 | 42.01 | 38.1 | 37.17 | 96.58 | 96.49 | 101.18 | 113.52 | 121.65 | 122.69 |
| 55 | 35.75 | 37.04 | 35.88 | 57.08 | 49.29 | 66.2 | 75.5 | 77.88 | 77.81 | 158.71 | 161.69 | 155.34 | 151.74 | 151.6 | 152.54 |
| 56 | −14.36 | −16.32 | −16 | 24.94 | 25.49 | 23.62 | 21.4 | 21.21 | 20.26 | 338.61 | 335.88 | 330.14 | 317.87 | 309.71 | 307.92 |
| 57 | −18.12 | −19.91 | −19.3 | 46.72 | 48.73 | 44.84 | 38.09 | 35.85 | 34.41 | 342.09 | 342.27 | 338.05 | 331.59 | 326.26 | 325.82 |
| 58 | −12.74 | −14.72 | −14.5 | 1.01 | 7.99 | 3.71 | 12.93 | 14.87 | 14.66 | 51.44 | 73.59 | 313.1 | 279.87 | 278.01 | 278.08 |
| 59 | 34.91 | 31.44 | 30.92 | 49.04 | 50.03 | 44.9 | 35.17 | 32.39 | 32.02 | 83.9 | 84.73 | 87.15 | 96.89 | 103.89 | 105.01 |
| 60 | | | | | | | | | | | | | | | |

| DW1 Yellow | DW2 Magenta | DW3 Cyan | DW4 Ag | DW5 Yellow | DW6 Magenta | DW7 Cyan |
|---|---|---|---|---|---|---|
| 0 | 0 | 100 | 100 | 67 | 0 | 0 |
| 0 | 0 | 50 | 100 | 33 | 33 | 0 |
| 0 | 0 | 50 | 100 | 67 | 100 | 0 |
| 0 | 0 | 100 | 67 | 100 | 100 | 0 |
| 0 | 0 | 50 | 0 | 33 | 100 | 0 |
| 0 | 0 | 50 | 0 | 100 | 67 | 0 |
| 0 | 0 | 100 | 33 | 0 | 100 | 0 |
| 0 | 0 | 100 | 33 | 100 | 33 | 0 |
| 0 | 0 | 100 | 100 | 0 | 33 | 0 |
| 0 | 0 | 50 | 33 | 67 | 0 | 0 |
| 0 | 0 | 100 | 67 | 33 | 67 | 0 |
| 0 | 0 | 50 | 0 | 0 | 33 | 0 |
| 0 | 0 | 100 | 0 | 0 | 67 | 0 |
| 0 | 0 | 100 | 0 | 33 | 33 | 0 |
| 0 | 0 | 100 | 67 | 0 | 0 | 0 |
| 0 | 0 | 100 | 67 | 67 | 33 | 0 |
| 0 | 0 | 50 | 33 | 33 | 67 | 0 |
| 0 | 0 | 50 | 67 | 33 | 0 | 0 |
| 0 | 0 | 50 | 67 | 67 | 67 | 0 |
| 0 | 0 | 100 | 100 | 33 | 0 | 0 |
| 0 | 0 | 100 | 33 | 100 | 67 | 0 |
| 0 | 0 | 100 | 33 | 33 | 100 | 0 |
| 0 | 0 | 100 | 0 | 100 | 100 | 0 |
| 0 | 0 | 50 | 33 | 0 | 0 | 0 |
| 0 | 0 | 50 | 33 | 67 | 33 | 0 |
| 0 | 0 | 100 | 33 | 67 | 67 | 0 |
| 0 | 0 | 50 | 0 | 67 | 0 | 0 |
| 0 | 0 | 50 | 100 | 0 | 100 | 0 |
| 0 | 0 | 50 | 100 | 100 | 33 | 0 |
| 0 | 0 | 50 | 67 | 67 | 100 | 0 |
| 0 | 0 | 100 | 0 | 33 | 67 | 0 |
| 0 | 0 | 50 | 0 | 67 | 33 | 0 |
| 0 | 0 | 100 | 33 | 33 | 0 | 0 |
| 0 | 0 | 100 | 67 | 0 | 67 | 0 |
| 0 | 0 | 50 | 0 | 0 | 0 | 0 |
| 0 | 0 | 100 | 67 | 33 | 33 | 0 |
| 0 | 0 | 100 | 100 | 67 | 67 | 0 |
| 0 | 0 | 50 | 33 | 0 | 33 | 0 |
| 0 | 0 | 50 | 100 | 33 | 67 | 0 |
| 100 | 0 | 0 | 100 | 0 | 100 | 100 |
| 50 | 0 | 0 | 100 | 0 | 100 | 0 |
| 100 | 0 | 0 | 100 | 0 | 0 | 100 |
| 100 | 0 | 0 | 0 | 0 | 100 | 100 |
| 50 | 0 | 0 | 100 | 0 | 67 | 100 |
| 50 | 0 | 0 | 67 | 0 | 0 | 100 |
| 100 | 0 | 0 | 100 | 0 | 67 | 33 |
| 50 | 0 | 0 | 67 | 0 | 100 | 67 |
| 100 | 0 | 0 | 33 | 0 | 100 | 33 |
| 50 | 0 | 0 | 100 | 0 | 33 | 67 |
| 100 | 0 | 0 | 33 | 0 | 67 | 100 |
| 50 | 0 | 0 | 0 | 0 | 33 | 100 |
| 50 | 0 | 0 | 33 | 0 | 100 | 100 |
| 100 | 0 | 0 | 100 | 0 | 100 | 67 |
| 50 | 0 | 0 | 0 | 0 | 100 | 33 |
| 50 | 0 | 0 | 100 | 0 | 0 | 33 |
| 100 | 0 | 0 | 67 | 0 | 100 | 0 |
| 100 | 0 | 0 | 100 | 0 | 33 | 0 |
| 100 | 0 | 0 | 67 | 0 | 33 | 100 |
| 50 | 0 | 0 | 33 | 0 | 67 | 0 |

| Test field # | L-15 | L15 | L25 | L45 | L75 | L110 | a-15 | a15 | a25 | a45 | a75 | a10 | b-15 | b15 | b25 |
|---|---|---|---|---|---|---|---|---|---|---|---|---|---|---|---|
| 61 | 129.92 | 114.05 | 81.74 | 49.94 | 38.5 | 34.43 | −6.25 | −6.74 | −10.48 | −20.3 | −28.85 | −29.86 | 37.53 | 35.4 | 27.96 |
| 62 | 104.08 | 105.38 | 75.49 | 48.47 | 39.95 | 36.87 | 8.52 | 8.89 | 6.43 | 1.15 | −1.83 | −2.54 | 12.02 | 12.75 | 8.99 |
| 63 | 86.79 | 88.85 | 57.68 | 33 | 24.83 | 21.51 | 34.58 | 35.6 | 34.71 | 27.23 | 23.52 | 22.72 | 19.54 | 25.76 | 15.37 |
| 64 | 81.25 | 71.82 | 48.74 | 27.72 | 19.85 | 16.26 | 27.21 | 30.06 | 25.89 | 15.01 | 8.15 | 6.65 | 26.46 | 29.28 | 22.24 |
| 65 | 63.41 | 41.89 | 35.09 | 31 | 29.85 | 26.82 | 13.9 | 23.83 | 30.26 | 33.65 | 34.26 | 32.91 | 4.7 | −4.1 | −9.3 |
| 66 | 55.7 | 68.18 | 45.08 | 40.05 | 39.46 | 37.38 | 3.89 | 4.26 | 5.71 | 6.31 | 6.32 | 6.36 | 19.22 | 25.61 | 27.03 |
| 67 | 72.91 | 66.57 | 45.28 | 26.66 | 20.8 | 17.96 | 34.46 | 36.04 | 32.19 | 24.55 | 20.78 | 19.4 | −13.27 | −13.62 | −20.89 |
| 68 | 86.14 | 77.49 | 58.07 | 39.18 | 32.79 | 29.2 | −1.49 | −2.82 | −8.44 | −20.33 | −28.34 | −29.44 | 39.76 | 39.63 | 33.85 |
| 69 | 123.65 | 103.65 | 72.25 | 43.46 | 33.46 | 29.98 | 9.46 | 8.64 | 5.71 | −0.86 | −5.42 | −6.23 | −8.15 | −8.76 | −12.25 |
| 70 | 109.46 | 105.79 | 79.29 | 59.84 | 54.14 | 50.81 | −8.43 | −10.22 | −14.25 | −20.92 | −23.56 | −23.45 | 31.41 | 30.87 | 29.36 |
| 71 | 90.49 | 92.61 | 62.78 | 36.3 | 27.09 | 23.79 | 19.41 | 20.34 | 15.81 | 6.36 | −0.02 | −1.64 | 4.2 | 6.51 | 0.79 |
| 72 | 60.73 | 60.11 | 58.62 | 57.32 | 56.92 | 53.97 | −0.97 | −0.85 | −1.4 | −1.74 | −1.75 | −1.77 | −23.98 | −24.05 | −26.45 |
| 73 | 43.07 | 53.59 | 40.51 | 35.45 | 34.57 | 32.55 | −1.21 | 1.07 | −1.58 | −2.77 | −3.21 | −3.31 | −30.09 | −21.2 | −34.95 |

-continued

| Test field # | | | | | | | | | | | | | | | |
|---|---|---|---|---|---|---|---|---|---|---|---|---|---|---|---|
| 74 | 49.21 | 47.62 | 44.04 | 41.91 | 41.16 | 38.2 | −21.18 | −23.18 | −28.59 | −31.46 | −31.96 | −31.17 | −15.6 | −15.94 | −18.7 |
| 75 | 115 | 114.99 | 84.67 | 54.75 | 45.55 | 42.38 | −5.86 | −5.89 | −8.9 | −17.25 | −22.53 | −22.93 | −10.46 | −9.22 | −15.07 |
| 76 | 91.26 | 77.67 | 59.62 | 39.9 | 32.69 | 28.95 | 1.39 | 0.12 | −4.06 | −13.17 | −19.78 | −20.75 | 22.22 | 20.52 | 15.28 |
| 77 | 93.68 | 78.97 | 57.2 | 40.65 | 35.93 | 32.81 | 17.64 | 18.79 | 16.68 | 12.58 | 10.73 | 10.09 | 7 | 4.61 | 0.41 |
| 78 | 131.95 | 104.27 | 79.17 | 57.36 | 50.97 | 47.27 | −6.19 | −7.3 | −10.6 | −16.69 | −19.23 | −19.04 | 12.59 | 12.75 | 8.99 |
| 79 | 86.1 | 88.03 | 61.27 | 38.87 | 31.85 | 28.91 | 19.46 | 20.02 | 17.09 | 11.12 | 8.03 | 7.28 | 22.53 | 24.74 | 19.14 |
| 80 | 116.85 | 117.83 | 82.73 | 51.6 | 40.35 | 36.67 | −5.65 | −5.93 | −9.29 | −18.18 | −25.63 | −26.62 | 15.06 | 13.4 | 8.63 |
| 81 | 74.34 | 88.65 | 59.35 | 34.68 | 25.93 | 22.64 | 13.09 | 13.72 | 10.71 | 0.08 | −8.34 | −10.55 | 30.24 | 34.65 | 28.15 |
| 82 | 75.17 | 58.99 | 41.36 | 24.97 | 19.57 | 16.39 | 26.71 | 27.7 | 24.72 | 17.58 | 13.65 | 12.34 | 2.47 | 0.04 | −6.51 |
| 83 | 45.44 | 41.79 | 26.52 | 17.91 | 16.36 | 14.17 | −0.7 | 0.33 | −0.85 | −3.43 | −4.12 | −4.02 | 6.83 | 10.64 | 6.24 |
| 84 | 108.74 | 96.92 | 79.62 | 63.96 | 60.31 | 57.36 | −7.08 | −7.71 | −11.15 | −15.98 | −17.41 | −17.38 | −10.95 | −11.14 | −15.95 |
| 85 | 94.06 | 89.63 | 66.78 | 48.09 | 42.76 | 39.64 | 4.86 | 4.64 | 1.87 | −3.82 | −6.15 | −6.38 | 24.97 | 24.13 | 20.32 |
| 86 | 66.45 | 100.53 | 62.83 | 36.31 | 27.93 | 25.11 | 9.62 | 10.69 | 8.6 | −1.27 | −8.92 | −11.02 | 13.91 | 24.08 | 13.09 |
| 87 | 82.46 | 67.26 | 67.13 | 66.13 | 65.13 | 59.9 | −24.67 | −31.26 | −32.18 | −32.36 | −31.88 | −30.39 | 13.21 | 25.91 | 28.27 |
| 88 | 91.89 | 77.7 | 54.16 | 32.71 | 25.32 | 22.01 | 46.55 | 47.08 | 41.66 | 34 | 30.57 | 29.04 | −15.58 | −15.78 | −15.33 |
| 89 | 98.14 | 98.19 | 71.56 | 46.37 | 37.87 | 34.56 | 6.21 | 6.43 | 3.35 | −2.67 | −6.12 | −6.57 | 49.55 | 51.98 | 43.86 |
| 90 | 75.02 | 76.61 | 51.98 | 31.5 | 25.01 | 22.18 | 40.56 | 41.92 | 39.11 | 30.24 | 26.17 | 24.95 | 16.95 | 19.52 | 13.38 |
| 91 | 127.17 | 92.04 | 72.88 | 54.49 | 48.73 | 44.5 | −8.01 | −10.73 | −15.09 | −21.69 | −24.62 | −23.99 | 61.68 | 60.61 | 53.34 |
| 92 | 69.86 | 38.07 | 33.09 | 30.52 | 29.47 | 25.83 | −0.77 | −7.88 | −10.55 | −12.29 | −12.68 | −11.97 | 1.02 | −17.26 | −22.09 |
| 93 | 54.32 | 63.1 | 55.56 | 53.13 | 52.8 | 51.06 | −7.88 | −6.66 | −8.63 | −9.36 | −9.34 | −9.2 | 14.66 | 14.37 | 17.06 |
| 94 | 104.06 | 98.48 | 74.61 | 52.27 | 45.69 | 42.28 | −10.39 | −11.77 | −17.55 | −30.02 | −36.53 | −36.72 | 5.43 | 5.81 | −0.09 |
| 95 | 88.31 | 94.65 | 65.07 | 38.14 | 29.41 | 26.43 | 19.04 | 20.49 | 16.68 | 8.84 | 3.85 | 2.6 | −12.56 | −12.05 | −16.51 |
| 96 | 74.17 | 73.41 | 73.98 | 73.41 | 72.98 | 69.2 | −21.24 | −21.67 | −22.44 | −22.75 | −22.55 | −21.97 | −28.04 | −27.43 | −27.79 |
| 97 | 109.77 | 94.79 | 68.44 | 42.43 | 33.63 | 30.08 | 5.47 | 5.05 | 1.25 | −7.79 | −14.1 | −15.05 | 8.59 | 8.71 | 3.15 |
| 98 | 97.29 | 87.46 | 60.19 | 35.04 | 25.61 | 21.89 | 20.56 | 20.6 | 16.24 | 6.59 | −0.16 | −1.88 | 24.8 | 23.5 | 16.99 |
| 99 | 103.5 | 94.74 | 71.59 | 51.15 | 45.64 | 42.66 | 7.34 | 7.6 | 5.67 | 1.46 | −0.33 | −0.78 | −7.92 | −9.14 | −13.4 |
| 100 | 94.35 | 96.98 | 68.2 | 41.25 | 32.48 | 29.46 | 21.31 | 22.85 | 20.15 | 14.29 | 11.16 | 10.17 | 6.19 | 9.19 | 4.44 |
| 101 | 59.92 | 75.3 | 43.98 | 21.45 | 14.36 | 11.28 | 11.52 | 16.45 | 9.26 | 1.78 | −1.28 | −2.58 | −38.48 | −40.96 | −37.91 |
| 102 | 79.45 | 97.08 | 65.03 | 40.19 | 33.01 | 30.62 | 46.68 | 46.99 | 47.96 | 43.36 | 41.88 | 41.48 | −8.95 | −1.7 | −7.55 |
| 103 | 101.38 | 81.18 | 61.49 | 41.05 | 34.73 | 30.73 | −44.02 | −42.61 | −38.8 | −37.71 | −39.53 | −39.59 | −38.44 | −30.77 | −21.99 |
| 104 | 42.81 | 32.47 | 22.9 | 17.42 | 15.89 | 13.24 | 4.55 | 3.21 | −2.17 | −6.38 | −7.06 | −7.13 | −11.27 | −9 | −6.6 |
| 105 | 68.57 | 81.74 | 54.14 | 30.99 | 23.69 | 20.78 | −10.77 | −7.79 | −10.64 | −9.49 | −9.36 | −9.87 | −37.68 | −40.02 | −34.74 |
| 106 | 122.85 | 75.2 | 58.3 | 44.09 | 39.59 | 35.35 | −26.93 | −41.29 | −38.33 | −37.41 | −37.52 | −36.34 | −36.52 | −29.75 | −22.59 |
| 107 | 117.33 | 74.69 | 54.51 | 36.05 | 30.27 | 26.82 | 15.86 | 15.56 | 14.57 | 12.8 | 11.96 | 11.35 | −15.19 | −11.86 | −5.31 |
| 108 | 62.74 | 65.99 | 44.09 | 27.04 | 21.89 | 19.25 | 24.4 | 26.42 | 23.65 | 18.99 | 17.3 | 16.63 | −27.62 | −26.59 | −25.07 |
| 109 | 73.33 | 64.8 | 44.47 | 30.54 | 26.67 | 24.08 | 29.77 | 33.54 | 33.53 | 32.38 | 31.87 | 31.16 | −8.4 | −11.16 | −5.47 |
| 110 | 94.35 | 82.51 | 61.05 | 41.08 | 35.14 | 31.93 | −11.91 | −11.36 | −10.25 | −10.27 | −10.87 | −10.97 | −25.3 | −23.18 | −18.57 |
| 111 | 87.81 | 54.03 | 38.53 | 27.09 | 23.45 | 19.95 | −4.82 | −12.02 | −14.63 | −18.45 | −20.52 | −20.75 | −30.85 | −26.98 | −17.55 |
| 112 | 45.31 | 50.51 | 44.71 | 42.99 | 42.34 | 39.88 | −26.19 | −22.45 | −31.96 | −35.43 | −35.93 | −35.75 | −16.97 | −17.78 | −16.54 |
| 113 | 63.41 | 48.87 | 32.12 | 20.7 | 17.26 | 14.46 | 13.23 | 13.39 | 9.58 | 6.55 | 6.06 | 5.58 | −34.59 | −36.37 | −31.51 |
| 114 | 52.51 | 102.88 | 56.54 | 28.23 | 19.36 | 16.57 | 24.15 | 31.2 | 26.64 | 18.65 | 14.81 | 13.99 | −26.02 | −19.97 | −28.43 |
| 115 | 42.09 | 56.76 | 40.93 | 35.83 | 35.02 | 33.58 | 31.46 | 27.47 | 37.02 | 41.64 | 42.62 | 42.7 | −1.39 | 1.5 | −2.54 |
| 116 | 115.37 | 115.22 | 85.18 | 58.92 | 51.65 | 48.87 | −13.4 | −13.41 | −13.31 | −13.31 | −13.88 | −13.84 | −10.32 | −9.37 | −4.73 |
| 117 | 83.83 | 79.43 | 57.4 | 38.9 | 33.73 | 31.28 | 45.92 | 49.81 | 47.96 | 44.55 | 43.39 | 42.7 | −2.2 | −4.47 | 0.46 |
| 118 | 107.58 | 120.51 | 85.92 | 56.25 | 47.9 | 45.73 | 11.63 | 12.6 | 12.3 | 11.7 | 11.38 | 11.14 | 3.07 | 2.72 | 7.48 |
| 119 | 87.41 | 67.19 | 50.16 | 33.61 | 28.54 | 24.94 | −27.12 | −27.76 | −26.73 | −28.06 | −30.07 | −30.22 | −35.73 | −29.85 | −21.38 |
| 120 | 86.48 | 94.34 | 68.77 | 50.31 | 45.77 | 43.64 | 27.59 | 28.14 | 30.22 | 31.49 | 31.52 | 31.11 | 0.16 | 1.77 | 3.11 |

| Test field # | b45 | b75 | b110 | C-15 | C15 | C25 | C45 | C75 | C110 | h-15 | h15 | h25 | h45 | h75 | h110 |
|---|---|---|---|---|---|---|---|---|---|---|---|---|---|---|---|
| 61 | 16.21 | 10.08 | 8.47 | 38.04 | 36.04 | 29.86 | 25.98 | 30.56 | 31.04 | 99.46 | 100.78 | 110.54 | 141.39 | 160.74 | 164.16 |
| 62 | 4.05 | 1.29 | 0.56 | 14.73 | 15.54 | 11.05 | 4.21 | 2.23 | 2.6 | 54.66 | 55.13 | 54.41 | 74.21 | 144.8 | 167.6 |
| 63 | 9.95 | 7.39 | 6.98 | 39.72 | 43.94 | 28.99 | 24.66 | 23.77 | 29.47 | 35.89 | 23.88 | 20.08 | 17.44 | 17.09 | 17.09 |
| 64 | 12.35 | 7.51 | 6.36 | 37.96 | 41.96 | 34.13 | 19.44 | 11.09 | 9.2 | 44.2 | 44.25 | 40.66 | 39.44 | 42.66 | 43.73 |
| 65 | −12.81 | −13.45 | −12.3 | 14.67 | 24.18 | 31.66 | 36.01 | 36.8 | 35.11 | 18.67 | 350.24 | 342.91 | 339.16 | 338.57 | 339.59 |
| 66 | 31.75 | 33.16 | 33 | 19.61 | 25.96 | 27.63 | 32.37 | 33.75 | 33.61 | 78.55 | 80.55 | 78.08 | 78.77 | 79.21 | 79.08 |
| 67 | −28.62 | −32.21 | −31.6 | 36.93 | 38.53 | 38.37 | 37.7 | 38.42 | 37.09 | 338.94 | 339.3 | 327.02 | 310.62 | 302.73 | 301.53 |
| 68 | 24.97 | 21.34 | 20.04 | 39.79 | 39.73 | 34.89 | 32.2 | 35.48 | 35.61 | 92.15 | 94.08 | 104.01 | 129.15 | 143.02 | 145.75 |
| 69 | −19.25 | −24.08 | −24.5 | 12.49 | 12.3 | 13.52 | 19.27 | 24.68 | 25.3 | 319.25 | 314.63 | 295 | 267.45 | 257.31 | 255.74 |
| 70 | 24.24 | 21.87 | 20.73 | 32.52 | 32.52 | 32.63 | 32.02 | 32.15 | 31.3 | 105.03 | 108.32 | 115.88 | 130.79 | 137.13 | 138.53 |
| 71 | −6.45 | −11.09 | −11.8 | 19.86 | 21.35 | 15.83 | 9.06 | 11.09 | 11.5 | 12.2 | 17.74 | 2.84 | 314.57 | 269.91 | 262.1 |
| 72 | −27.05 | −27.37 | −27 | 24 | 24.07 | 26.48 | 27.11 | 27.43 | 27.05 | 267.69 | 267.98 | 266.96 | 266.33 | 266.35 | 266.25 |
| 73 | −40.61 | −41.66 | −41.2 | 30.12 | 21.22 | 34.98 | 40.71 | 41.78 | 41.31 | 267.7 | 272.9 | 267.4 | 266.1 | 265.6 | 265.41 |
| 74 | −19.62 | −20.29 | −20.5 | 26.31 | 28.14 | 34.16 | 37.08 | 37.86 | 37.31 | 216.38 | 214.51 | 213.19 | 211.95 | 212.41 | 213.34 |
| 75 | −24.26 | −29.36 | −30.7 | 11.99 | 10.95 | 17.5 | 29.76 | 37.01 | 38.34 | 240.74 | 237.42 | 239.42 | 234.59 | 232.5 | 233.27 |
| 76 | 7.65 | 3.56 | 2.47 | 22.27 | 20.52 | 15.85 | 15.23 | 20.09 | 20.9 | 86.42 | 89.65 | 104.87 | 149.87 | 169.8 | 173.21 |
| 77 | −4.14 | −6.05 | −6.12 | 18.98 | 19.35 | 16.69 | 13.25 | 12.31 | 11.8 | 21.64 | 13.78 | 1.4 | 341.79 | 330.58 | 328.76 |
| 78 | 4.46 | 2.23 | 1.38 | 14.03 | 14.7 | 13.9 | 17.28 | 19.36 | 19.09 | 116.21 | 119.79 | 139.69 | 165.04 | 173.37 | 175.85 |
| 79 | 12.54 | 9.61 | 9.04 | 29.77 | 31.83 | 25.66 | 16.77 | 12.53 | 11.61 | 49.19 | 51.01 | 48.23 | 48.43 | 50.12 | 51.17 |
| 80 | −0.49 | −6.24 | −8.02 | 16.09 | 14.65 | 12.68 | 18.19 | 26.38 | 27.81 | 110.57 | 113.85 | 137.11 | 181.53 | 193.68 | 196.77 |
| 81 | 18.1 | 13.42 | 12.32 | 32.95 | 37.27 | 30.12 | 18.1 | 15.8 | 16.22 | 66.59 | 68.4 | 69.17 | 89.75 | 121.86 | 130.56 |
| 82 | −14.76 | −18.58 | −18.3 | 26.82 | 27.7 | 25.56 | 22.96 | 23.05 | 22.03 | 5.28 | 0.09 | 345.23 | 319.98 | 306.31 | 304.07 |
| 83 | 1.9 | 1.46 | 1.49 | 6.86 | 10.65 | 6.29 | 3.92 | 4.38 | 4.29 | 95.87 | 88.23 | 97.77 | 151.03 | 160.44 | 159.62 |
| 84 | −20.04 | −21.77 | −22.3 | 13.04 | 13.55 | 19.46 | 25.63 | 27.88 | 28.23 | 237.13 | 235.31 | 235.05 | 231.43 | 231.35 | 232 |
| 85 | 15.37 | 13.24 | 12.54 | 25.44 | 24.57 | 20.39 | 15.83 | 14.6 | 14.07 | 78.98 | 79.11 | 85.31 | 103.94 | 114.93 | 116.97 |
| 86 | 3.54 | −1.48 | −2.78 | 16.91 | 26.35 | 15.66 | 3.76 | 9.04 | 11.37 | 55.35 | 66.07 | 56.7 | 109.78 | 189.4 | 194.17 |
| 87 | 29.21 | 28.7 | 26.9 | 27.99 | 40.6 | 42.84 | 43.6 | 42.9 | 40.59 | 151.83 | 140.35 | 138.7 | 137.93 | 138.01 | 138.48 |

-continued

| | | | | | | | | | | | | | | | |
|---|---|---|---|---|---|---|---|---|---|---|---|---|---|---|---|
| 88 | −15.29 | −16.94 | −16.1 | 49.09 | 49.65 | 44.39 | 37.28 | 34.95 | 33.2 | 341.49 | 341.47 | 339.8 | 335.79 | 331.01 | 331.02 |
| 89 | 33.12 | 29.23 | 28.71 | 49.93 | 52.37 | 43.99 | 33.23 | 29.86 | 29.45 | 82.86 | 82.95 | 85.63 | 94.6 | 101.82 | 102.89 |
| 90 | 7.78 | 5.22 | 4.83 | 43.96 | 46.24 | 41.34 | 31.23 | 26.69 | 25.41 | 22.67 | 24.97 | 18.89 | 14.43 | 11.29 | 10.95 |
| 91 | 45.08 | 42.47 | 40.99 | 62.2 | 61.55 | 55.43 | 50.03 | 49.09 | 47.49 | 97.4 | 100.04 | 105.8 | 115.69 | 120.1 | 120.34 |
| 92 | −24.23 | −24.72 | −23.5 | 1.28 | 18.97 | 24.48 | 27.17 | 27.78 | 26.39 | 127.23 | 245.48 | 244.48 | 243.11 | 242.84 | 243.02 |
| 93 | 18.3 | 18.24 | 17.83 | 16.64 | 15.84 | 19.12 | 20.55 | 20.49 | 20.07 | 118.25 | 114.85 | 116.84 | 117.08 | 117.12 | 117.29 |
| 94 | −8.75 | −12.87 | −14.2 | 11.72 | 13.13 | 17.55 | 31.27 | 38.73 | 39.35 | 152.4 | 153.73 | 180.3 | 196.24 | 199.41 | 201.07 |
| 95 | −23.01 | −27.39 | −27.9 | 22.81 | 23.77 | 23.47 | 24.65 | 27.66 | 27.97 | 326.59 | 329.55 | 315.29 | 291.02 | 278 | 275.33 |
| 96 | −27.45 | −27.88 | −27.9 | 35.17 | 34.96 | 35.72 | 35.65 | 35.85 | 35.53 | 232.86 | 231.69 | 231.08 | 230.34 | 231.03 | 231.81 |
| 97 | −4.97 | −9.64 | −10.6 | 10.18 | 10.07 | 3.38 | 9.24 | 17.08 | 18.39 | 57.5 | 59.88 | 68.39 | 212.54 | 214.37 | 215.11 |
| 98 | 7.91 | 2.71 | 1.55 | 32.22 | 31.25 | 23.51 | 10.29 | 2.71 | 2.43 | 50.34 | 48.77 | 46.3 | 50.19 | 93.44 | 140.49 |
| 99 | −17.91 | −19.99 | −20.1 | 10.8 | 11.88 | 14.55 | 17.97 | 20 | 20.15 | 312.81 | 309.74 | 292.95 | 274.65 | 269.06 | 267.77 |
| 100 | 0.54 | −1.92 | −2.27 | 22.19 | 24.63 | 20.63 | 14.3 | 11.32 | 10.42 | 16.19 | 21.91 | 12.42 | 2.18 | 350.24 | 347.43 |
| 101 | −21.23 | −11.47 | −8.37 | 40.17 | 44.14 | 39.02 | 21.3 | 11.54 | 8.76 | 286.66 | 291.88 | 283.72 | 274.8 | 263.65 | 252.85 |
| 102 | 1.46 | 6.04 | 7.75 | 47.53 | 47.02 | 48.55 | 43.39 | 42.31 | 42.2 | 349.15 | 357.93 | 351.05 | 1.92 | 8.21 | 10.58 |
| 103 | −3.43 | 7.08 | 8.67 | 58.44 | 52.56 | 44.6 | 37.87 | 40.16 | 40.53 | 221.13 | 215.84 | 209.55 | 185.2 | 169.85 | 167.65 |
| 104 | −5.28 | −5.15 | −5.45 | 12.15 | 9.56 | 6.95 | 8.28 | 8.73 | 8.97 | 291.99 | 289.65 | 251.83 | 219.58 | 216.1 | 217.41 |
| 105 | −23.44 | −18.27 | −17.1 | 39.19 | 40.77 | 36.33 | 25.29 | 20.52 | 19.71 | 254.05 | 258.98 | 252.97 | 247.97 | 242.88 | 239.97 |
| 106 | −12.73 | −9.54 | −9.39 | 45.38 | 50.89 | 44.49 | 39.52 | 38.71 | 37.54 | 233.59 | 215.77 | 210.51 | 198.79 | 194.27 | 194.49 |
| 107 | 7.39 | 15.51 | 17.04 | 21.96 | 19.57 | 15.46 | 14.78 | 19.59 | 20.48 | 316.25 | 322.69 | 339.92 | 30.01 | 52.35 | 56.33 |
| 108 | −16.57 | −13.31 | −12.1 | 36.85 | 37.48 | 34.47 | 25.2 | 21.83 | 20.57 | 311.45 | 314.82 | 313.33 | 318.9 | 322.42 | 323.96 |
| 109 | 7.42 | 14.62 | 16.18 | 30.93 | 35.35 | 33.98 | 33.22 | 35.06 | 35.11 | 344.25 | 341.59 | 350.73 | 12.91 | 24.65 | 27.44 |
| 110 | −10.18 | −6.67 | −5.88 | 27.97 | 25.81 | 21.21 | 14.46 | 12.75 | 12.45 | 244.79 | 243.89 | 241.1 | 224.75 | 211.51 | 208.17 |
| 111 | −3.85 | 2.59 | 3.25 | 31.22 | 29.54 | 22.85 | 18.85 | 20.69 | 21.01 | 261.12 | 245.99 | 230.17 | 191.79 | 172.81 | 171.1 |
| 112 | −15.67 | −16.11 | −16.7 | 31.21 | 28.64 | 35.99 | 38.75 | 39.38 | 39.47 | 212.94 | 218.38 | 207.37 | 203.86 | 204.15 | 205.09 |
| 113 | −25.22 | −23.41 | −22.3 | 37.03 | 38.76 | 32.93 | 26.06 | 24.18 | 22.98 | 290.93 | 290.21 | 286.91 | 284.57 | 284.51 | 284.05 |
| 114 | −14.23 | −3.63 | −0.11 | 35.5 | 37.04 | 38.96 | 23.46 | 15.25 | 13.99 | 312.86 | 327.38 | 313.14 | 322.65 | 346.24 | 359.57 |
| 115 | −4.1 | −4.69 | −4.26 | 31.49 | 27.51 | 37.11 | 41.84 | 42.87 | 42.91 | 357.47 | 3.12 | 356.07 | 354.38 | 353.72 | 354.3 |
| 116 | 5.14 | 9.58 | 10.18 | 16.91 | 16.36 | 13.5 | 14.27 | 16.86 | 17.18 | 217.61 | 214.94 | 200.51 | 158.9 | 145.4 | 143.66 |
| 117 | 16.17 | 26.34 | 29.02 | 45.98 | 50.01 | 47.97 | 47.39 | 50.76 | 51.63 | 357.25 | 354.88 | 0.55 | 19.95 | 31.26 | 34.2 |
| 118 | 24.24 | 37.53 | 40.98 | 12.03 | 12.89 | 14.4 | 26.91 | 39.22 | 42.47 | 14.78 | 12.2 | 31.3 | 64.24 | 73.13 | 74.8 |
| 119 | −5.08 | 3.58 | 4.89 | 44.86 | 40.76 | 34.23 | 28.52 | 30.28 | 30.61 | 232.8 | 227.08 | 218.65 | 190.26 | 173.2 | 170.8 |
| 120 | 10.81 | 13.8 | 14.54 | 27.59 | 28.2 | 30.38 | 33.29 | 34.41 | 34.34 | 0.34 | 3.61 | 5.88 | 18.94 | 23.64 | 25.05 |

| DW1 Yellow | DW2 Magenta | DW3 Cyan | DW4 Ag | DW5 Yellow | DW6 Magenta | DW7 Cyan |
|---|---|---|---|---|---|---|
| 100 | 0 | 0 | 0 | 0 | 0 | 67 |
| 50 | 0 | 0 | 67 | 0 | 33 | 33 |
| 100 | 0 | 0 | 0 | 0 | 33 | 33 |
| 100 | 0 | 0 | 67 | 0 | 0 | 33 |
| 100 | 0 | 0 | 67 | 0 | 67 | 67 |
| 100 | 0 | 0 | 33 | 0 | 33 | 67 |
| 50 | 0 | 0 | 0 | 0 | 0 | 0 |
| 50 | 0 | 0 | 0 | 0 | 67 | 67 |
| 50 | 0 | 0 | 33 | 0 | 0 | 67 |
| 100 | 0 | 0 | 33 | 0 | 0 | 100 |
| 100 | 0 | 0 | 0 | 0 | 100 | 0 |
| 100 | 0 | 0 | 100 | 0 | 0 | 0 |
| 100 | 0 | 0 | 100 | 0 | 100 | 33 |
| 50 | 0 | 0 | 33 | 0 | 33 | 0 |
| 50 | 0 | 0 | 67 | 0 | 67 | 0 |
| 100 | 0 | 0 | 0 | 0 | 67 | 0 |
| 50 | 0 | 0 | 33 | 0 | 67 | 33 |
| 50 | 0 | 0 | 100 | 0 | 33 | 100 |
| 50 | 0 | 0 | 67 | 0 | 100 | 100 |
| 50 | 0 | 0 | 100 | 0 | 67 | 67 |
| 50 | 0 | 0 | 33 | 0 | 100 | 67 |
| 100 | 0 | 0 | 0 | 0 | 0 | 33 |
| 50 | 0 | 0 | 67 | 0 | 67 | 33 |
| 100 | 0 | 0 | 33 | 0 | 0 | 0 |
| 100 | 0 | 0 | 0 | 0 | 33 | 67 |
| 50 | 0 | 0 | 33 | 0 | 33 | 33 |
| 100 | 0 | 0 | 67 | 0 | 0 | 67 |
| 100 | 0 | 0 | 0 | 0 | 67 | 100 |
| 50 | 0 | 0 | 67 | 0 | 33 | 0 |
| 50 | 0 | 0 | 0 | 0 | 0 | 100 |
| 50 | 50 | 0 | 100 | 0 | 0 | 100 |
| 100 | 100 | 0 | 100 | 0 | 0 | 100 |
| 100 | 50 | 0 | 100 | 0 | 0 | 67 |
| 50 | 100 | 0 | 100 | 0 | 0 | 67 |
| 100 | 50 | 0 | 67 | 0 | 0 | 0 |
| 50 | 100 | 0 | 33 | 0 | 0 | 0 |
| 50 | 50 | 0 | 0 | 0 | 0 | 33 |
| 100 | 100 | 0 | 0 | 0 | 0 | 33 |
| 100 | 100 | 0 | 33 | 0 | 0 | 67 |

-continued

| | | | | | | | |
|---|---|---|---|---|---|---|---|
| 50 | 50 | 0 | 67 | 0 | 0 | 0 | 100 |
| 50 | 100 | 0 | 67 | 0 | 0 | 0 | 0 |
| 100 | 50 | 0 | 0 | 0 | 0 | 0 | 0 |
| 50 | 50 | 0 | 33 | 0 | 0 | 0 | 67 |
| 50 | 100 | 0 | 0 | 0 | 0 | 0 | 0 |
| 100 | 50 | 0 | 33 | 0 | 0 | 0 | 0 |
| 100 | 100 | 0 | 67 | 0 | 0 | 0 | 100 |
| 50 | 50 | 0 | 100 | 0 | 0 | 0 | 33 |
| 100 | 100 | 0 | 100 | 0 | 0 | 0 | 33 |
| 50 | 100 | 0 | 0 | 0 | 0 | 0 | 100 |
| 50 | 50 | 0 | 33 | 0 | 0 | 0 | 33 |
| 100 | 0 | 50 | 100 | 0 | 100 | 0 | 0 |
| 50 | 0 | 100 | 100 | 0 | 100 | 0 | 0 |
| 50 | 0 | 50 | 33 | 0 | 33 | 0 | 0 |
| 100 | 0 | 100 | 0 | 0 | 33 | 0 | 0 |
| 100 | 0 | 50 | 67 | 0 | 0 | 0 | 0 |
| 50 | 0 | 100 | 67 | 0 | 0 | 0 | 0 |
| 50 | 0 | 100 | 33 | 0 | 100 | 0 | 0 |
| 100 | 0 | 100 | 33 | 0 | 33 | 0 | 0 |
| 50 | 0 | 50 | 67 | 0 | 33 | 0 | 0 |
| 50 | 0 | 100 | 0 | 0 | 67 | 0 | 0 |

| Test field # | L-15 | L15 | L25 | L45 | L75 | L110 | a-15 | a15 | a25 | a45 | a75 | a110 | b-15 | b15 | b25 |
|---|---|---|---|---|---|---|---|---|---|---|---|---|---|---|---|
| 121 | 60.98 | 60.29 | 58.94 | 58.15 | 57.35 | 53.69 | −41.43 | −43.97 | −46.77 | −47.93 | −47.68 | −46.5 | 29.81 | 35.4 | 42.07 |
| 122 | 90.72 | 107.47 | 76.48 | 51.6 | 45 | 42.82 | 1.01 | 2.04 | 1.38 | 0.97 | 0.56 | 0.34 | −9.48 | −10.77 | −7.7 |
| 123 | 63.81 | 69.94 | 57.86 | 56.36 | 55.72 | 52.83 | −2.56 | −2.15 | −4.71 | −5.18 | −5.21 | −5.19 | 29.8 | 29.65 | 43.89 |
| 124 | 122.39 | 110.55 | 80.76 | 57.69 | 51.07 | 47.71 | −13.02 | −13.39 | −14.49 | −16.24 | −17.1 | −16.83 | −6.46 | −4.47 | 4.83 |
| 125 | 86.72 | 70.31 | 51.41 | 32.83 | 27.29 | 24.34 | 5.24 | 3.77 | 2.15 | −0.6 | −2.13 | −2.58 | −22.48 | −20.83 | −15.21 |
| 126 | 86.78 | 71.3 | 55.44 | 41.76 | 37.97 | 34.71 | −11.46 | −12.52 | −14.34 | −17.46 | −18.77 | −18.67 | −16.69 | −11.49 | −2.72 |
| 127 | 91.49 | 91.23 | 92.59 | 92.13 | 92.35 | 89.94 | −3.64 | −3.66 | −3.62 | −3.56 | −3.47 | −3.3 | 43.04 | 42.67 | 45.41 |
| 128 | 47.95 | 44.65 | 40.05 | 38.11 | 37.46 | 34.58 | 1.96 | 1.96 | 0.44 | −0.21 | −0.28 | −0.46 | −10.55 | −10.58 | −10.93 |
| 129 | 87.97 | 93.77 | 71.41 | 56.18 | 52.25 | 49.49 | −26.81 | −26.66 | −27.85 | −29.88 | −30.41 | −30.21 | −16.97 | −18.06 | −11.09 |
| 130 | 82.45 | 76.51 | 59.19 | 44.75 | 40.66 | 37.13 | −44.79 | −45.86 | −46.9 | −51.18 | −53.84 | −53.97 | −28.36 | −24.75 | −12.72 |
| 131 | 52.82 | 73.99 | 50.24 | 44.98 | 44.28 | 42.76 | 48.19 | 35.59 | 55.85 | 62.48 | 63.58 | 63.18 | 30.03 | 39.19 | 38.76 |
| 132 | 145.88 | 130.5 | 97.48 | 66.33 | 58.13 | 55.58 | −2.48 | −2.13 | −2.06 | −3.31 | −3.86 | −3.89 | 3.25 | 9.94 | 14.89 |
| 133 | 92.76 | 66.81 | 47.02 | 30.1 | 24.52 | 21.36 | 35.89 | 36.83 | 32.68 | 26.7 | 24.17 | 23.15 | −17.88 | −17.09 | −10.88 |
| 134 | 103.29 | 90.83 | 74.45 | 60.68 | 57.48 | 54.7 | 12.46 | 13.49 | 14.89 | 15.56 | 15.63 | 15.42 | 4.42 | 6.65 | 11.22 |
| 135 | 116.09 | 82.03 | 63.79 | 47.03 | 42.62 | 39.51 | 25.1 | 28.02 | 29.07 | 29.57 | 29.52 | 28.69 | 1.44 | 0.4 | 3.13 |
| 136 | 80.86 | 57.61 | 55.99 | 54.47 | 53.79 | 49.8 | 26.94 | 40.06 | 42.44 | 43.18 | 42.94 | 41.39 | 32.29 | 49.66 | 54.08 |
| 137 | 82.67 | 82.43 | 57.48 | 42.3 | 38.52 | 35.81 | 14.91 | 15.19 | 15.15 | 14.91 | 14.5 | 13.99 | −10.26 | −9.49 | −7.69 |
| 138 | 89.59 | 83.35 | 58.01 | 36.63 | 30.08 | 26.82 | −27.73 | −26.89 | −24.76 | −21.59 | −21.47 | −21.52 | −39.04 | −38.73 | −31.47 |
| 139 | 70.49 | 55.34 | 38.16 | 22.26 | 17.35 | 14.3 | 12.13 | 11.47 | 8.65 | 5.64 | 5.04 | 4.52 | −38.37 | −38.62 | −34.01 |
| 140 | 77.37 | 92.01 | 61.52 | 35.74 | 28.06 | 25.27 | 3.6 | 5.73 | 4.01 | 3.25 | 2.35 | 1.76 | −26.43 | −26.52 | −23.82 |
| 141 | 65.95 | 57.15 | 40.62 | 27.66 | 24.06 | 21.29 | 20.68 | 21.83 | 20.27 | 18.18 | 17.68 | 17.15 | −25.78 | −25.17 | −22.69 |
| 142 | 72.58 | 72.66 | 72.04 | 71.36 | 70.85 | 67.44 | −24.92 | −25.67 | −26.79 | −27.2 | −27.05 | −26.49 | 52.06 | 56.8 | 63.65 |
| 143 | 92.73 | 103.71 | 65.47 | 41.69 | 35.3 | 32.72 | 15.49 | 16.34 | 14.89 | 14.43 | 13.94 | 13.44 | −8.76 | −8.23 | −11.5 |
| 144 | 121.67 | 105.3 | 87.57 | 72.89 | 69.15 | 66.03 | −2.87 | −2.73 | −3.02 | −3.6 | −3.71 | −3.48 | 14.61 | 21.03 | 33.69 |
| 145 | 49.6 | 49.57 | 46.7 | 45.03 | 44.42 | 41.53 | −19.19 | −20.01 | −24.44 | −26.5 | −26.62 | −26.18 | 15.28 | 17.93 | 25.49 |
| 146 | 114 | 81.59 | 63.75 | 51.73 | 48.64 | 45.24 | 2.56 | 1.58 | 0.66 | −0.18 | −0.45 | −0.5 | −5.67 | −6.45 | −1.28 |
| 147 | 106.6 | 102.34 | 73.41 | 50.27 | 43.64 | 40.35 | −26.69 | −27.19 | −26.34 | −27.95 | −29.5 | −29.37 | −19.78 | −17.55 | −7.75 |
| 148 | 39.58 | 49.35 | 34.12 | 28.66 | 27.7 | 25.56 | −9.79 | −2.27 | −18.66 | −29.36 | −31.46 | −32.25 | −3.66 | −6 | 2.07 |
| 149 | 106.71 | 107.49 | 81.28 | 57.67 | 51.55 | 49.24 | 12.21 | 12.53 | 13.32 | 13.59 | 13.58 | 13.34 | 1.74 | 2.79 | 5.53 |
| 150 | 66.14 | 54.77 | 54.61 | 53.8 | 52.73 | 47.8 | −33.28 | −51.13 | −53.77 | −54.75 | −54.48 | −52.2 | −13.89 | −10.42 | −9.72 |
| 151 | 101.58 | 89.13 | 62.34 | 37.21 | 28.56 | 24.81 | −40.09 | −38.2 | −28.77 | −18.3 | −14.71 | −14.18 | −39.1 | −37.27 | −30.51 |
| 152 | 98.86 | 79.78 | 54.71 | 29.05 | 17.74 | 13.31 | −40.26 | −38.4 | −28.4 | −14.27 | −5.77 | −4.02 | −43.84 | −38.43 | −30.58 |
| 153 | 102.51 | 95.03 | 68.97 | 41.02 | 30.91 | 27.3 | −21.33 | −21.75 | −17.22 | −11.08 | −8.61 | −8.04 | −24.92 | −22.79 | −17.33 |
| 154 | 95.23 | 111.33 | 76.73 | 39.8 | 24.93 | 20.76 | −19.43 | −20.23 | −15.49 | −2.4 | 7.46 | 9.99 | −25.32 | −26.44 | −22.88 |
| 155 | 120.93 | 113.61 | 81.98 | 54.58 | 46.07 | 43.04 | 3.23 | 3.63 | 7.7 | 14.75 | 18.35 | 18.86 | 4.36 | 3.75 | 9.33 |
| 156 | 111.24 | 89.53 | 67.44 | 45.88 | 39.05 | 35.79 | 10.38 | 14.94 | 23.88 | 38.69 | 45.64 | 45.62 | −0.82 | 1.14 | 3.22 |
| 157 | 58.61 | 54.83 | 52.48 | 51.07 | 50.56 | 47.39 | 8.02 | 8.81 | 8.93 | 8.91 | 8.91 | 8.69 | 1.85 | 3.64 | 4.81 |
| 158 | 51.04 | 40.31 | 36.32 | 33.19 | 32.44 | 29.93 | 23.79 | 29.85 | 34.8 | 37.45 | 38.17 | 37.39 | 7.19 | 14.43 | 20.4 |
| 159 | 96.74 | 78.68 | 54.86 | 31.5 | 23.08 | 19.56 | −12.9 | −11.75 | −6.03 | 5.42 | 12.34 | 13.34 | −23.03 | −19.4 | −14.12 |
| 160 | 92.17 | 77.36 | 55.93 | 35.75 | 29.02 | 25.42 | −39.59 | −36.94 | −28.56 | −20.4 | −17.91 | −17.39 | −38.94 | −35.33 | −29.07 |
| 161 | 114.02 | 111.53 | 80.89 | 48.38 | 37.15 | 34.02 | 6.29 | 6.68 | 13.01 | 27.16 | 36.95 | 38.74 | −0.73 | −0.48 | 1.06 |
| 162 | 66.3 | 64.17 | 63.77 | 62.58 | 62.25 | 59.2 | 27.79 | 28.72 | 30.75 | 30.84 | 30.49 | 29.49 | 47.29 | 52.76 | 58.08 |
| 163 | 88.72 | 92.13 | 66.08 | 43 | 36.15 | 33.11 | −18.97 | −18.7 | −15.23 | −9.49 | −7.3 | −6.95 | −22.4 | −21.84 | −17.96 |
| 164 | 53.77 | 55.15 | 50.63 | 47.8 | 46.94 | 44.99 | 51.78 | 53.69 | 59.57 | 63.09 | 63.98 | 63.36 | 14.97 | 16.57 | 17.44 |
| 165 | 117.07 | 97.07 | 73.41 | 55.25 | 49.81 | 46.36 | 4.91 | 7.44 | 12.45 | 19.02 | 21.42 | 21.27 | 6.35 | 8.98 | 16.86 |
| 166 | 85.41 | 89.62 | 59.94 | 30.88 | 18.72 | 14.42 | −35.31 | −34.89 | −28.67 | −14.69 | −6.94 | −5.6 | −37.59 | −37.95 | −30.75 |
| 167 | 106.98 | 114.86 | 80.52 | 48.79 | 38.1 | 35.02 | −8.93 | −9.28 | −5.73 | 0.6 | 4.2 | 4.95 | −12.63 | −13.34 | −10.04 |
| 168 | 128.58 | 98.48 | 70.4 | 40.25 | 28.74 | 24.94 | −8.8 | −6.7 | −1.13 | 9.39 | 17.11 | 18.4 | −14.84 | −11.04 | −8.1 |
| 169 | 38.29 | 30.33 | 24.69 | 20.99 | 19.84 | 17.22 | 4.97 | 4.94 | 3.29 | 2.37 | 2.35 | 2 | −21.84 | −22.74 | −24.78 |
| 170 | 105.08 | 85.69 | 66.41 | 47.94 | 42.57 | 39.31 | −5.81 | −4.7 | −0.92 | 4.19 | 6.35 | 6.66 | −10.95 | −8.56 | −5.55 |
| 171 | 72.48 | 73.83 | 51.74 | 30.52 | 22.87 | 19.66 | 43.87 | 44.17 | 39.56 | 29.39 | 24.07 | 22.45 | −11.35 | −8.18 | −7.87 |
| 172 | 74.54 | 79.22 | 52.7 | 28.74 | 19.63 | 16.27 | 45.18 | 48 | 40.22 | 26.8 | 18.75 | 16.36 | −14.39 | −13.37 | −13.76 |
| 173 | 93.13 | 114.8 | 79.54 | 51.69 | 44.03 | 41.72 | 4.96 | 7.18 | 4.26 | −2.14 | −5.58 | −6.45 | −1.9 | 3.7 | −1.97 |

-continued

| | | | | | | | | | | | | | | |
|---|---|---|---|---|---|---|---|---|---|---|---|---|---|---|
| 174 | 46.12 | 48.87 | 41.54 | 38.92 | 38.05 | 35.41 | −29.74 | −28.35 | −41.91 | −48.93 | −50.41 | −50.52 | 10.69 | 12.67 | 15.76 |
| 175 | 122.56 | 114.73 | 82.31 | 55.02 | 46.78 | 43.49 | −6.18 | −7.16 | −10.74 | −19.39 | −24.16 | −24.54 | 3.27 | 4.47 | 9.4 |
| 176 | 118.67 | 119.59 | 86.41 | 52.23 | 40.85 | 37.32 | −6.31 | −6.64 | −9.73 | −20.36 | −29.32 | −30.87 | −3.84 | −3.13 | −4.03 |
| 177 | 64.59 | 88.55 | 51.52 | 28.21 | 20.71 | 17.88 | 33.17 | 32.25 | 32.78 | 21.29 | 13.85 | 11.83 | −11.68 | 4.33 | −13.98 |
| 178 | 92.04 | 93.04 | 66.06 | 41.04 | 32.82 | 29.56 | −0.49 | 0.46 | −4.74 | −17.9 | −28.11 | −30.25 | −3.12 | −0.83 | 0.05 |
| 179 | 108.9 | 101.81 | 72.01 | 47.49 | 39.9 | 36.81 | 7.84 | 8.49 | 5.49 | −0.26 | −3.37 | −4.11 | −2.62 | −3.07 | −2.05 |
| 180 | 53.85 | 40.4 | 35.07 | 31.87 | 30.92 | 27.86 | −4.36 | −9.19 | −13.1 | −15.85 | −16.41 | −15.91 | −6.78 | −12.75 | −18.19 |

| Test field # | b45 | b75 | b110 | C-15 | C15 | C25 | C45 | C75 | C110 | h-15 | h15 | h25 | h45 | h75 | h110 |
|---|---|---|---|---|---|---|---|---|---|---|---|---|---|---|---|
| 121 | 45.71 | 45.99 | 44.04 | 51.04 | 56.45 | 62.91 | 66.23 | 66.25 | 64.04 | 144.26 | 141.16 | 138.03 | 136.36 | 136.03 | 136.56 |
| 122 | 1.5 | 5.48 | 6.2 | 9.53 | 10.96 | 7.82 | 1.79 | 5.51 | 6.21 | 276.08 | 280.72 | 280.17 | 57.27 | 84.14 | 86.84 |
| 123 | 48.14 | 49.05 | 48.1 | 29.91 | 29.73 | 44.15 | 48.42 | 49.33 | 48.38 | 94.9 | 94.16 | 96.13 | 96.14 | 96.06 | 96.16 |
| 124 | 23.68 | 35.32 | 36.88 | 14.54 | 14.12 | 15.28 | 28.71 | 39.24 | 40.53 | 206.38 | 198.46 | 161.58 | 124.44 | 115.83 | 114.53 |
| 125 | −1.04 | 7.66 | 9.81 | 23.08 | 21.17 | 15.36 | 1.21 | 7.95 | 10.14 | 283.11 | 280.25 | 278.05 | 239.87 | 105.57 | 104.72 |
| 126 | 13.18 | 21.13 | 21.85 | 20.24 | 16.99 | 14.59 | 21.88 | 28.27 | 28.74 | 235.53 | 222.55 | 190.74 | 142.96 | 131.62 | 130.52 |
| 127 | 46.22 | 46.28 | 46.2 | 43.19 | 42.82 | 45.55 | 46.36 | 46.41 | 46.32 | 94.83 | 94.9 | 94.55 | 94.41 | 94.29 | 94.09 |
| 128 | −11 | −11.24 | −11.2 | 10.73 | 10.76 | 10.94 | 11 | 11.25 | 11.23 | 280.53 | 280.49 | 272.29 | 268.92 | 268.56 | 267.64 |
| 129 | −1.81 | 0.97 | 0.64 | 31.73 | 32.2 | 29.98 | 29.93 | 30.42 | 30.22 | 212.33 | 214.12 | 201.71 | 183.47 | 178.18 | 178.78 |
| 130 | 7.26 | 16.27 | 16.89 | 53.01 | 52.11 | 48.59 | 51.69 | 56.24 | 56.15 | 212.34 | 208.35 | 195.17 | 171.93 | 163.19 | 162.62 |
| 131 | 44.75 | 45.4 | 45.97 | 56.78 | 52.94 | 67.99 | 76.86 | 78.12 | 78.13 | 31.93 | 47.75 | 34.76 | 35.61 | 35.53 | 36.04 |
| 132 | 34.14 | 48.25 | 51.1 | 4.09 | 10.17 | 15.03 | 34.3 | 48.4 | 51.25 | 127.42 | 102.08 | 97.89 | 95.54 | 94.57 | 94.36 |
| 133 | 1.99 | 10.42 | 12.62 | 40.09 | 40.6 | 34.44 | 26.78 | 26.32 | 26.37 | 333.52 | 335.1 | 341.59 | 4.27 | 23.32 | 28.6 |
| 134 | 18.66 | 21.05 | 21.46 | 13.22 | 15.05 | 18.64 | 24.29 | 26.22 | 26.43 | 19.53 | 26.25 | 37.01 | 50.17 | 53.4 | 54.31 |
| 135 | 10.27 | 13.11 | 13.91 | 25.14 | 28.03 | 29.24 | 31.31 | 32.3 | 31.88 | 3.28 | 0.81 | 6.15 | 19.15 | 23.95 | 25.87 |
| 136 | 56.35 | 56.78 | 55.16 | 42.05 | 63.8 | 68.75 | 70.99 | 71.19 | 68.96 | 50.17 | 51.11 | 51.88 | 52.54 | 52.9 | 53.12 |
| 137 | −0.84 | 1.64 | 2.14 | 18.1 | 17.91 | 16.99 | 14.94 | 14.59 | 14.15 | 325.48 | 328.01 | 333.1 | 356.79 | 6.45 | 8.71 |
| 138 | −20.04 | −15.16 | −14.4 | 47.89 | 47.15 | 40.04 | 29.46 | 26.28 | 25.88 | 234.61 | 235.23 | 231.81 | 222.86 | 215.22 | 213.73 |
| 139 | −25.22 | −22.29 | −21 | 40.24 | 40.28 | 35.09 | 25.84 | 22.85 | 21.52 | 287.54 | 286.54 | 284.26 | 282.6 | 282.75 | 282.12 |
| 140 | −14.82 | −10.74 | −9.69 | 26.68 | 27.14 | 24.16 | 15.17 | 11 | 9.85 | 277.76 | 282 | 279.55 | 282.39 | 282.34 | 280.28 |
| 141 | −17.08 | −15.46 | −14.5 | 33.05 | 33.32 | 30.42 | 24.94 | 23.49 | 22.45 | 308.75 | 310.94 | 311.77 | 316.79 | 318.83 | 319.81 |
| 142 | 67.01 | 67.75 | 66.14 | 57.71 | 62.33 | 69.06 | 72.32 | 72.95 | 71.25 | 115.58 | 114.32 | 112.83 | 112.09 | 111.76 | 111.83 |
| 143 | −3.88 | −0.36 | 0.43 | 17.79 | 18.3 | 18.81 | 14.94 | 13.94 | 13.45 | 330.52 | 333.28 | 322.31 | 344.95 | 358.5 | 1.84 |
| 144 | 55.93 | 66.79 | 67.58 | 14.89 | 21.2 | 33.82 | 56.05 | 66.9 | 67.67 | 101.11 | 97.39 | 95.12 | 93.68 | 93.18 | 92.94 |
| 145 | 29.77 | 30.48 | 29.42 | 24.52 | 26.87 | 35.31 | 39.85 | 40.47 | 39.38 | 141.47 | 138.14 | 133.8 | 131.67 | 131.13 | 131.67 |
| 146 | 5.36 | 7.28 | 7.31 | 6.22 | 6.64 | 1.44 | 5.37 | 7.3 | 7.32 | 294.31 | 283.78 | 297.34 | 91.88 | 93.57 | 93.92 |
| 147 | 11.4 | 22.8 | 24.45 | 33.22 | 32.36 | 27.46 | 30.18 | 37.28 | 38.22 | 216.54 | 212.84 | 196.39 | 157.8 | 142.3 | 140.22 |
| 148 | 7.72 | 8.75 | 8.18 | 10.45 | 6.42 | 18.77 | 30.35 | 32.65 | 33.27 | 200.51 | 249.3 | 173.67 | 165.27 | 164.46 | 165.77 |
| 149 | 14.51 | 18.79 | 19.8 | 12.33 | 12.84 | 14.43 | 19.88 | 23.18 | 23.87 | 8.11 | 12.55 | 22.55 | 46.89 | 54.15 | 56.02 |
| 150 | −9.13 | −9.92 | −10.6 | 36.06 | 52.18 | 54.64 | 55.51 | 55.38 | 53.27 | 202.66 | 191.52 | 190.25 | 189.47 | 190.32 | 191.47 |
| 151 | −20.65 | −16.51 | −15.7 | 56 | 53.37 | 41.93 | 27.59 | 22.11 | 21.18 | 224.28 | 224.3 | 226.68 | 228.46 | 228.3 | 227.97 |
| 152 | −20.3 | −15.35 | −13.8 | 59.53 | 54.33 | 41.73 | 24.81 | 16.39 | 14.37 | 227.44 | 225.02 | 227.12 | 234.9 | 249.4 | 253.74 |
| 153 | −5.4 | 3.01 | 5.37 | 32.8 | 31.5 | 24.43 | 12.32 | 9.12 | 9.67 | 229.44 | 226.33 | 225.18 | 206.01 | 160.73 | 146.26 |
| 154 | −15.88 | −12.99 | −11.9 | 31.92 | 33.29 | 27.63 | 16.07 | 14.98 | 15.51 | 232.49 | 232.58 | 235.91 | 261.4 | 299.86 | 310.09 |
| 155 | 22.75 | 33.72 | 35.89 | 5.43 | 5.22 | 12.1 | 27.11 | 38.39 | 40.55 | 53.47 | 45.89 | 50.46 | 57.03 | 61.44 | 62.28 |
| 156 | 8.39 | 11.08 | 12.1 | 10.41 | 14.98 | 24.09 | 39.59 | 46.96 | 47.2 | 355.48 | 4.35 | 7.68 | 12.24 | 13.65 | 14.85 |
| 157 | 5.27 | 5.08 | 4.86 | 8.23 | 9.53 | 10.23 | 10.37 | 10.26 | 9.96 | 12.97 | 22.45 | 28.07 | 30.56 | 29.7 | 29.2 |
| 158 | 24.38 | 25.33 | 25.04 | 24.85 | 33.16 | 40.34 | 44.69 | 45.81 | 45 | 16.81 | 25.8 | 30.38 | 33.06 | 33.58 | 33.81 |
| 159 | −5.49 | 0.01 | 1.35 | 26.39 | 22.68 | 15.35 | 7.71 | 12.34 | 13.41 | 240.74 | 238.8 | 246.87 | 314.62 | 0.06 | 5.76 |
| 160 | −20.45 | −17.07 | −16.4 | 55.53 | 51.12 | 40.76 | 28.89 | 24.74 | 23.89 | 224.53 | 223.73 | 225.51 | 225.06 | 223.62 | 223.3 |
| 161 | 5.8 | 9.46 | 10.94 | 6.33 | 6.69 | 13.05 | 27.77 | 38.15 | 40.25 | 353.38 | 355.91 | 4.66 | 12.05 | 14.36 | 15.76 |
| 162 | 61.12 | 62.16 | 61.44 | 54.86 | 60.07 | 65.49 | 68.42 | 69.39 | 68.59 | 59.56 | 61.44 | 62.48 | 63.29 | 63.61 | 63.61 |
| 163 | −11.12 | −8.34 | −7.89 | 29.35 | 28.75 | 23.35 | 14.62 | 11.08 | 10.51 | 229.73 | 229.43 | 229.7 | 229.52 | 228.8 | 228.62 |
| 164 | 17.77 | 17.6 | 18.44 | 53.9 | 56.19 | 62.07 | 65.55 | 66.36 | 65.99 | 16.13 | 17.15 | 16.32 | 15.73 | 15.38 | 16.23 |
| 165 | 31.7 | 41.08 | 41.84 | 8.03 | 11.66 | 20.95 | 36.97 | 46.33 | 46.93 | 52.24 | 50.36 | 53.56 | 59.03 | 62.46 | 63.06 |
| 166 | −19.82 | −13.99 | −12.4 | 51.57 | 51.55 | 42.04 | 24.67 | 15.61 | 13.61 | 226.79 | 227.4 | 227 | 233.45 | 243.59 | 245.69 |
| 167 | −3.47 | 0.17 | 1.11 | 15.46 | 16.25 | 11.56 | 3.52 | 4.2 | 5.07 | 234.75 | 235.19 | 240.27 | 279.81 | 2.37 | 12.61 |
| 168 | −0.77 | 5.04 | 6.85 | 17.25 | 12.91 | 8.18 | 9.42 | 17.84 | 19.63 | 239.33 | 238.76 | 262.05 | 355.32 | 16.42 | 20.42 |
| 169 | −25.86 | −26.35 | −25.6 | 22.4 | 23.27 | 24.99 | 25.96 | 26.46 | 25.68 | 282.83 | 282.25 | 277.56 | 275.23 | 275.09 | 274.46 |
| 170 | 0.28 | 2.72 | 3.28 | 12.39 | 9.77 | 6.25 | 4.2 | 6.9 | 7.42 | 242.03 | 241.25 | 260.61 | 3.76 | 23.18 | 26.22 |
| 171 | 1.13 | 7.76 | 9.71 | 45.31 | 44.92 | 40.33 | 29.41 | 25.29 | 24.46 | 345.49 | 349.51 | 348.75 | 2.21 | 17.87 | 23.38 |
| 172 | −11.26 | −11.59 | −11.3 | 47.41 | 49.82 | 42.51 | 29.07 | 22.04 | 19.87 | 342.34 | 344.44 | 341.12 | 337.21 | 328.29 | 325.4 |
| 173 | 0.21 | 1.11 | 1.01 | 5.31 | 8.08 | 4.69 | 2.15 | 5.69 | 6.53 | 339.06 | 27.25 | 335.19 | 174.39 | 168.74 | 171.06 |
| 174 | 18.51 | 18.66 | 17.62 | 31.6 | 31.05 | 44.78 | 52.32 | 53.75 | 53.5 | 160.22 | 155.93 | 159.39 | 159.28 | 159.68 | 160.77 |
| 175 | 21.25 | 29.76 | 30.7 | 6.99 | 8.44 | 14.27 | 28.77 | 38.33 | 39.3 | 152.14 | 148.03 | 138.81 | 132.38 | 129.07 | 128.63 |
| 176 | −4.85 | −6.29 | −7.27 | 7.38 | 7.34 | 10.53 | 20.93 | 29.98 | 31.71 | 211.34 | 205.22 | 202.48 | 193.39 | 192.1 | 193.24 |
| 177 | −15.85 | −17.43 | −17.6 | 35.17 | 32.54 | 35.64 | 26.54 | 22.26 | 21.17 | 340.6 | 7.65 | 323.34 | 308.47 | 303.96 |
| 178 | 6.02 | 10.59 | 11.08 | 3.16 | 0.94 | 4.74 | 18.88 | 30.04 | 32.22 | 261.01 | 298.83 | 179.35 | 161.42 | 159.36 | 159.89 |
| 179 | 0.52 | 1.49 | 1.46 | 8.27 | 9.03 | 5.86 | 0.58 | 3.68 | 4.36 | 341.55 | 340.11 | 339.52 | 116.28 | 156.13 | 160.43 |
| 180 | −20.78 | −21.56 | −21 | 8.06 | 15.71 | 22.41 | 26.14 | 27.1 | 26.37 | 237.26 | 234.22 | 234.23 | 232.68 | 232.72 | 232.88 |

| DW1 Yellow | DW2 Magenta | DW3 Cyan | DW4 Ag | DW5 Yellow | DW6 Magenta | DW7 Cyan |
|---|---|---|---|---|---|---|
| 100 | 0 | 100 | 67 | 0 | 33 | 0 |
| 100 | 0 | 50 | 33 | 0 | 67 | 0 |
| 50 | 0 | 50 | 0 | 0 | 0 | 0 |
| 100 | 0 | 100 | 0 | 0 | 0 | 0 |
| 100 | 0 | 50 | 0 | 0 | 67 | 0 |
| 100 | 0 | 50 | 33 | 0 | 100 | 0 |
| 100 | 0 | 100 | 100 | 0 | 0 | 0 |
| 50 | 0 | 50 | 100 | 0 | 0 | 0 |
| 50 | 0 | 100 | 33 | 0 | 67 | 0 |
| 100 | 0 | 50 | 67 | 0 | 100 | 0 |
| 0 | 50 | 50 | 100 | 100 | 0 | 0 |
| 0 | 100 | 100 | 100 | 100 | 0 | 0 |
| 0 | 50 | 100 | 100 | 0 | 0 | 0 |
| 0 | 100 | 50 | 100 | 0 | 0 | 0 |
| 0 | 50 | 50 | 0 | 33 | 0 | 0 |
| 0 | 100 | 50 | 67 | 67 | 0 | 0 |
| 0 | 50 | 100 | 67 | 67 | 0 | 0 |
| 0 | 100 | 50 | 0 | 100 | 0 | 0 |
| 0 | 50 | 100 | 33 | 100 | 0 | 0 |
| 0 | 100 | 100 | 0 | 33 | 0 | 0 |
| 0 | 50 | 50 | 67 | 33 | 0 | 0 |
| 0 | 100 | 50 | 33 | 100 | 0 | 0 |
| 0 | 100 | 100 | 67 | 33 | 0 | 0 |
| 0 | 50 | 100 | 0 | 0 | 0 | 0 |
| 0 | 50 | 50 | 33 | 67 | 0 | 0 |
| 0 | 100 | 50 | 0 | 0 | 0 | 0 |
| 0 | 100 | 100 | 33 | 67 | 0 | 0 |
| 0 | 50 | 100 | 67 | 0 | 0 | 0 |
| 0 | 100 | 100 | 33 | 33 | 0 | 0 |
| 0 | 0 | 100 | 100 | 100 | 100 | 0 |
| 0 | 100 | 0 | 100 | 0 | 0 | 100 |
| 100 | 0 | 0 | 100 | 0 | 100 | 100 |
| 0 | 0 | 100 | 100 | 100 | 0 | 0 |
| 0 | 0 | 100 | 100 | 0 | 100 | 0 |
| 0 | 100 | 0 | 100 | 100 | 0 | 0 |
| 0 | 100 | 0 | 100 | 0 | 0 | 100 |
| 100 | 0 | 0 | 100 | 0 | 100 | 0 |
| 100 | 0 | 0 | 100 | 0 | 0 | 100 |
| 100 | 100 | 100 | 100 | 0 | 0 | 0 |

| Test field # | L-15 | L15 | L25 | L45 | L75 | L110 | a-15 | a15 | a25 | a45 | a75 | a110 | b-15 | b15 | b25 |
|---|---|---|---|---|---|---|---|---|---|---|---|---|---|---|---|
| 181 | 101.31 | 90.8 | 65.25 | 39.84 | 30.57 | 26.94 | 4.84 | 4.39 | -0.11 | -11.51 | -21.25 | -23.31 | -3.46 | -2.81 | -1.15 |
| 182 | 102.01 | 67.92 | 51.91 | 36.78 | 32.33 | 28.83 | 16.36 | 15.61 | 12.2 | 6.35 | 3.69 | 3.03 | 0.61 | 1.45 | 4.76 |
| 183 | 70.78 | 68.94 | 68.75 | 68.05 | 67.35 | 63.18 | -27.8 | -29.21 | -30.42 | -30.79 | -30.45 | -29.52 | 5.91 | 8.13 | 9.59 |
| 184 | 50.51 | 54.42 | 51.38 | 49.92 | 49.12 | 46.33 | -56.2 | -53.67 | -64.86 | -70.48 | -71.93 | -72.18 | 15.55 | 13.84 | 22.53 |
| 185 | 48.1 | 49.37 | 42.56 | 39.32 | 38.74 | 36.47 | 4.84 | 5.63 | 6.16 | 6.18 | 6.15 | 6.1 | 18.38 | 21.71 | 24.62 |
| 186 | 69.85 | 75.21 | 49.66 | 29.96 | 23.99 | 21.37 | 36.82 | 37.41 | 35.86 | 28.47 | 24.93 | 23.77 | -6.09 | -0.85 | -4.34 |
| 187 | 119.78 | 118.44 | 83.2 | 50.01 | 37.11 | 33.15 | -5.24 | -5.52 | -8.78 | -19.1 | -30.04 | -32.51 | 0.03 | -1.22 | 1.25 |
| 188 | 124.54 | 122.27 | 89.16 | 56.97 | 46.86 | 43.74 | -4.39 | -4.44 | -6.34 | -12.34 | -16.16 | -16.8 | -1.57 | 0.04 | 0.52 |
| 189 | 92.29 | 76.25 | 54.19 | 33.69 | 27.32 | 24.12 | 13.73 | 14.1 | 9.99 | 0.59 | -5.27 | -6.54 | -4.61 | -4.46 | -10.17 |
| 190 | 132.6 | 59.09 | 42.57 | 27.25 | 21.93 | 18.46 | 32.53 | 41.46 | 27.39 | 23.73 | 22.05 | 35.65 | 14.51 | -7.75 | -3.98 |
| 191 | 125.39 | 96.53 | 71.07 | 46.22 | 36.91 | 32.81 | -4.46 | -4.38 | -5.29 | -6.78 | -7.92 | -7.63 | 58.99 | 57.94 | 47.95 |
| 192 | 128.37 | 90.83 | 67 | 39.19 | 27.61 | 23.13 | -5.27 | -4.74 | -5.47 | -7.17 | -9.48 | -9.56 | 58.05 | 57.96 | 46.53 |
| 193 | 124.68 | 109.9 | 78.1 | 45.51 | 32.66 | 28.71 | -1.97 | -1.81 | -1.92 | -3.45 | -5.11 | -5.27 | -5.6 | -6.12 | -8.82 |
| 194 | 120.14 | 125.47 | 86.51 | 46.92 | 30.45 | 26.23 | 0.29 | 0.54 | 2.68 | 8.02 | 14.23 | 15.65 | -3.63 | -3.67 | -4.51 |
| 195 | 56.39 | 53.12 | 51.72 | 50.12 | 49.71 | 46.82 | 0.55 | 0.63 | 0.75 | 0.71 | 0.73 | 0.62 | -5.87 | -5 | -4.94 |
| 196 | 99.39 | 104.84 | 76.15 | 43.86 | 31.27 | 27.26 | -2.33 | -2.66 | -0.77 | 3.97 | 8.34 | 9.58 | 28.4 | 29.48 | 25.21 |
| 197 | 102.75 | 106.7 | 76.19 | 44.54 | 32.16 | 28.16 | -5.93 | -6.16 | -7.42 | -11.83 | -16.76 | -17.75 | 30.13 | 30.31 | 24.45 |
| 198 | 46.26 | 40.25 | 35.52 | 31.49 | 30.23 | 27.8 | 12.98 | 16.34 | 21.68 | 25.73 | 26.96 | 26.39 | 1.7 | 6.9 | 13.96 |
| 199 | 91.7 | 79.97 | 61.26 | 39.79 | 32.28 | 28.56 | -8.81 | -9.4 | -12.5 | -19.87 | -25.82 | -26.52 | 41.36 | 41.14 | 35.89 |
| 200 | 37.45 | 40.7 | 29.51 | 23.51 | 21.94 | 19.7 | 2.76 | 2.98 | 4.53 | 5.75 | 6.22 | 5.9 | -22.19 | -23.03 | -26.23 |
| 201 | 97 | 134.54 | 90.45 | 52.66 | 39.37 | 36.15 | -1.75 | -3.18 | -2.47 | -2.47 | -2.52 | -2.5 | 13.79 | 12.39 | 11.77 |
| 202 | 88.84 | 72.41 | 55.56 | 37.14 | 30.18 | 26.47 | -0.72 | 0.81 | 3.63 | 9.34 | 13.04 | 13.56 | 42.79 | 39.93 | 34.74 |
| 203 | 110.23 | 100.28 | 72.55 | 41.55 | 29.34 | 25.25 | -6.21 | -5.71 | -4.31 | -2.46 | -1.34 | -1.16 | 6.2 | 6.48 | 3.35 |
| 204 | 44.35 | 53.02 | 43.55 | 41.53 | 40.84 | 38.46 | -8.14 | -2.49 | -10.77 | -12.73 | -13.18 | -13.06 | -38.35 | -34.73 | -40.71 |
| 205 | 87.68 | 113.44 | 78.26 | 49.85 | 41.32 | 38.74 | -2.68 | -4.01 | -3.07 | -3.21 | -3.19 | -2.99 | 26.65 | 24.18 | 25.16 |
| 206 | 43.51 | 41.04 | 38.1 | 35.2 | 34.18 | 31.59 | 28.41 | 31.04 | 34.41 | 36.38 | 37.16 | 36.33 | -24.08 | -25.47 | -28.16 |
| 207 | 86.47 | 85.51 | 61.69 | 35.54 | 24.82 | 20.86 | -6.47 | -6.14 | -5.67 | -4.81 | -4.69 | -4.86 | 18.22 | 19.17 | 16.12 |
| 208 | 93.62 | 130.34 | 91.77 | 49.13 | 31.83 | 27.75 | 1.49 | 0.81 | 2.71 | 9.66 | 17.68 | 20.2 | -5 | -4.02 | -6.71 |
| 209 | 126.38 | 103.33 | 72.92 | 44.05 | 33.32 | 29.43 | -4.71 | -4.13 | -3.88 | -5.17 | -6.63 | -6.65 | -8.5 | -9.56 | -12.61 |
| 210 | 96.18 | 88.14 | 63.45 | 36.5 | 25.28 | 21.26 | -3.96 | -3.43 | -2.33 | -0.47 | 0.94 | 1.06 | 4.53 | 3.81 | 0.47 |
| 211 | 86.94 | 71.08 | 48.47 | 27.31 | 19.3 | 15.59 | 33.74 | 34.11 | 29.26 | 18.07 | 11.38 | 9.89 | 31.07 | 31.99 | 24.22 |

-continued

| | | | | | | | | | | | | | | |
|---|---|---|---|---|---|---|---|---|---|---|---|---|---|---|
| 212 | 87.55 | 70.18 | 50.13 | 28.18 | 19.7 | 15.71 | -50.19 | -50.03 | -43.33 | -28.37 | -20.62 | -18.35 | 17.33 | 19.34 | 15.65 |
| 213 | 76.03 | 51.58 | 32.94 | 18.25 | 13.01 | 9.93 | 15.16 | 12.37 | 7.19 | 1.07 | -1.3 | -2.11 | -42.88 | -41.2 | -32.22 |
| 214 | 106.34 | 116.51 | 84.41 | 51.3 | 39.17 | 35.29 | -8.17 | -8.09 | -12.19 | -22.83 | -32.99 | -35.18 | 62.51 | 64.62 | 53.75 |
| 215 | 88.24 | 78.3 | 53.14 | 30.63 | 22.67 | 19.41 | 47.61 | 48.66 | 39.99 | 26.91 | 20.18 | 18.08 | -15.88 | -16.66 | -17.24 |
| 216 | 133.95 | 97.61 | 71.24 | 45.85 | 36.16 | 32.31 | 0.08 | 2.76 | 6.47 | 15.23 | 21.18 | 22.02 | 68.69 | 62.45 | 51.31 |
| 217 | 88.41 | 97.36 | 65.83 | 34.22 | 20.88 | 16.55 | -36.56 | -38.66 | -26.95 | -8.4 | 3.57 | 6.18 | -40.36 | -41.71 | -35.89 |
| 218 | 74.4 | 94.08 | 63.28 | 39.51 | 32.21 | 29.87 | 49.47 | 52.05 | 49.96 | 43.67 | 41.27 | 40.69 | -8.06 | -5.66 | -4.99 |
| 219 | 103.5 | 86 | 62.26 | 41.2 | 34.25 | 30.31 | -43.48 | -43.6 | -38.33 | -36.54 | -37.95 | -37.95 | -40.16 | -34.24 | -23.04 |
| 220 | 122.88 | 108.8 | 76.57 | 41.86 | 25.68 | 20.85 | -2.12 | -1.55 | -1.07 | -0.99 | -1.1 | -1.15 | -2.09 | -2.49 | -2.32 |

| Test field # | b45 | b75 | b110 | C-15 | C15 | C25 | C45 | C75 | C110 | h-15 | h15 | h25 | h45 | h75 | h110 |
|---|---|---|---|---|---|---|---|---|---|---|---|---|---|---|---|
| 181 | 4.64 | 9.22 | 9.8 | 5.95 | 5.21 | 1.16 | 12.41 | 23.17 | 25.28 | 324.42 | 327.34 | 264.7 | 158.04 | 156.55 | 157.2 |
| 182 | 13.64 | 18.82 | 19.17 | 16.37 | 15.68 | 13.09 | 15.05 | 19.18 | 19.41 | 2.14 | 5.31 | 21.31 | 65.02 | 78.89 | 81.01 |
| 183 | 10.31 | 9.76 | 8.66 | 28.42 | 30.32 | 31.89 | 32.47 | 31.97 | 30.77 | 168 | 164.44 | 162.51 | 161.49 | 162.22 | 163.65 |
| 184 | 27.88 | 28.41 | 27.09 | 58.31 | 55.43 | 68.66 | 75.79 | 77.34 | 77.1 | 164.53 | 165.54 | 160.85 | 158.42 | 158.45 | 159.43 |
| 185 | 26.54 | 27.04 | 26.61 | 19.01 | 22.43 | 25.36 | 27.24 | 27.74 | 27.32 | 75.25 | 75.47 | 76.09 | 76.94 | 77.12 | 76.87 |
| 186 | 3.62 | 9.66 | 11.17 | 37.32 | 37.42 | 36.12 | 28.7 | 26.73 | 26.26 | 350.6 | 358.7 | 353.1 | 7.25 | 21.19 | 25.18 |
| 187 | 6.69 | 11.93 | 12.67 | 5.24 | 5.65 | 8.87 | 20.24 | 32.32 | 34.89 | 179.67 | 192.51 | 171.91 | 160.69 | 158.35 | 158.71 |
| 188 | 3.22 | 4.46 | 4.27 | 4.66 | 4.44 | 6.36 | 12.75 | 16.76 | 17.33 | 199.63 | 179.47 | 175.29 | 165.35 | 164.58 | 165.74 |
| 189 | -12.7 | -14.38 | -14.4 | 14.49 | 14.79 | 14.26 | 12.71 | 15.31 | 15.81 | 341.44 | 342.46 | 314.48 | 272.68 | 249.88 | 245.57 |
| 190 | 3.5 | 8.2 | 9.31 | 35.62 | 42.18 | 35.88 | 27.61 | 25.11 | 23.94 | 24.04 | 349.41 | 353.64 | 7.28 | 19.05 | 22.9 |
| 191 | 34.6 | 29.11 | 27.93 | 59.15 | 58.1 | 48.24 | 35.26 | 30.17 | 28.95 | 94.33 | 94.32 | 96.3 | 101.09 | 105.23 | 105.28 |
| 192 | 28.45 | 18.96 | 17.24 | 58.29 | 58.16 | 46.85 | 29.34 | 21.2 | 19.71 | 95.19 | 94.67 | 96.7 | 104.14 | 116.55 | 119 |
| 193 | -15.53 | -21.27 | -22.2 | 5.94 | 6.39 | 9.02 | 15.91 | 21.88 | 22.85 | 250.65 | 253.58 | 257.7 | 257.46 | 256.49 | 256.67 |
| 194 | -7.65 | -11.59 | -12.2 | 3.64 | 3.71 | 5.24 | 11.08 | 18.35 | 19.82 | 274.51 | 278.43 | 300.74 | 316.35 | 320.83 | 322.14 |
| 195 | -4.47 | -4.63 | -4.54 | 5.89 | 5.04 | 5 | 4.52 | 4.68 | 4.59 | 275.37 | 277.22 | 278.64 | 279.02 | 278.94 | 277.8 |
| 196 | 15.77 | 10.54 | 9.65 | 28.49 | 29.6 | 25.22 | 16.26 | 13.43 | 13.6 | 94.68 | 95.15 | 91.76 | 75.87 | 51.65 | 45.22 |
| 197 | 12.8 | 5.89 | 4.24 | 30.71 | 30.93 | 25.55 | 17.43 | 17.76 | 18.24 | 101.14 | 101.49 | 106.87 | 132.75 | 160.63 | 166.57 |
| 198 | 19.87 | 21.71 | 21.61 | 13.09 | 17.74 | 25.79 | 32.51 | 34.62 | 34.11 | 7.48 | 22.91 | 32.78 | 37.69 | 38.84 | 39.31 |
| 199 | 24.24 | 18.89 | 17.43 | 42.29 | 42.2 | 38.01 | 31.35 | 31.99 | 31.73 | 102.02 | 102.88 | 109.21 | 129.34 | 143.81 | 146.69 |
| 200 | -29.11 | -29.99 | -29.4 | 22.37 | 23.22 | 26.62 | 29.67 | 30.62 | 29.99 | 277.1 | 277.36 | 279.8 | 281.17 | 281.71 | 281.35 |
| 201 | 5.02 | 0.34 | -1.01 | 13.9 | 12.8 | 12.02 | 5.59 | 2.54 | 2.69 | 97.25 | 104.4 | 101.87 | 116.16 | 172.31 | 201.97 |
| 202 | 25.36 | 21.15 | 20.15 | 42.79 | 39.94 | 34.93 | 27.03 | 24.85 | 24.29 | 90.96 | 88.84 | 84.04 | 69.78 | 58.35 | 56.06 |
| 203 | -2.92 | -7.59 | -8.21 | 8.78 | 8.64 | 5.46 | 3.81 | 7.71 | 8.29 | 135.08 | 131.39 | 142.16 | 229.86 | 259.98 | 261.97 |
| 204 | -41.13 | -41.47 | -41.2 | 39.21 | 34.82 | 42.11 | 43.06 | 43.52 | 43.21 | 258.01 | 265.89 | 255.19 | 252.8 | 252.38 | 252.41 |
| 205 | 17.56 | 13.62 | 12.7 | 26.79 | 24.51 | 25.35 | 17.85 | 13.99 | 13.05 | 95.73 | 99.42 | 96.96 | 100.35 | 103.18 | 103.24 |
| 206 | -29.78 | -30.31 | -28.9 | 37.24 | 40.15 | 44.46 | 47.01 | 47.96 | 46.42 | 319.71 | 320.63 | 320.7 | 320.79 | 321.5 | |
| 207 | 6.83 | 0.47 | -0.83 | 19.33 | 20.12 | 17.09 | 8.35 | 4.72 | 4.93 | 109.55 | 107.75 | 109.36 | 125.14 | 174.24 | 189.68 |
| 208 | -10.3 | -15.33 | -16.7 | 5.22 | 4.1 | 7.23 | 14.12 | 23.4 | 26.2 | 286.63 | 281.4 | 292.04 | 313.17 | 319.07 | 320.44 |
| 209 | -19.95 | -25.13 | -25.6 | 9.72 | 10.41 | 13.19 | 20.61 | 25.99 | 26.43 | 240.99 | 246.62 | 252.88 | 255.49 | 255.23 | 255.43 |
| 210 | -7.3 | -13.26 | -14 | 6.01 | 5.13 | 2.38 | 7.32 | 13.29 | 14.08 | 131.13 | 131.98 | 168.49 | 266.28 | 274.06 | 274.3 |
| 211 | 13.54 | 8.25 | 7.15 | 45.87 | 46.77 | 37.98 | 22.59 | 14.05 | 12.2 | 42.64 | 43.16 | 39.62 | 36.84 | 35.94 | 35.88 |
| 212 | 7 | 2.43 | 1.07 | 53.1 | 53.64 | 46.07 | 29.22 | 20.76 | 18.38 | 160.95 | 158.86 | 160.14 | 166.15 | 173.29 | 176.66 |
| 213 | -17.94 | -10.64 | -8.3 | 45.48 | 43.02 | 33.01 | 17.97 | 10.71 | 8.57 | 289.46 | 286.71 | 282.58 | 273.41 | 263.05 | 255.74 |
| 214 | 35.37 | 26.97 | 25.48 | 63.05 | 65.12 | 55.12 | 42.1 | 42.62 | 43.44 | 97.45 | 97.13 | 102.78 | 122.85 | 140.73 | 144.09 |
| 215 | -18.16 | -20.42 | -19.7 | 50.19 | 51.43 | 43.55 | 32.46 | 28.71 | 26.75 | 341.56 | 341.1 | 336.68 | 325.99 | 314.65 | 312.53 |
| 216 | 38.46 | 33.59 | 32.87 | 68.69 | 62.51 | 51.72 | 41.36 | 39.71 | 39.57 | 89.93 | 87.47 | 82.81 | 68.39 | 57.77 | 56.19 |
| 217 | -29.13 | -28.62 | -28.3 | 54.46 | 56.87 | 44.88 | 30.31 | 28.84 | 28.98 | 227.83 | 227.18 | 233.09 | 253.92 | 277.11 | 282.31 |
| 218 | 10.28 | 21.37 | 24.68 | 50.12 | 52.35 | 50.21 | 44.86 | 46.48 | 47.59 | 350.75 | 353.8 | 354.29 | 13.24 | 27.37 | 31.24 |
| 219 | -3.85 | 7.15 | 8.76 | 59.19 | 55.43 | 44.72 | 36.74 | 38.62 | 38.94 | 222.73 | 218.14 | 211.01 | 186.01 | 169.32 | 166.99 |
| 220 | -1.49 | -0.6 | -0.24 | 2.98 | 2.94 | 2.56 | 1.79 | 1.25 | 1.17 | 224.67 | 238.11 | 245.25 | 236.51 | 208.53 | 191.61 |

Generating the Empirical Models of Second Order

For each of the responses L[-15], L[15], . . . L[110], a[-15) . . . a[110], and b[-15] . . . b[110] the coefficients β of the equation $$\text{response} = \beta_0 + \sum_{i=1}^{n} \beta_i \cdot x_i + \sum_{i=1}^{n} \sum_{j \geq i}^{n} \beta_{ij} \cdot x_i \cdot x_j$$

with the parameters being defined as above were determined by least-squares fit. It has been found useful to use a third order model for L responses. This evaluation provides not only the coefficients themselves but also the corresponding confidence intervals.

In the following equations Yu, Mu, Cu are the respective yellow, magenta and cyan ink layers b), that are applied on white OPP film, representing substrate a) in the sequence yellow, magenta and cyan before the silver effect pigment layer c) is printed. Yo, Mo and Co correspond to the ink layers c) that are applied according to the same sequence yellow, magenta and cyan above or on top of the silver effect pigment layer d).

For determination of the equations for the L-values, a Box-Cox Transformation was applied to achieve a better fit. The Box-Cox-Transformation is e.g. described in George E. P. Box, J. Stuart Hunter, William G. Hunter, "Statistics for Experimenters", Wiley 2005, ISBN-13: 978-0471718130, by George E. P. Box, Norman R. Draper: "Empirical Model-Building and Response Surfaces", Wiley 1987, ISBN-13: 978-0471810339, and by Peter Goos, Bradley Jones: "Optimal Design of Experiments—A Case Study Approach", Wiley 2011, ISBN-13:978-0470744611.

Regression analysis of L15 vs. Yu, Mu, Cu, Ag, Yo, Mo, Co:
Terms Yu*Yo, Mu*Mo and Cu*Co have been omitted.
Transformation: Box-Cox, λ=0,5

$$L15\wedge 0{,}5 = 8{,}994 + 0{,}00591Yu - 0{,}01291Mu -$$
$$0{,}01942Cu + 0{,}08571Ag + 0{,}00508Yo - 0{,}01569Mo -$$
$$0{,}02183Co - 0{,}000072Yu*Yu + 0{,}000068Cu*Cu -$$
$$0{,}001190Ag*Ag - 0{,}000084Yu*Mu + 0{,}000057Yu*Co +$$
$$0{,}000174Mu*Ag - 0{,}000072Mu*Yo + 0{,}000055Mu*Co +$$
$$0{,}000110Cu*Ag - 0{,}000104Ag*Yo + 0{,}000005Ag*Ag$$

Regression analysis of L110 vs. Yu, Mu, Cu, Ag, Yo, Mo, Co:
Terms Yu*Yo, Mu*Mo and Cu*Co have been omitted.
Transformation: Box-Cox, λ=0,5

$$L110\wedge 0{,}5 =$$
$$9{,}3345 - 0{,}003320Yu - 0{,}02998Mu - 0{,}02648Cu - 0{,}03152Ag -$$
$$0{,}003082Yo - 0{,}026798Mo - 0{,}02148Co + 0{,}000023Mu*Mu +$$
$$0{,}000057Cu*Cu + 0{,}000241Ag*Ag + 0{,}000027Co*Co +$$
$$0{,}000023Yu*Mu - 0{,}000015Yu*Cu - 0{,}000036Yu*Co +$$
$$0{,}000044Mu*Cu + 0{,}000097Mu*Ag + 0{,}000024Mu*Yo -$$
$$0{,}000023Mu*Co + 0{,}000077Cu*Ag - 0{,}000018Cu*Yo +$$
$$0{,}000012Ag*Yo + 0{,}000078Ag*Mo + 0{,}000053Ag*Co -$$
$$0{,}000018Yo*Co - 0{,}000020Mo*Co - 0{,}000001Ag*Ag*Ag$$

Regression analysis of a15 vs. Yu; Mu; Cu; Ag; Yo; Mo; Co
Terms Yu*Yo, Mu*Mo and Cu*Co have been omitted.

$$a15 = -0{,}77 - 0{,}0840Yu + 0{,}5660Mu - 0{,}3045Cu - 0{,}0402Ag -$$
$$0{,}0914Yo + 0{,}5056Mo - 0{,}3992Co - 0{,}001199Mu*Mu +$$
$$0{,}001142Yu*Ag - 0{,}000731Mu*Cu - 0{,}004108Mu*Ag +$$
$$0{,}003150Cu*Ag + 0{,}000787Ag*Yo - 0{,}000677Yo*Mo -$$
$$0{,}000677Yo*Mo - 0{,}000728Yo*Co + 0{,}000544Mo*Co$$

Regression analysis of a110 vs. Yu; Mu; Cu; Ag; Yo; Mo; Co
Terms Yu*Yo, Mu*Mo and Cu*Co have been omitted.

$$a110 = 2{,}57 - 0{,}0669Yu + 0{,}6112Mu - 0{,}5575Cu - 0{,}0638Ag -$$
$$0{,}0756Yo + 0{,}6033Mo - 0{,}4918Co + 0{,}000907Cu*Cu +$$
$$0{,}000535Yo*Yo - 0{,}001504Yu*Cu + 0{,}000809Yu*Ag +$$
$$0{,}000218Yu*Mo - 0{,}001210Yu*Co - 0{,}000463Mu*Cu -$$
$$0{,}002965Mu*Ag - 0{,}000534Mu*Yo + 0{,}003321Cu*Ag -$$
$$0{,}001455Cu*Yo + 0{,}000327Ag*Yo - 0{,}002109Ag*Mo +$$
$$0{,}002727Ag*Co - 0{,}001929Yo*Co - 0{,}000583Mo*Co$$

Regression analysis of b15 vs. Yu; Mu; Cu; Ag; Yo; Mo; Co
Terms Yu*Yo, Mu*Mo and Cu*Co have been omitted.

$$b15 = 0{,}74 + 0{,}4050Yu - 0{,}0697Mu - 0{,}3730Cu -$$
$$0{,}0432Ag + 0{,}5415Yo - 0{,}0112Mo - 0{,}3964Co +$$
$$0{,}001314Cu*Cu - 0{,}000998Yu*Mu - 0{,}003342Yu*Ag -$$
$$0{,}000959Yu*Mo + 0{,}001208Mu*Ag - 0{,}001221Mu*Yo +$$
$$0{,}002051Cu*Ag + 0{,}001624Ag*Yo - 0{,}001997Yo*Mo$$

Regression analysis of b110 vs. Yu; Mu; Cu; Ag; Yo; Mo; Co
Terms Yu*Yo, Mu*Mo and Cu*Co have been omitted.

$$b110 = 3{,}68 + 0{,}6809Yu - 0{,}1744Mu - 0{,}6101Cu -$$
$$0{,}0788Ag + 0{,}7645Yo - 0{,}1641Mo - 0{,}5472Co +$$
$$0{,}000748Yu*Yu + 0{,}000632Mu*Mu + 0{,}001817Cu*Cu +$$
$$0{,}000361Ag*Ag + 0{,}000336Mo*Mo + 0{,}001328Co*Co -$$
$$0{,}002659Yu*Mu - 0{,}001041Yu*Cu - 0{,}002724Yu*Ag -$$
$$0{,}002268Yu*Mo - 0{,}001149Yu*Co + 0{,}001218Mu*Cu +$$
$$0{,}001143Mu*Ag - 0{,}002279Mu*Yo + 0{,}000425Mu*Co +$$
$$0{,}001874Cu*Ag - 0{,}000531Cu*Yo + 0{,}000985Cu*Mo -$$
$$0{,}002079Ag*Yo + 0{,}001176Ag*Mo + 0{,}001427Ag*Co -$$
$$0{,}002519Yo*Mo - 0{,}000907Yo*Co + 0{,}000629Mo*Co$$

Calculating the Prognosis

An evenly distributed grid was laid over the entire region of interest (ROI), with each grid point representing a combination of the settings of all the factors involved in the test. On the basis of the empirical models, all expected values of the responses L[−15], L[15], . . . L[110], a[−15] . . . a[110], and b[−15] . . . b[110] and associated confidence intervals were then calculated and tabulated making use of the statistics program Minitab, version 18 for all these combinations by inserting the coordinates of the grid points into the models. As a rule, a confidence level of 95% is well suited.

Further details about the confidence level of 95% are described in George E. P. Box, J. Stuart Hunter, William G. Hunter, "Statistics for Experimenters", Wiley 2005, ISBN-13: 978-0471718130, by George E. P. Box, Norman R. Draper: "Empirical Model-Building and Response Surfaces", Wiley 1987, ISBN-13: 978-0471810339, and by Peter Goos, Bradley Jones: "Optimal Design of Experiments—A Case Study Approach", Wiley 2011, ISBN-13: 978-0470744611.

The next table shows exemplarily a part of the prognosis table, listing the prognosis values for L, a, b, C and h° at viewing angles 15° and 110°, as well as the confidence intervals for L, a, and b values at these observation angles.

YuP, MuP, CuP representing the first layers b), AgP representing the silver effect pigment layer c), and YoP, MoP, CoP representing the second layers d). "P" is added to clearly distinguish between measured data and prognosis data. The extensions "PK95u" and "PK95o" represent the upper and lower limit of the confidence interval of 95% of the respective prognosis value.

| Settings | | | | | | |
|---|---|---|---|---|---|---|
| YuP | MuP | CuP | AgP | YoP | MoP | CoP |
| 0 | 0 | 25 | 25 | 0 | 0 | 0 |
| 0 | 0 | 25 | 25 | 0 | 0 | 25 |
| 0 | 0 | 25 | 25 | 0 | 0 | 50 |
| 0 | 0 | 25 | 25 | 0 | 0 | 75 |
| 0 | 0 | 25 | 25 | 0 | 0 | 100 |
| 0 | 0 | 25 | 25 | 0 | 25 | 0 |
| 0 | 0 | 25 | 25 | 0 | 25 | 25 |
| 0 | 0 | 25 | 25 | 0 | 25 | 50 |
| 0 | 0 | 25 | 25 | 0 | 25 | 75 |
| 0 | 0 | 25 | 25 | 0 | 25 | 100 |
| 0 | 0 | 25 | 25 | 0 | 50 | 0 |
| 0 | 0 | 25 | 25 | 0 | 50 | 25 |
| 0 | 0 | 25 | 25 | 0 | 50 | 50 |
| 0 | 0 | 25 | 25 | 0 | 50 | 75 |
| 0 | 0 | 25 | 25 | 0 | 50 | 100 |
| 0 | 0 | 25 | 25 | 0 | 75 | 0 |
| 0 | 0 | 25 | 25 | 0 | 75 | 25 |
| 0 | 0 | 25 | 25 | 0 | 75 | 50 |
| 0 | 0 | 25 | 25 | 0 | 75 | 75 |
| 0 | 0 | 25 | 25 | 0 | 75 | 100 |
| 0 | 0 | 25 | 25 | 0 | 100 | 0 |
| 0 | 0 | 25 | 25 | 0 | 100 | 25 |
| 0 | 0 | 25 | 25 | 0 | 100 | 50 |
| 0 | 0 | 25 | 25 | 0 | 100 | 75 |
| 0 | 0 | 25 | 25 | 0 | 100 | 100 |
| 0 | 0 | 25 | 25 | 25 | 0 | 0 |
| 0 | 0 | 25 | 25 | 25 | 0 | 25 |
| 0 | 0 | 25 | 25 | 25 | 0 | 50 |
| 0 | 0 | 25 | 25 | 25 | 0 | 75 |
| 0 | 0 | 25 | 25 | 25 | 0 | 100 |
| 0 | 0 | 25 | 25 | 25 | 25 | 0 |
| 0 | 0 | 25 | 25 | 25 | 25 | 25 |
| 0 | 0 | 25 | 25 | 25 | 25 | 50 |
| 0 | 0 | 25 | 25 | 25 | 25 | 75 |
| 0 | 0 | 25 | 25 | 25 | 25 | 100 |
| 0 | 0 | 25 | 25 | 25 | 25 | 0 |
| 0 | 0 | 25 | 25 | 25 | 25 | 25 |
| 0 | 0 | 25 | 25 | 25 | 25 | 50 |
| 0 | 0 | 25 | 25 | 25 | 25 | 75 |
| 0 | 0 | 25 | 25 | 25 | 25 | 100 |
| 0 | 0 | 25 | 25 | 25 | 25 | 0 |
| 0 | 0 | 25 | 25 | 25 | 25 | 25 |
| 0 | 0 | 25 | 25 | 25 | 75 | 50 |
| 0 | 0 | 25 | 25 | 25 | 75 | 75 |
| 0 | 0 | 25 | 25 | 25 | 75 | 100 |
| 0 | 0 | 25 | 25 | 25 | 100 | 0 |
| 0 | 0 | 25 | 25 | 25 | 100 | 25 |
| 0 | 0 | 25 | 25 | 25 | 100 | 50 |
| 0 | 0 | 25 | 25 | 25 | 100 | 75 |
| 0 | 0 | 25 | 25 | 25 | 100 | 100 |
| 0 | 0 | 25 | 25 | 50 | 0 | 0 |
| 0 | 0 | 25 | 25 | 50 | 0 | 25 |

| Prognosis | confidence interval | | Prognosis | confidence interval | | Prognosis | confidence interval | | Prognosis | confidence interval | |
|---|---|---|---|---|---|---|---|---|---|---|---|
| L15P | L15PK95u | L15PK95o | L110P | L110PK95u | L110PK95o | a15P | a15PK95u | a15PK95o | a110P | a110PK95u | a110PK95o |
| 102.1 | 96.2 | 108.1 | 65.6 | 64.3 | 67.0 | −7.4 | −10.4 | −4.4 | −10.3 | −11.8 | −8.8 |
| 91.3 | 85.8 | 97.1 | 58.0 | 56.8 | 59.2 | −17.4 | −20.2 | −14.6 | −20.9 | −22.3 | −19.5 |
| 81.2 | 75.1 | 87.5 | 51.3 | 49.9 | 52.7 | −27.4 | −30.2 | −24.5 | −31.5 | −33.0 | −30.0 |
| 71.7 | 64.6 | 79.1 | 45.5 | 43.9 | 47.1 | −37.4 | −40.5 | −34.2 | −42.1 | −43.9 | −40.3 |
| 62.7 | 54.6 | 71.4 | 40.4 | 38.5 | 42.4 | −47.3 | −50.9 | −43.7 | −52.7 | −55.0 | −50.4 |
| 94.3 | 88.9 | 99.9 | 56.0 | 54.8 | 57.2 | 5.2 | 2.5 | 7.9 | 3.5 | 2.0 | 4.9 |
| 84.0 | 78.9 | 89.3 | 48.7 | 47.7 | 49.8 | −4.4 | −7.0 | −1.9 | −7.5 | −8.7 | −6.3 |
| 74.3 | 68.6 | 80.2 | 42.5 | 41.3 | 43.6 | −14.1 | −16.6 | −11.5 | −18.5 | −19.8 | −17.1 |
| 65.2 | 58.5 | 72.2 | 37.0 | 35.7 | 38.4 | −23.7 | −26.5 | −20.9 | −29.4 | −31.2 | −27.6 |
| 56.7 | 49.0 | 64.9 | 32.3 | 30.7 | 34.0 | −33.3 | −36.5 | −30.2 | −40.4 | −42.7 | −38.1 |
| 86.8 | 81.7 | 92.1 | 47.1 | 46.0 | 48.2 | 17.9 | 15.2 | 20.5 | 17.2 | 15.7 | 18.7 |
| 77.0 | 72.1 | 82.0 | 40.3 | 39.4 | 41.2 | 8.6 | 6.1 | 11.0 | 5.9 | 4.6 | 7.2 |
| 67.7 | 62.2 | 73.4 | 34.5 | 33.4 | 35.5 | −0.7 | −3.3 | 1.8 | −5.4 | −6.9 | −3.9 |
| 59.0 | 52.6 | 65.7 | 29.4 | 28.2 | 30.7 | −10.0 | −12.9 | −7.2 | −16.7 | −18.7 | −14.8 |
| 50.9 | 43.6 | 58.8 | 25.2 | 23.7 | 26.6 | −19.3 | −22.6 | −16.1 | −28.1 | −30.6 | −25.5 |
| 79.7 | 74.6 | 84.9 | 38.9 | 37.9 | 40.0 | 30.5 | 27.6 | 33.4 | 31.0 | 29.3 | 32.6 |
| 70.2 | 65.4 | 75.2 | 32.7 | 31.8 | 33.5 | 21.5 | 18.9 | 24.2 | 19.3 | 17.8 | 20.8 |
| 61.4 | 56.0 | 67.0 | 27.3 | 26.3 | 28.3 | 12.6 | 9.8 | 15.3 | 7.6 | 5.8 | 9.4 |
| 53.1 | 47.0 | 59.7 | 22.7 | 21.6 | 23.9 | 3.6 | 0.4 | 6.8 | −4.1 | −6.4 | −1.7 |

-continued

| | | | | | | | | | | | |
|---|---|---|---|---|---|---|---|---|---|---|---|
| 45.5 | 38.5 | 53.1 | 18.9 | 17.6 | 20.2 | −5.3 | −9.2 | −1.5 | −15.8 | −18.8 | −12.7 |
| 72.8 | 67.7 | 78.1 | 31.6 | 30.5 | 32.6 | 43.1 | 39.7 | 46.5 | 44.7 | 42.8 | 46.7 |
| 63.8 | 58.9 | 68.9 | 25.8 | 25.0 | 26.7 | 34.5 | 31.5 | 37.5 | 32.7 | 30.9 | 34.5 |
| 55.4 | 50.1 | 61.0 | 21.0 | 20.1 | 21.9 | 25.9 | 22.7 | 29.1 | 20.6 | 18.5 | 22.8 |
| 47.6 | 41.5 | 54.0 | 16.9 | 15.9 | 18.0 | 17.3 | 13.5 | 21.1 | 8.6 | 5.8 | 11.4 |
| 40.3 | 33.6 | 47.7 | 13.5 | 12.3 | 14.7 | 8.7 | 3.9 | 13.4 | −3.5 | −7.1 | 0.2 |
| 103.3 | 98.2 | 108.6 | 64.3 | 63.1 | 65.6 | −9.2 | −11.8 | −6.6 | −12.6 | −13.9 | −11.3 |
| 92.5 | 87.7 | 97.5 | 56.6 | 55.5 | 57.7 | −19.6 | −22.1 | −17.2 | −24.4 | −25.6 | −23.2 |
| 82.3 | 76.8 | 88.1 | 49.8 | 48.6 | 51.1 | −30.1 | −32.6 | −27.5 | −36.2 | −37.4 | −34.9 |
| 72.7 | 66.0 | 79.8 | 43.9 | 42.4 | 45.4 | −40.5 | −43.3 | −37.7 | −48.0 | −49.5 | −46.4 |
| 63.7 | 55.9 | 72.1 | 38.8 | 37.1 | 40.6 | −50.9 | −54.2 | −47.7 | −59.8 | −61.7 | −57.8 |
| 95.5 | 90.8 | 100.3 | 54.8 | 53.7 | 55.8 | 3.0 | 0.7 | 5.4 | 1.2 | 0.0 | 2.4 |
| 85.1 | 80.7 | 89.7 | 47.5 | 46.6 | 48.4 | −7.1 | −9.3 | −4.9 | −11.0 | −12.0 | −9.9 |
| 75.4 | 70.2 | 80.7 | 41.1 | 40.0 | 42.2 | −17.2 | −19.5 | −14.9 | −23.1 | −24.3 | −21.9 |
| 66.2 | 59.9 | 72.8 | 35.6 | 34.4 | 36.9 | −27.3 | −29.8 | −24.8 | −35.3 | −36.8 | −33.8 |
| 57.6 | 50.2 | 65.6 | 30.9 | 29.4 | 32.4 | −37.4 | −40.2 | −34.5 | −47.5 | −49.4 | −45.5 |
| 88.0 | 83.6 | 92.5 | 46.0 | 45.0 | 46.9 | 15.2 | 12.9 | 17.5 | 15.0 | 13.7 | 16.2 |
| 78.1 | 73.8 | 82.4 | 39.1 | 38.3 | 39.9 | 5.5 | 3.3 | 7.6 | 2.4 | 1.3 | 3.6 |
| 68.7 | 63.7 | 73.9 | 33.3 | 32.3 | 34.2 | −4.3 | −6.5 | −2.0 | −10.1 | −11.4 | −8.7 |
| 60.0 | 53.9 | 66.3 | 28.2 | 27.1 | 29.3 | −14.0 | −16.6 | −11.4 | −22.6 | −24.4 | −20.8 |
| 51.8 | 44.7 | 59.4 | 23.9 | 22.6 | 25.2 | −23.8 | −26.9 | −20.7 | −35.2 | −37.4 | −32.9 |
| 80.6 | 76.4 | 85.3 | 37.9 | 37.0 | 38.8 | 27.4 | 25.0 | 29.9 | 28.7 | 27.3 | 30.2 |
| 71.3 | 67.1 | 75.6 | 31.6 | 30.9 | 32.4 | 18.0 | 15.8 | 20.3 | 15.8 | 14.5 | 17.2 |
| 62.4 | 57.5 | 67.5 | 26.2 | 25.3 | 27.1 | 8.6 | 6.1 | 11.1 | 2.9 | 1.3 | 4.6 |
| 54.0 | 48.2 | 60.3 | 21.6 | 20.6 | 22.7 | −0.8 | −3.9 | 2.3 | −10.0 | −12.2 | −7.7 |
| 46.3 | 39.5 | 53.7 | 17.8 | 16.6 | 19.0 | −10.2 | −14.1 | −6.3 | −22.8 | −25.7 | −20.0 |
| 73.9 | 69.4 | 78.6 | 30.7 | 29.8 | 31.6 | 39.7 | 36.8 | 42.5 | 42.5 | 40.7 | 44.2 |
| 64.8 | 60.4 | 69.3 | 24.9 | 24.1 | 25.6 | 30.6 | 28.0 | 33.1 | 29.2 | 27.5 | 30.9 |
| 56.3 | 51.4 | 61.5 | 20.0 | 19.2 | 20.9 | 21.5 | 18.5 | 24.5 | 16.0 | 13.9 | 18.1 |
| 48.4 | 42.7 | 54.6 | 16.0 | 15.0 | 16.9 | 12.4 | 8.6 | 16.3 | 2.7 | 0.0 | 5.5 |
| 41.1 | 34.6 | 48.3 | 12.6 | 11.5 | 13.7 | 3.4 | −1.6 | 8.3 | −10.5 | −14.0 | −7.0 |
| 104.6 | 99.6 | 109.7 | 63.1 | 61.8 | 64.3 | −11.0 | −13.6 | −8.4 | −14.2 | −15.6 | −12.8 |
| 93.7 | 89.0 | 98.6 | 55.2 | 54.1 | 56.4 | −21.9 | −24.4 | −19.4 | −27.2 | −28.5 | −25.9 |

| Prognosis | confidence interval | | Prognosis | confidence interval | | Prognosis | Prognosis | Prognosis | Prognosis |
|---|---|---|---|---|---|---|---|---|---|
| b15P | b15PK95u | b15PK95o | b110P | b110PK95u | b110PK95o | C15P | C110P | h15P | h110P |
| −7.6 | −11.5 | −3.6 | −11.0 | −13.1 | −8.9 | 10.6 | 15.1 | 225.6 | 226.9 |
| −17.5 | −21.4 | −13.6 | −23.0 | −24.9 | −21.0 | 24.7 | 31.1 | 225.1 | 227.7 |
| −27.4 | −31.4 | −23.4 | −33.3 | −35.5 | −31.0 | 38.7 | 45.8 | 225.0 | 226.6 |
| −37.3 | −41.5 | −33.1 | −41.9 | −44.6 | −39.2 | 52.8 | 59.4 | 225.0 | 224.9 |
| −47.2 | −51.7 | −42.7 | −48.9 | −52.2 | −45.6 | 66.8 | 71.9 | 224.9 | 222.9 |
| −7.8 | −11.0 | −4.6 | −13.6 | −15.2 | −11.9 | 9.4 | 14.0 | 303.7 | 284.3 |
| −17.8 | −20.9 | −14.6 | −25.1 | −26.7 | −23.5 | 18.3 | 26.2 | 256.0 | 253.4 |
| −27.7 | −30.9 | −24.4 | −35.0 | −37.0 | −33.1 | 31.0 | 39.6 | 243.1 | 242.2 |
| −37.6 | −41.1 | −34.1 | −43.3 | −45.7 | −40.8 | 44.4 | 52.3 | 237.8 | 235.8 |
| −47.5 | −51.3 | −43.6 | −49.9 | −52.9 | −46.8 | 58.0 | 64.2 | 234.9 | 231.0 |
| −8.1 | −11.2 | −5.0 | −15.7 | −17.4 | −14.0 | 19.6 | 23.3 | 335.6 | 317.7 |
| −18.0 | −21.1 | −15.0 | −26.8 | −28.5 | −25.2 | 20.0 | 27.5 | 295.4 | 282.4 |
| −27.9 | −31.1 | −24.8 | −36.4 | −38.4 | −34.4 | 28.0 | 36.8 | 268.5 | 261.5 |
| −37.9 | −41.2 | −34.5 | −44.2 | −46.7 | −41.8 | 39.2 | 47.3 | 255.2 | 249.3 |
| −47.8 | −51.5 | −44.0 | −50.4 | −53.5 | −47.3 | 51.5 | 57.7 | 248.0 | 240.9 |
| −8.4 | −12.1 | −4.7 | −17.4 | −19.3 | −15.4 | 31.6 | 35.5 | 344.6 | 330.7 |
| −18.3 | −21.9 | −14.7 | −28.2 | −30.0 | −26.3 | 28.3 | 34.1 | 319.6 | 304.4 |
| −28.2 | −31.9 | −24.5 | −37.3 | −39.4 | −35.1 | 30.9 | 38.0 | 294.0 | 281.5 |
| −38.1 | −42.1 | −34.2 | −44.7 | −47.4 | −42.1 | 38.3 | 44.9 | 275.4 | 264.8 |
| −48.0 | −52.3 | −43.8 | −50.5 | −53.8 | −47.3 | 48.3 | 52.9 | 263.7 | 252.7 |
| −8.7 | −13.4 | −4.0 | −18.7 | −21.1 | −16.2 | 44.0 | 48.5 | 348.6 | 337.4 |
| −18.6 | −23.2 | −13.9 | −29.0 | −31.4 | −26.7 | 39.2 | 43.7 | 331.7 | 318.4 |
| −28.5 | −33.2 | −23.8 | −37.8 | −40.4 | −35.2 | 38.5 | 43.0 | 312.3 | 298.7 |
| −38.4 | −43.3 | −33.5 | −44.8 | −47.9 | −41.8 | 42.1 | 45.7 | 294.2 | 280.9 |
| −48.3 | −53.5 | −43.1 | −50.2 | −54.0 | −46.5 | 49.1 | 50.4 | 280.2 | 266.1 |
| 7.0 | 3.9 | 10.1 | 6.5 | 4.7 | 8.2 | 11.6 | 14.1 | 142.8 | 152.8 |
| −2.9 | −5.9 | 0.1 | −6.1 | −7.7 | −4.4 | 19.9 | 25.1 | 188.4 | 194.0 |
| −12.8 | −15.9 | −9.7 | −16.9 | −18.9 | −14.9 | 32.7 | 39.9 | 203.1 | 205.1 |
| −22.7 | −26.1 | −19.4 | −26.1 | −28.5 | −23.7 | 46.5 | 54.6 | 209.3 | 208.5 |
| −32.6 | −36.4 | −28.9 | −33.7 | −36.6 | −30.7 | 60.5 | 68.6 | 212.7 | 209.4 |
| 5.5 | 2.9 | 8.0 | 2.4 | 1.0 | 3.7 | 6.2 | 2.6 | 61.2 | 63.2 |
| −4.4 | −7.0 | −1.9 | −9.8 | −11.2 | −8.4 | 8.4 | 14.7 | 212.1 | 221.7 |
| −14.4 | −17.0 | −11.7 | −20.3 | −22.0 | −18.5 | 22.4 | 30.7 | 219.9 | 221.2 |
| −24.3 | −27.2 | −21.3 | −29.1 | −31.2 | −26.9 | 36.5 | 45.7 | 221.7 | 219.5 |
| −34.2 | −37.5 | −30.8 | −36.2 | −39.0 | −33.5 | 50.6 | 59.7 | 222.4 | 217.3 |
| 3.9 | 1.4 | 6.5 | −1.3 | −2.8 | 0.1 | 15.7 | 15.0 | 14.5 | 354.9 |
| −6.0 | −8.4 | −3.5 | −13.1 | −14.5 | −11.7 | 8.1 | 13.3 | 312.5 | 280.5 |
| −15.9 | −18.5 | −13.3 | −23.2 | −25.0 | −21.4 | 16.5 | 25.3 | 254.9 | 246.4 |
| −25.8 | −28.7 | −22.9 | −31.6 | −33.8 | −29.4 | 29.4 | 38.9 | 241.4 | 234.4 |
| −35.7 | −39.1 | −32.4 | −38.3 | −41.1 | −35.6 | 42.9 | 52.0 | 236.3 | 227.5 |

-continued

| | | | | | | | | | |
|---|---|---|---|---|---|---|---|---|---|
| 2.4 | −0.6 | 5.4 | −4.6 | −6.2 | −3.0 | 27.5 | 29.1 | 5.0 | 350.9 |
| −7.5 | −10.4 | −4.6 | −16.0 | −17.5 | −14.4 | 19.5 | 22.5 | 337.4 | 314.7 |
| −17.4 | −20.4 | −14.4 | −25.7 | −27.6 | −23.7 | 19.4 | 25.8 | 296.3 | 276.5 |
| −27.3 | −30.6 | −24.0 | −33.7 | −36.1 | −31.3 | 27.3 | 35.1 | 268.3 | 253.5 |
| −37.2 | −40.9 | −33.5 | −40.0 | −43.0 | −37.0 | 38.6 | 46.1 | 254.6 | 240.3 |
| 0.9 | −2.8 | 4.6 | −7.5 | −9.6 | −5.4 | 39.7 | 43.1 | 1.3 | 350.0 |
| −9.0 | −12.7 | −5.4 | −18.4 | −20.4 | −16.5 | 31.9 | 34.6 | 343.5 | 327.8 |
| −18.9 | −22.7 | −15.2 | −27.7 | −30.0 | −25.4 | 28.7 | 32.0 | 318.6 | 299.9 |
| −28.9 | −32.8 | −24.9 | −35.4 | −38.1 | −32.6 | 31.4 | 35.5 | 293.3 | 274.4 |
| −38.8 | −43.1 | −34.4 | −41.3 | −44.8 | −37.9 | 38.9 | 42.7 | 274.9 | 255.7 |
| 21.5 | 18.7 | 24.4 | 24.0 | 22.3 | 25.6 | 24.2 | 27.8 | 117.1 | 120.6 |
| 11.6 | 8.9 | 14.4 | 10.9 | 9.2 | 12.5 | 24.8 | 29.3 | 152.0 | 158.2 |

LIST OF REFERENCES

10 Multi-layer system
12 Substrate
14 Ink Sequence
18 First colour layer
20 Effect layer
22 Second colour layer
26 First dye/pigment
28 Platelet-shaped effect pigment
30 Second dye/pigment
40 Irradiated light beam
42 Angle of reflection of the irradiated light beam
44, 44', 44" Angle of measurement of reflectance/scattering/colour shade/Observation angle
46 Pigment particle
48 Particle length
50 Particle width
52 Norm light
54 Surface of layer
56 Gloss
58 Haze
60 Sensor
β Angle of incidence of norm light

The invention claimed is:

1. A method for making a multi-layer system showing a predetermined colour flip-flop effect, wherein the method comprises
   a) providing a substrate,
   b) depositing at least one first colour layer containing a colourant on the substrate a),
   c) depositing on the at least one first colour layer an effect layer containing at least one platelet-shaped effect pigment, and
   d) depositing on the effect layer at least one second colour layer containing a colourant,
   wherein each of the at least one first colour layer and of the at least one second colour layer contains a colourant which is not a platelet-shaped effect pigment, wherein the method further comprises the following steps:
   i) specifying a first target value for the colour shade, for the colour brightness or for the colour shade and the colour brightness of the top side of the multi-layer system seen at a first observation angle,
   ii) specifying a second target value for the colour shade, for the colour brightness or for the colour shade and the colour brightness of the top side of the multi-layer system seen at a second observation angle, wherein the second observation angle is different from the first observation angle, and wherein the second target value is different from the first target value,
   iii) specifying a colourant system comprising at least one colourant and further comprising one effect pigment layer recipe being suitable for forming the effect layer,
   iv) providing at least one empirical model of the relationship between the colour shades, between the colour brightness or between the colour shade and the colour brightness at at least two different observation angles comprising at least the first observation angle and the second observation angle specified in step ii) of the top side of a first number of multi-layer system, at least 90% of which comprising at least one first colour layer having at least one colourant as specified in step iii), at least one second colour layer having at least one colourant as specified in step iii) and an effect layer made of the effect pigment layer recipe specified in step iii), and
   v) determining-making use of the at least one empirical model provided in step iv)—the composition of a multi-layer system having within a predetermined tolerance the first target value specified in step i) and the second target value specified in step ii), or, if none is found, specifying α) a new tolerance for the first target value specified in step i), a new tolerance for the second target value specified in step ii) or a new tolerance for the first target value specified in step i) and for the second target value specified in step ii), or β) specifying in steps i) and ii) a new first target value, a new second target value or a new first and second target value, or γ) repeating the method by specifying in step iii) a different colourant system, wherein the determination in step v) is performed by using a computer program.

2. The method in accordance with claim 1, wherein the determination in step v) is performed by using a statistics program or by using a spreadsheet software as the computer program.

3. The method in accordance with claim 1 wherein the determination in step v) is performed by using a statistics program for a direct calculation of experimental settings that leads within a predetermined tolerance to the desired first target value specified in step i) and the second target value specified in step ii).

4. The method in accordance with claim 1, wherein the determination in step v) is performed by calculating—making use of the at least one empirical model provided in step iv)—a prognosis for the values of the colour shades and/or colour brightness at at least two different observation angles comprising at least the first observation angle and the second observation angle specified in steps i) and ii) of the top side of a second number of multi-layer systems, at least 90% of which comprising at least one first colour layer having at least one colourant as specified in step iii), at least one second colour layer having at least one colourant as specified in step iii) and an effect layer made of the effect pigment layer recipe specified in step iii), wherein the second number is higher than the first number, and by searching the prognosis, whether at least one of the second number of multi-layer systems of the prognosis comprises a multi-layer system having within a predetermined tolerance the first target value specified in step i) and the second target value specified in step ii).

5. The method in accordance with claim 1, wherein the colour flip-flop effect is a colour shade flip-flop effect so that in step i) a first target value for a first colour shade and in step ii) a second target value for a second colour shade are specified, wherein the first and second colour shades are different from each other, wherein the delta a/b is at least 15, wherein the delta a/b is determined according to the equation delta a/b=$((a[15°]-a[110°])^2+(b[15°]-b[110°])^2)^{1/2}$, wherein a [15°] is the a-value of the top side of the multi-layer system measured at a first observation value of 15°, a[110°] is the a-value of the top side of the multi-layer system measured at a second observation value of 110°, b[15°] is the b-value of the top side of the multi-layer system measured at an observation value of 15° and b[110°] is the b-value of the top side of the multi-layer system measured at an observation value of 110°, wherein the measurement is performed by irradiating in a dark environment a standardized light type onto the top side of the multi-layer system at an angle of incident ($\beta$) of 45° with respect to the horizontal direction and measuring the a-values of the top side of the multi-layer system at observation values of 15° and 110° and measuring the b-values of the top side of the multi-layer system at observation values of 15° and 110°, wherein the angle of reflection of 135° with respect to the horizontal direction is defined as an observation angle of 0°, and/or wherein the colour flip-flop effect is a colour brightness flip-flop effect so that in step i) a first target value for the ratio of a-/b-value of a first colour shade and a first brightness and in step ii) the same ratio of a-/b-value and a second brightness are specified, wherein the first and second colour shades are the same or different from each other and the first and second colour brightness are different from each other, wherein the delta L is at least 10, wherein the delta L is determined according to the equation delta L=|L[15°]−L[110°]|, wherein |L[15°]−L[110°]| means the absolute difference of both values L[15°] and L[110°], wherein L[15°] is the L-value of the top side of the multi-layer system measured at a first observation value of 15° and L[110°] is the L-value of the top side of the multi-layer system measured at a second observation value of 110°, wherein the measurement is performed by irradiating in a dark environment a standardized light onto the multi-layer system at an angle of incidence ($\beta$) of 45° with respect to the horizontal direction and measuring the L-values of the top side of the multi-layer system at observation values of 15° and 110°, wherein the angle of reflection of 135° with respect to the horizontal direction is defined as an observation angle of 0°.

6. The method in accordance with claim 1, wherein in step iii) a colourant system is specified, which comprises an effect pigment layer recipe including particles of at least one platelet-shaped effect pigment having an average length of 2 to 500 µm, an average width of 2 to 500 µm and an average thickness of at most 1 µm.

7. The method in accordance with claim 1, wherein in step iii) a colourant system is specified, which comprises at least three different colourants spanning a colour space covering at least 100,000 perceptual different colour shades being generable by applying a combination of one or more of the at least three different colourants above each other.

8. The method in accordance with claim 7, wherein in step iii) a colourant system is specified, which comprises a cyan colourant, a magenta colourant and a yellow colourant.

9. The method in accordance with claim 1, wherein the at least one empirical model provided in step iv) is an empirical model, which is selected from the group consisting of linear models, of second order models, and of higher order models.

10. The method in accordance with claims 1, wherein the at least one empirical model provided in step iv) has been obtained by making use of the results of a plurality of experiments, in which the colour shade and/or colour brightness of the top side of a plurality of multi-layer systems has been measured at least at the first observation angle and the second observation angle, wherein in the plurality of multi-layer systems the colour shade and/or colour brightness of the top side of the at least one first colour layer and the colour shade and/or colour brightness of the top side of the at least one second colour layer have been varied.

11. The method in accordance with claim 1, wherein the at least one empirical model provided in step iv) has been obtained by performing 50 to 5,000 experiments with different multiple-layer systems, wherein in the single experiments the colour shade and/or colour brightness of the top side of a plurality of multi-layer systems has been measured at least at the first observation angle and the second observation angle, wherein in the plurality of multi-layer systems the colour shade and/or colour brightness of the top side of the at least one first colour layer and the colour shade and/or colour brightness of the top side of the at least one second colour layer, the coverage of the at least one first colour layer, the coverage of the at least one second colour layer and/or the coverage of the effect layer have been varied.

12. The method in accordance with claim 1, wherein the at least one empirical model provided in step iv) has been obtained by performing the following steps:
α) providing in step iii) a colourant system, which comprises at least three different colourants spanning a colour space covering at least 100,000 perceptual different colour shades being generable by applying a combination of one or more of the at least three different colourants above each other, and further comprising an effect pigment layer recipe,
β) generating a design of experiments using a statistics program designed for calculating at least one empirical model so as to propose a plurality of experiments, wherein in each of these experiments a specific multi-layer system is formed under specific conditions using specific application parameters for applying the layers a) to d) onto a specific substrate, wherein at least 90% of these experiments differ from all other experiments of the plurality of experiments in at least one parameter,
γ) performing the plurality of experiments proposed in step β), wherein for each of the experiments at least the colour shade and/or colour brightness of the top side of the respective multi-layer system is measured at least at a first observation angle and a second observation angle,
δ) entering the numeric values of the colour shades and/or colour brightness measured in step γ) into the statistics program,
ε) allowing the statistics program to calculate the at least one empirical models.

13. The method in accordance with claim 1, wherein the at least one empirical model provided in step iv) has been obtained by making use of multi-layer systems, which all do not contain any interference pigment.

14. The method in accordance with claim 1, wherein the determination in step v) is performed by calculating-making use of the at least one empirical model provided in step iv)—a prognosis, wherein the prognosis is calculated for more than 5,000 different multi-layer systems.

15. The method in accordance with claim 1, wherein the determination in step v) is performed by calculating—making use of the at least one empirical model provided in step iv)—a prognosis, wherein each of the multi-layer systems of the prognosis differ from at least 80% from all other multi-layer systems of the prognosis in at least the colour shade of at least one of the at least one first colour layer, the colour shade of at least one of the at least one second colour layer, the coverage of at least one of the at least one first colour layer, the coverage of at least one of the at least one second colour layer and the coverage of the effect layer.

\* \* \* \* \*